United States Patent [19]
Arnold et al.

[11] Patent Number: 5,741,691
[45] Date of Patent: Apr. 21, 1998

[54] PARA-NITROBENZYL ESTERASES WITH ENHANCED ACTIVITY IN AQUEOUS AND NONAQUEOUS MEDIA

[75] Inventors: Frances H. Arnold; Jeffrey C. Moore, both of Pasadena, Calif.

[73] Assignee: California Institute of Technology, Pasadena, Calif.

[21] Appl. No.: 589,893

[22] Filed: Jan. 23, 1996

[51] Int. Cl.$^6$ .................. C12N 15/55; C12N 9/18; C12N 1/21; C12N 15/63

[52] U.S. Cl. .............. 435/197; 435/69.1; 435/71.2; 435/252.3; 435/252.33; 435/320.1; 435/172.1; 435/172.3; 536/23.2; 935/14; 935/29; 935/43; 935/56; 935/73

[58] Field of Search ............... 435/197, 196, 435/222, 68.1, 69.1, 252.3, 320.1, 7.4; 536/23.2

[56] References Cited

U.S. PATENT DOCUMENTS

| | | | |
|---|---|---|---|
| 5,316,935 | 5/1994 | Arnold et al. | 435/222 |
| 5,468,632 | 11/1995 | Cantwell et al. | 435/197 |

OTHER PUBLICATIONS

Arnold, F.H., "Engineering proteins for nonnatural environments," *The FASEB Journal*, vol. 7, pp. 744–749, 1993.

Chen, K., et al., "Tuning the activity of an enzyme for unusual environments: Sequential random mutagenesis of subtilisin E for catalysis in dimethylformamide," *Proc. Natl. Acad. Sci. USA*, vol. 90, pp. 5618–5622, 1993.

Moore et al. (1996). Nature Biotechnology 14: 458–467, Apr. 1996.

*Primary Examiner*—Robert A. Wax
*Assistant Examiner*—Tekchand Saidha
*Attorney, Agent, or Firm*—Oppenheimer Poms Smith

[57] ABSTRACT

A method for isolating and identifying modified para-nitrobenzyl esterases which exhibit improved stability and/or esterase hydrolysis activity toward selected substrates and under selected reaction conditions relative to the unmodified para-nitrobenzyl esterase. The method involves preparing a library of modified para-nitrobenzyl esterase nucleic acid segments (genes) which have nucleotide sequences that differ from the nucleic acid segment which encodes for unmodified para-nitrobenzyl esterase. The library of modified para-nitrobenzyl nucleic acid segments is expressed to provide a plurality of modified enzymes. The clones expressing modified enzymes are then screened to identify which enzymes have improved esterase activity by measuring the ability of the enzymes to hydrolyze the selected substrate under the selected reaction conditions. Specific modified para-nitrobenzyl esterases are disclosed which have improved stability and/or ester hydrolysis activity in aqueous or aqueous-organic media relative to the stability and/or ester hydrolysis activity of unmodified naturally occurring para-nitrobenzyl esterase.

12 Claims, 33 Drawing Sheets

LORACARBEF NUCLEUS-
p-NITROBENZYL
(LCN-pNB)
　　　　　　　　　LORACARBEF　　　p-NITROBENZYL
　　　　　　　　　NUCLEUS　　　　　ALCOHOL
　　　　　　　　　(LCN)　　　　　　(pNB)

p-NITROPHENYL ACETATE
(pNPA)
　　　　　　ACETATE　　　　p-NITROPHENOL
　　　　　　　　　　　　　　(pNP)

LORACARBEF NUCLEUS-
p-NITROPHENYL
(LCN-pNP)
　　　　　　　　　LORACARBEF　　　p-NITROPHENOL
　　　　　　　　　NUCLEUS　　　　　(pNP)
　　　　　　　　　(LCN)

FIG. 11
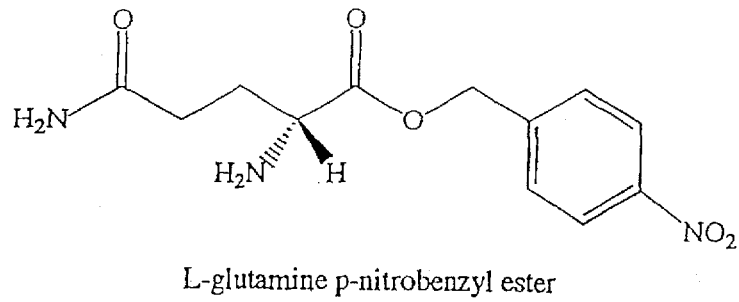
L-glutamine p-nitrobenzyl ester
a) 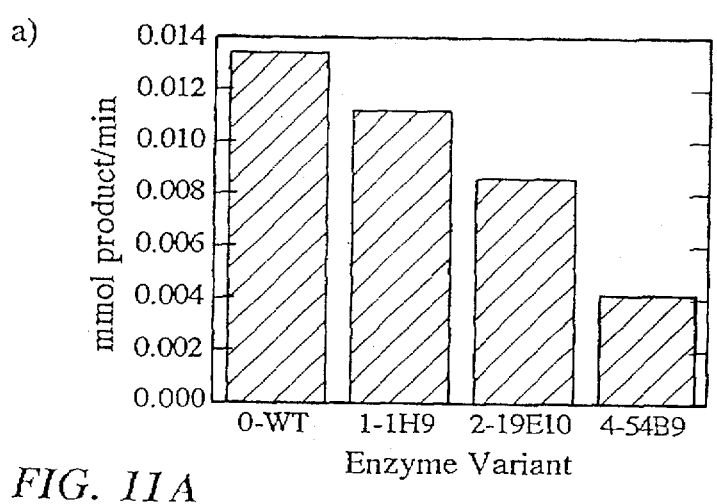
FIG. 11A
b) 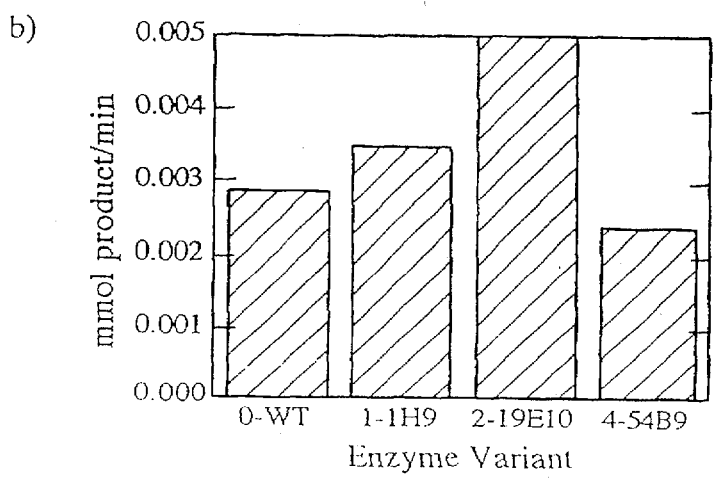
FIG. 11B

PARA-NITROBENZYL ESTERASES WITH ENHANCED ACTIVITY IN AQUEOUS AND NONAQUEOUS MEDIA

The U.S. Government has certain rights in this invention pursuant to Grant No. DE-FG02-93CH10578 awarded by the Department of Energy and Grant No. N00014-91-J-1397 awarded by the Department of the Navy.

BACKGROUND OF THE INVENTION

1. Field of the Invention

This invention relates to the creation, optimization and use of new enzyme catalysts for deprotection in organic synthesis. More specifically, the invention relates to enzymes optimized to remove ester-linked para-nitrobenzyl (pNB) protecting groups from carboxyl functional groups on β-lactam antibiotics and other compounds. This invention also relates to methods by which such enzymes can be altered and optimized for specific substrates and reaction conditions.

2. Description of Related Art

The publications and other reference materials referred to herein to describe the background of the invention and to provide additional details regarding its practice are hereby incorporated by reference. For convenience, the reference materials are numerically referenced and identified in the appended bibliography.

Efficient protection and deprotection of functional groups is critical to successful organic synthesis of polyfunctional molecules. Synthetic schemes often require that a given functional group be protected or deprotected selectively, under the mildest conditions and in the presence of functional groups of similar reactivity or other structures that are sensitive to acids, bases, oxidation and reduction. These situations represent severe problems for the synthesis of complex, polyfunctional molecules which cannot, or only with great difficulty, be solved using classical chemical tools.

The array of protecting group techniques can be substantially enriched by the application of enzymes. Enzymes can discriminate stereoisomers as well as offer the opportunity to carry out highly chemo- and regioselective transformations. The highly selective nature of enzymes may be exploited advantageously in the manipulation of protecting groups and in the synthesis of chiral compounds such as drugs and natural products. Furthermore, enzymes function under mild conditions, often operating at or near room temperature and at neutral, weakly acidic or weakly basic pH values. In many cases they combine a high selectivity for the reactions they catalyze and the structures they recognize with a broad substrate tolerance. Therefore, the application of enzymes can be viable alternatives to classical chemical protection/ deprotection methods for the introduction and/or removal of suitable protecting groups (1). The introduction of new enzymes with reactivities and substrate tolerances differing from existing enzymes is highly desirable.

Carboxy groups are often protected by conversion to the benzyl or para-nitrobenzyl (pNB) esters (2). Benzyl esters are resistant to treatment with reagents such as trifluoroacetic acid, triethylamine, diisopropylethylamine, but are readily removed by hydrogenolysis (over a Pd catalyst). Hydrogenolysis is not appropriate, however, for compounds containing double bonds, azides, imines, or activated aldehydes, or other functional groups that will be reduced. Benzyl esters can also be cleaved using a zinc catalyst under anhydrous conditions, but the extent of hydrolysis is variable and dependent on the conditions (e.g., time and temperature) of the reaction. The reaction must be carried out under anhydrous conditions, in an organic solvent. Both the organic solvent and catalyst can give rise to toxicity or disposal problems for large-scale reactions.

Modification by substitution in the aromatic ring can alter the sensitivity of the benzyl group towards deprotection by acidic reagents. PNB esters display increased resistance to acid hydrolysis.

During total synthesis or chemical modification of an antibiotic, several sites on the antibiotic could be adversely affected by the reagents used to carry out any given reaction step. Para-nitrobenzyl alcohol (pNB-OH) is commonly used to protect carboxylic acid functionalities in cephalosporin-derived antibiotics (U.S. Pat. No. 3,725,359 [1975]) (3). The pNB ester linkage is stable enough to withstand the various reaction conditions used in subsequent chemical steps. After chemical synthesis is completed, deprotection is required to return the cephalosporin-pNB ester to its original and active carboxylic acid form. The chemistry used to deprotect the carboxylic acid involves a catalytic form of zinc in concentrated organic solvent, and on an industrial scale this process generates large amounts of solvent and zinc-containing waste material. Cost is associated with processing of waste to make it safe for disposal. In 1975, scientists at Eli Lilly & Co. interested in pursuing alternative methods of deprotection for higher yield and lower disposal costs began a search for an esterase capable of performing this deprotection reaction (3).

The enzyme known as para-nitrobenzyl esterase (pNB esterase) was discovered in 1975 by scientists at Eli Lilly & Co., who screened whole cell preparations of numerous bacterial and fungal cultures for those possessing catalytic activity toward the hydrolysis of a p-nitrobenzyl protected cephalosporin (3). A *Bacillus subtilis* culture (NRRL B8079) showed the highest catalytic activity toward two cephalosporin-derived pNB-protected substrates of all the cultures tested. Although the reaction yield was high, the enzyme activity was not sufficient to consider for industrial application.

A chromatographically pure solution of pNB esterase was isolated at Eli Lilly, and its amino acid sequence partially determined. Using this partial sequence, DNA primers were constructed and used to isolate and sequence the gene for pNB esterase. This gene was cloned into *E. coli*, where it was over-expressed to produce pNB esterase in large quantities (4). However, partially purified enzyme preparations of "pNB esterase" could not compete with the speed, economy, or the small reaction volumes (due to lack of solubility of substrate in purely aqueous environments) of the zinc-catalyzed deprotection reaction.

The targeted reaction substrates have changed over the fifteen year period as well. Cephalosporin-derived antibiotics continued to evolve from the first generation cephalexin (one of the two original cephalosporin substrates used to search for pNB esterase), second generation cefaclor, third generation cefixime, and fourth generation loracarbef. These antibiotics have been developed to be readily absorbed (generation one), more potent (generation two), much more potent (generation three), and, finally, immensely more stable in the body (generation four) (5). They all are synthesized using the pNB ester protecting group (6). In protected form, with perhaps the exception of cefixime, all are only sparingly soluble in water.

The pNB esterase enzyme has been further characterized (6). It is a water soluble, monomeric serine esterase of 54 kD molecular weight and a pI of 4.1. The enzyme is active on a variety of ester substrates, ranging from the cephalosporin-derived compounds on which it was screened to a number of simple organic esters. Reported KM values for cephalosporin-derived substrates are in 0.5 to 2 mM range. The enzyme functions best at temperatures below 50° C., and its pH optimum is between 8 and 9.

The pNB esterase still suffers from a problem common to a large number of enzyme reactions in the performance of synthetic chemistry: the desired substrates are only sparingly soluble in water, and the enzyme's catalytic ability is drastically reduced by even small quantities of water-miscible non-aqueous solvents.

In view of the above problems with the existing pNB esterase, there is a continuing need to develop new enzymes which have expanded catalytic capabilities. In particular, new enzymes are needed which can be used to provide ester cleavage for a variety of substrates and settings, including polar non-aqueous solvents.

SUMMARY OF THE INVENTION

In accordance with the present invention, modified para-nitrobenzyl esterases are provided which have improved stability and/or ester hydrolysis activity in aqueous or aqueous-organic media relative to the stability and/or ester hydrolysis activity of unmodified naturally occurring para-nitrobenzyl esterase. Unmodified para-nitrobenzyl esterase has an amino acid sequence which includes numbered positions ranging sequentially from 1 to 489 (SEQ. ID. NO. 2).

As a feature of the present invention, it was discovered that substitution of amino acids at one or more specific amino acid positions resulted in the formation of enzymes having improved capabilities in aqueous and aqueous-organic media. The specific amino acid position numbers at which substitutions are made to achieve the modified para-nitrobenzyl esterases in accordance with the present invention are position Nos. 60, 94, 96, 144, 267, 271, 322, 334, 343, 358 and 370.

As a further feature of the present invention, specific amino acid substitutions are disclosed which provide specific modified para-nitrobenzyl esterases having improved stability and/or ester hydrolysis activity in organic media. The specific amino acid substitutions include I60V, S94G, N96S, L144M, K267R, F271L, H322R, L334V, L334S, A343V, M358V and Y370F. In accordance with the present invention, one or more of the specific substitutions increases the enzymatic activity and/or stability of the esterases in aqueous and aqueous-organic media. Ten specific modified para-nitrobenzyl esterases are disclosed which show enhanced activity in aqueous or aqueous-organic media over naturally occurring para-nitrobenzyl esterase. The amino acid sequences for these modified esterases are set forth in SEQ. ID. NOS. 4, 6, 8, 10, 12, 14, 16, 18, 20, and 22. These variants are also identified throughout the specification as 1-1h9, 2-19e10, 3-10c4, 4-38b9, 4-43e7, 4-54b9, 2-13f3, 2-23e1, 4-53d5 and 5-1a12, respectively. The naturally occurring esterase is identified as O-Wtpnb and is set forth in SEQ. ID. NO. 2.

As another feature of the present invention, a method is provided for isolating and identifying modified para-nitrobenzyl esterases which exhibit improved stability and/or esterase hydrolysis activity toward selected substrates and under selected reaction conditions relative to the unmodified para-nitrobenzyl esterase. The method involves preparing a library of modified para-nitrobenzyl esterase nucleic acid segments (genes) which have nucleotide sequences that differ from the nucleic acid segment which encodes for unmodified para-nitrobenzyl esterase. The library of modified para-nitrobenzyl nucleic acid segments is expressed to provide a plurality of modified enzymes. The clones expressing modified enzymes are then screened to identify which enzymes have improved esterase activity by measuring the ability of the enzymes to hydrolyze the selected substrate under the selected reaction conditions. Further modified variants can be produced by accumulating the beneficial mutations identified in this manner.

As an additional feature of the present invention, improvements in the catalytic activity of modified para-nitrobenzyl esterases with respect to a particular para-nitrobenzyl ester compound is determined by screening the modified enzymes with a substrate that is the para-nitrophenyl ester of the compound of interest. For example, screening of esterases for their ability to hydrolyze para-nitrobenzyl loracarbef is accomplished by screening the enzymes ability to hydrolyze para-nitrophenyl loracarbef. The use of para-nitrophenyl ester as a screening substrate is especially well-suited for screening large numbers of modified esterases because enzymatic activity is easily measured due to the generation of a colored product, i.e. para-nitrophenol. The yellow colored para-nitrophenyl cleavage product is easily measured to provide an accurate measure of the modified esters ability to hydrolyze the specific para-nitrobenzyl ester compound. Further, the ability of the modified enzymes to hydrolyze para-nitrophenyl ester is a good indication of the enzyme's ability to hydrolyze para-nitrobenzyl groups. This method allows the screening of large numbers of slightly different variations of enzymes which have been produced by random mutagenesis. This ability to easily screen large numbers of modified enzymes for their esterase activity increases the likelihood of identifying additional enzymes having increased activity in aqueous or aqueous-organic media and on other related substrates.

The above discussed and many other features and attendant advantages of the present invention will become better understood by reference to the following detailed description when taken in conjunction with the accompanying drawings.

BRIEF DESCRIPTION OF THE DRAWINGS

FIG. 1a shows the reaction wherein loracarbef nucleus-para-nitrobenzyl ester is hydrolyzed.

FIG. 1b shows the reaction wherein para-nitrophenyl acetate is hydrolyzed.

FIG. 1c shows the reaction wherein loracarbef nucleus-para-nitrophenyl ester is hydrolyzed.

Figure 3A:
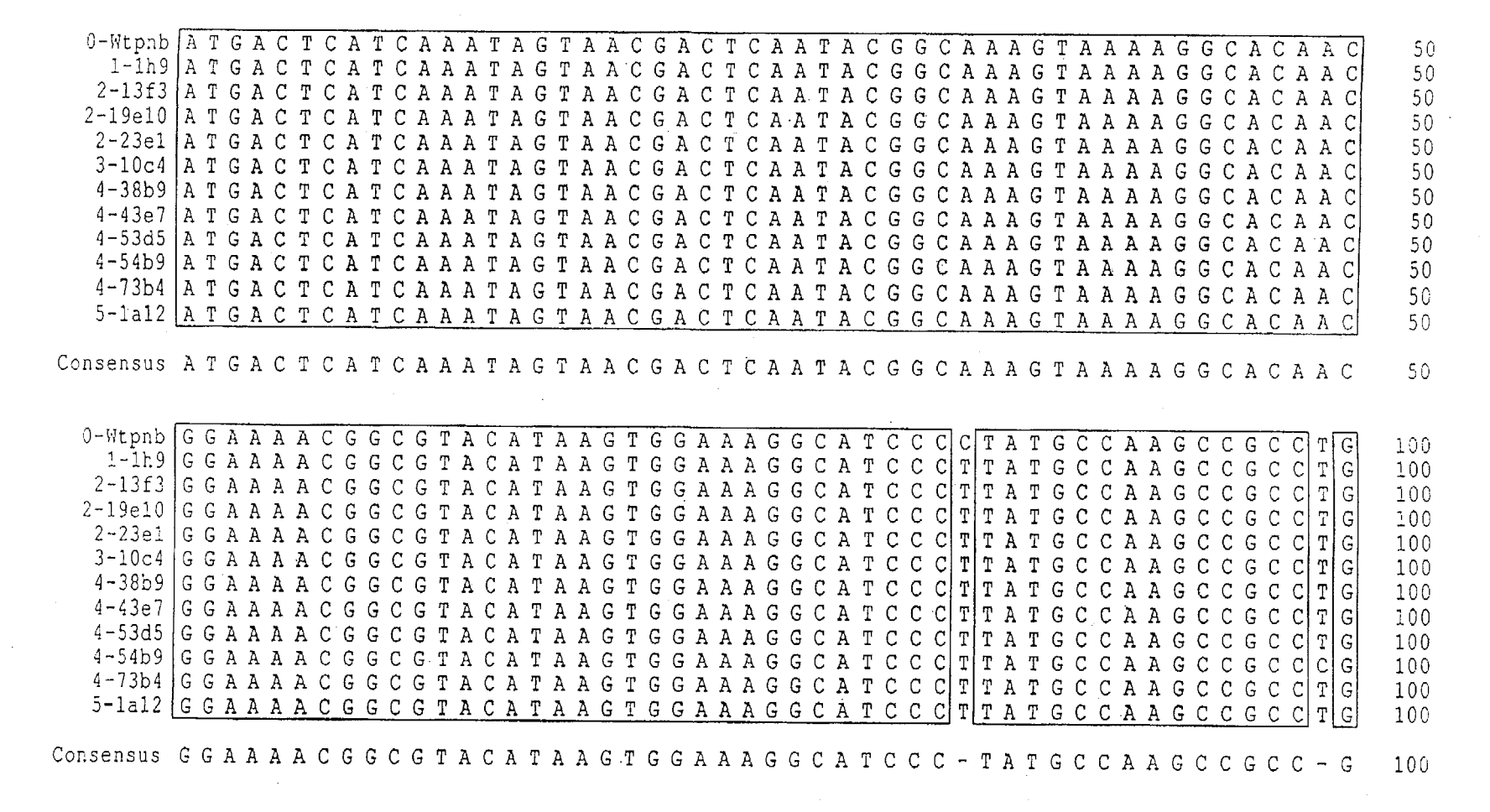
Figure 3B:
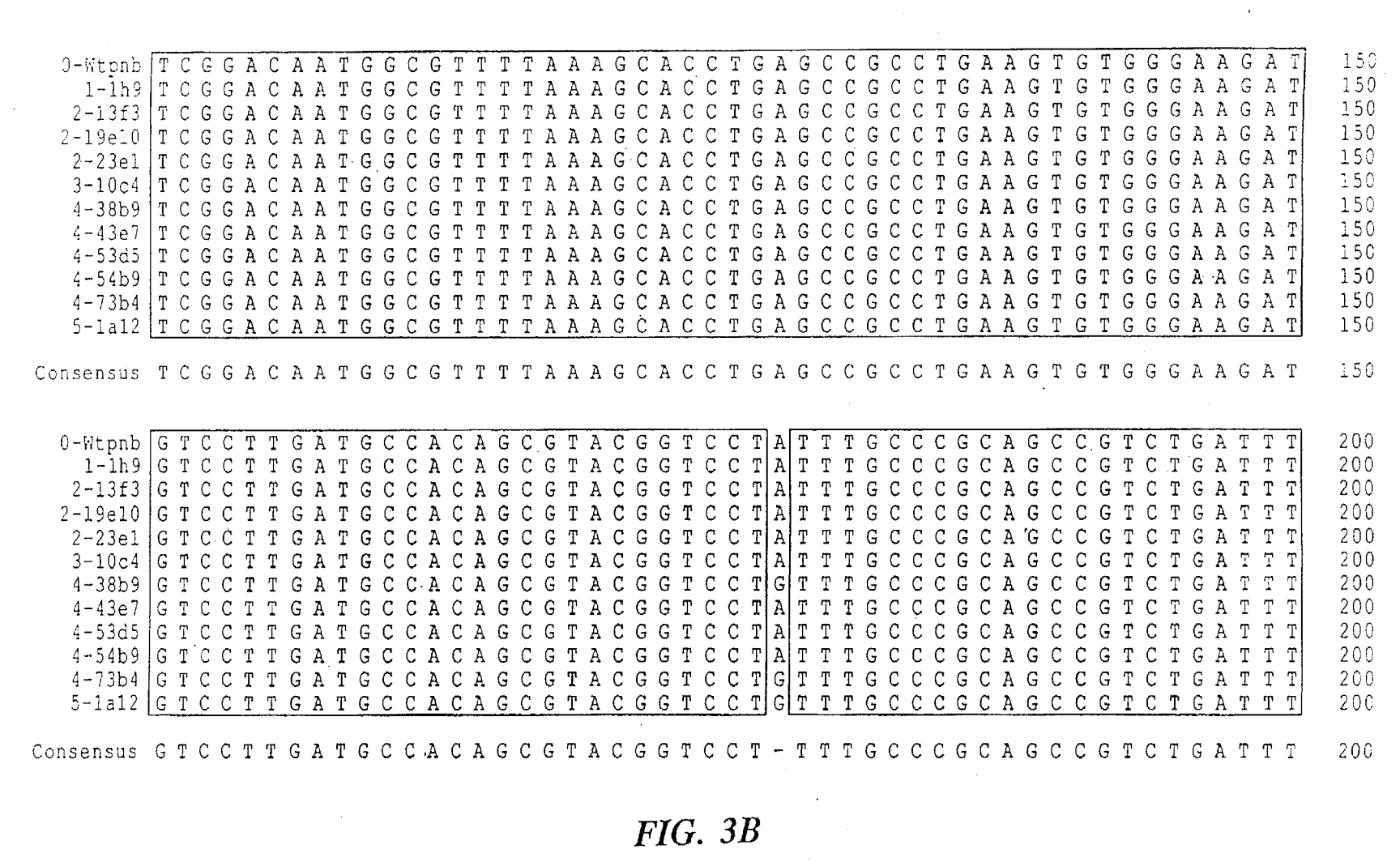
Figure 3C:
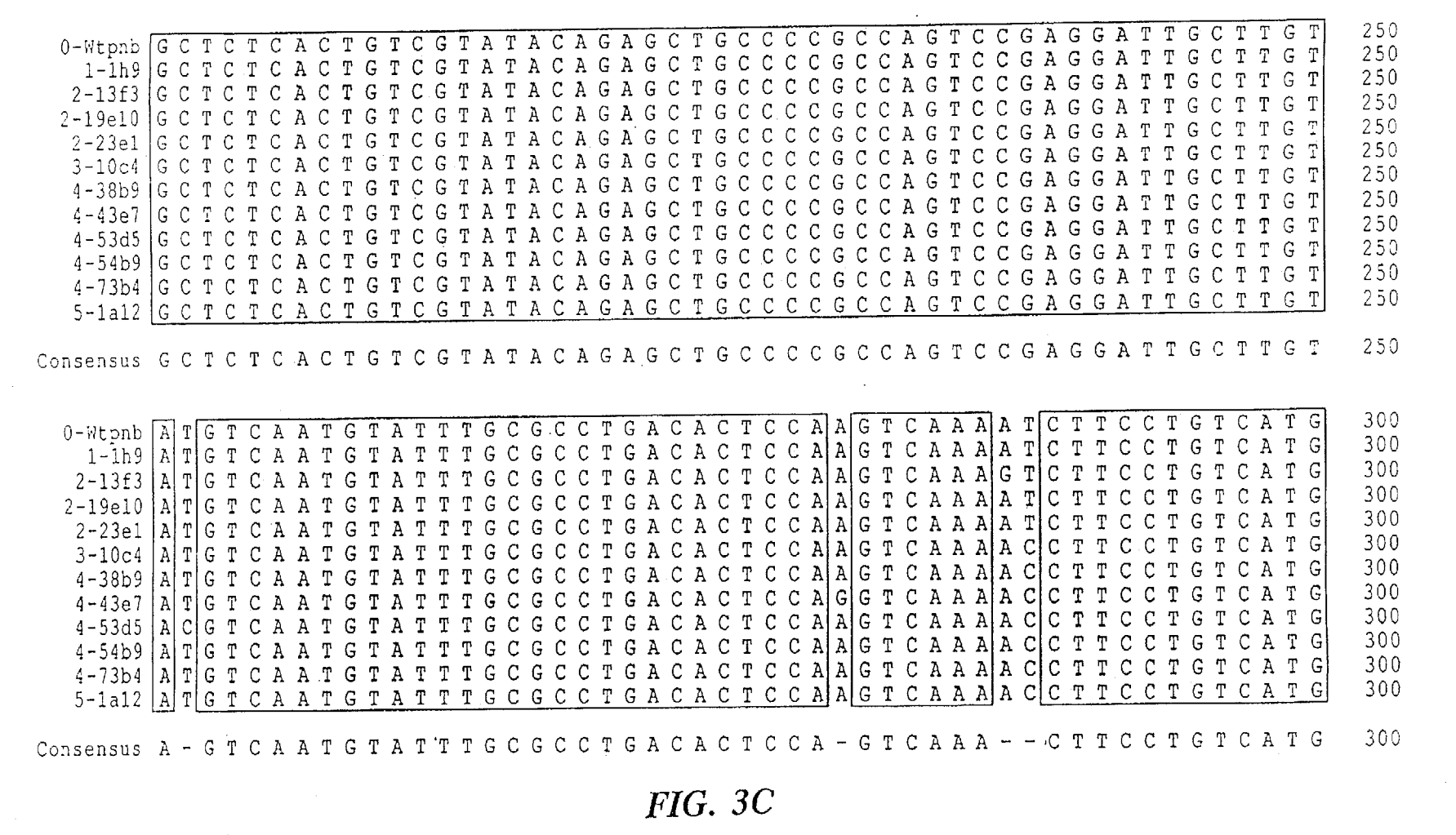
Figure 3D:
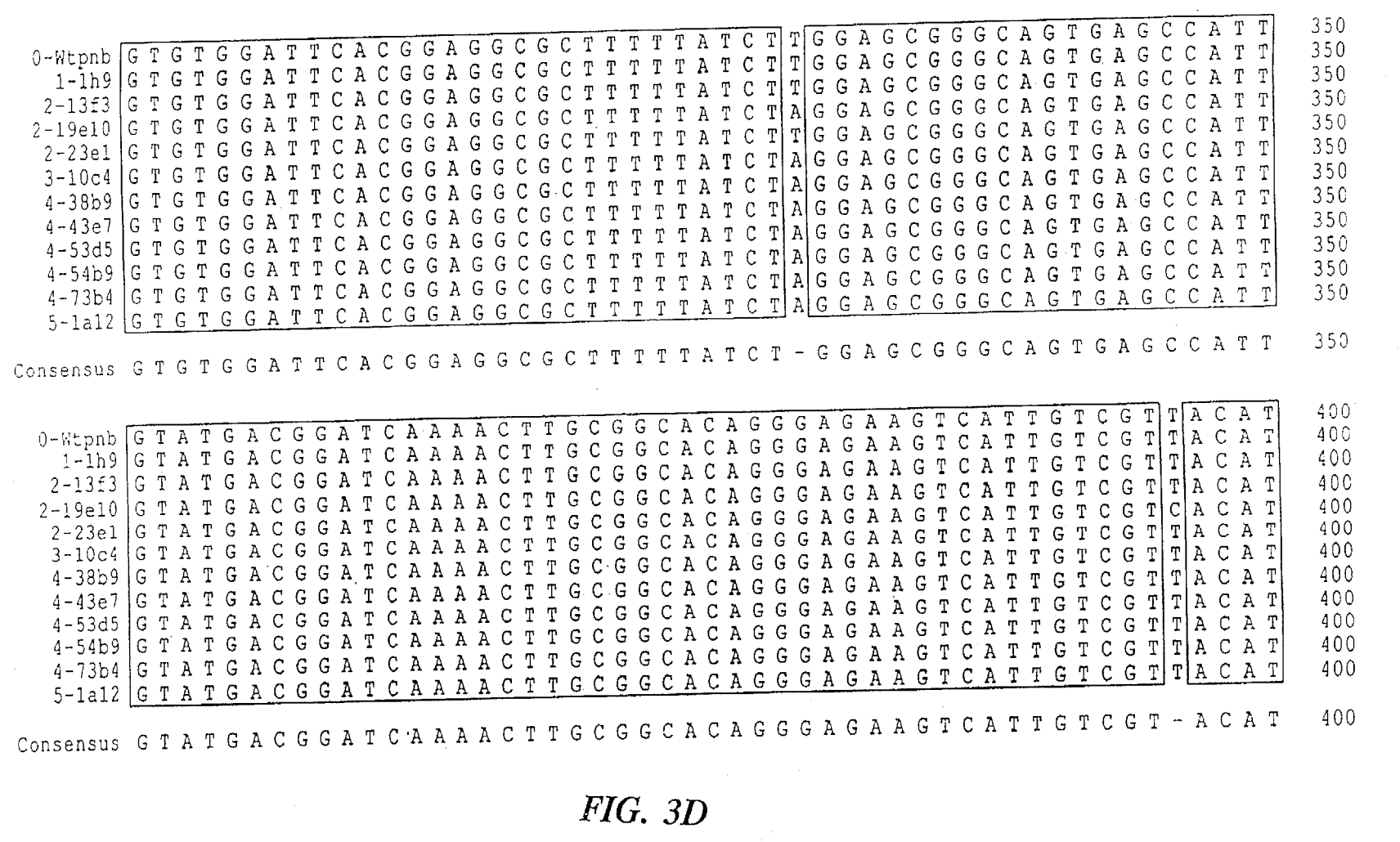
Figure 3E:
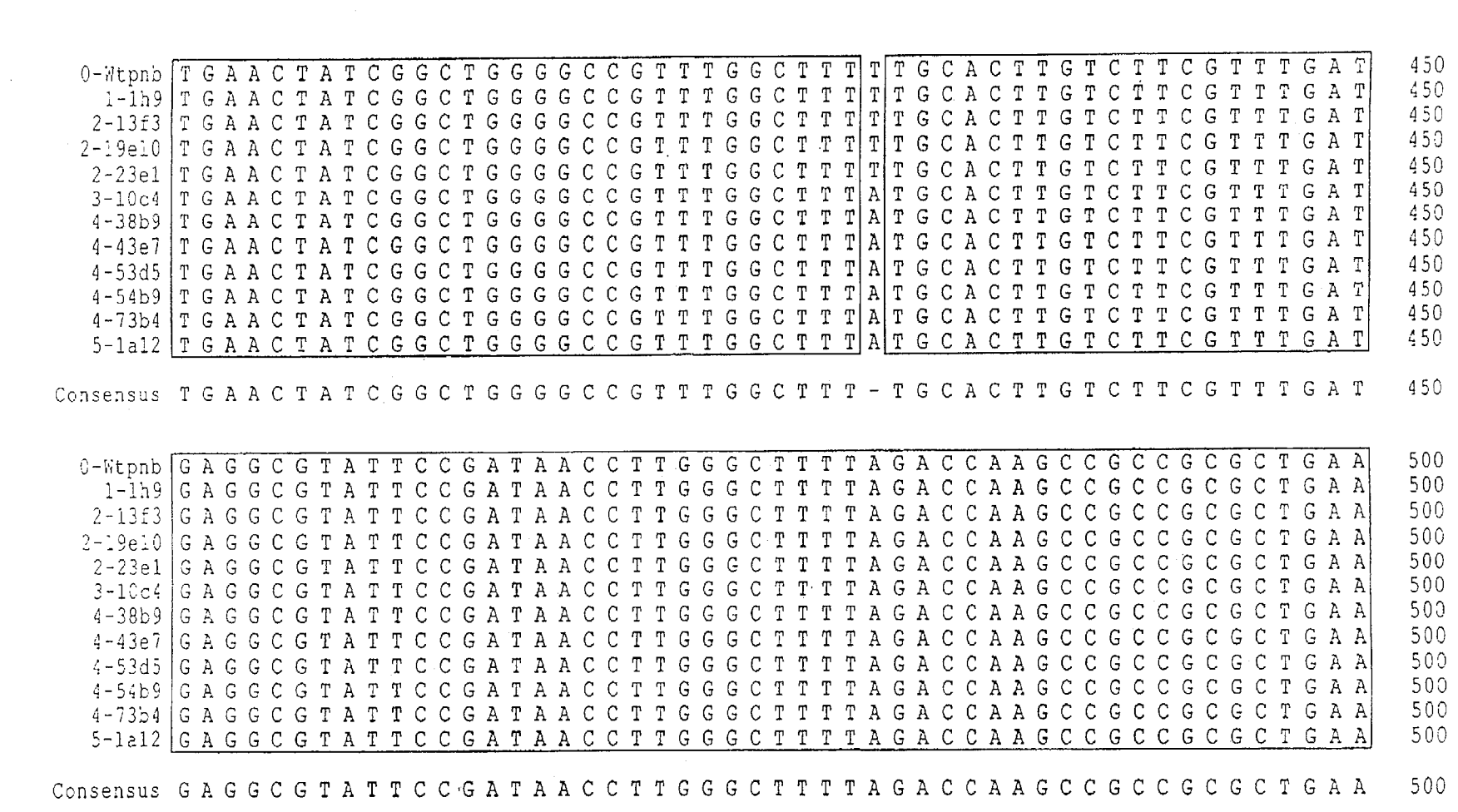
Figure 3F:
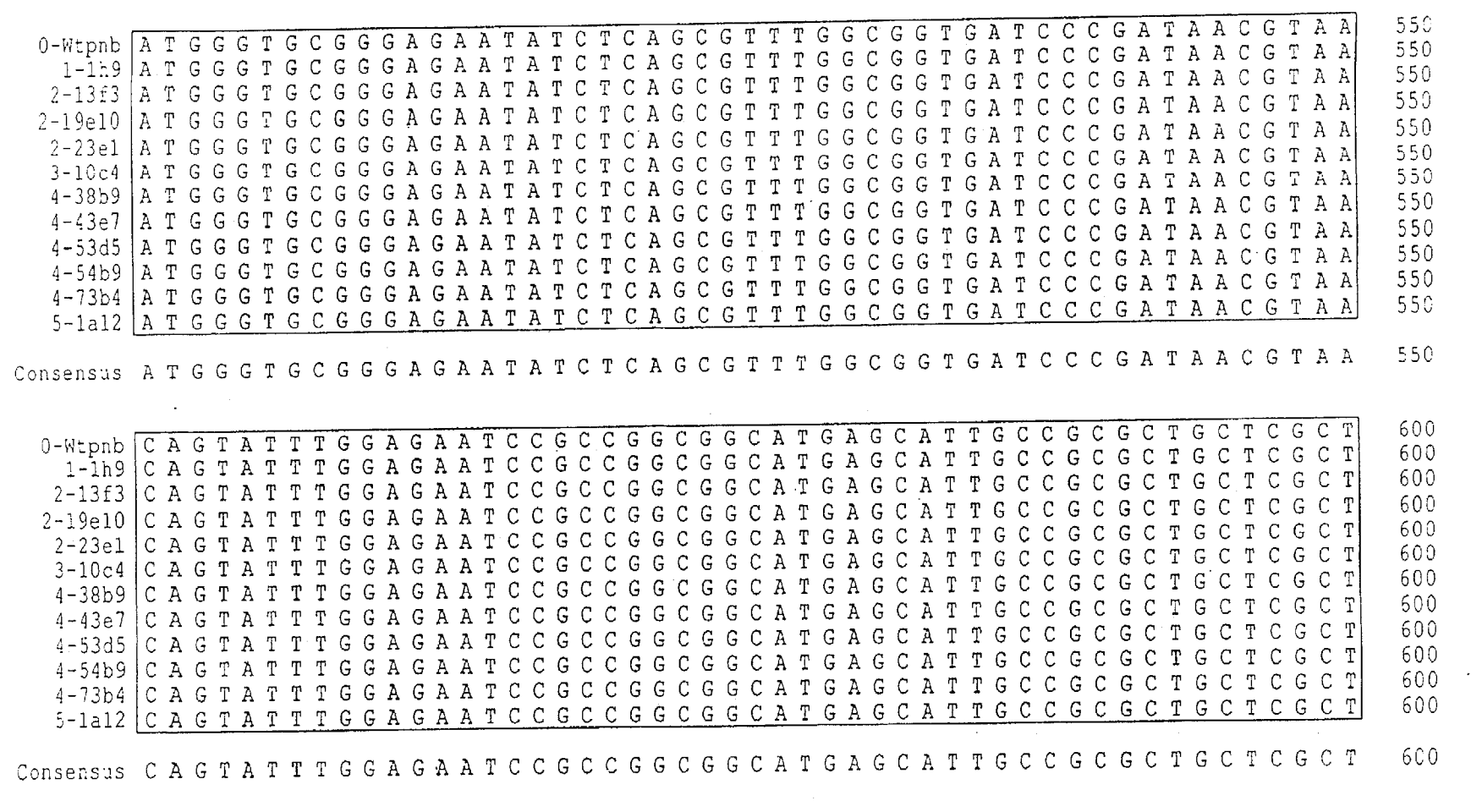
Figure 3G:
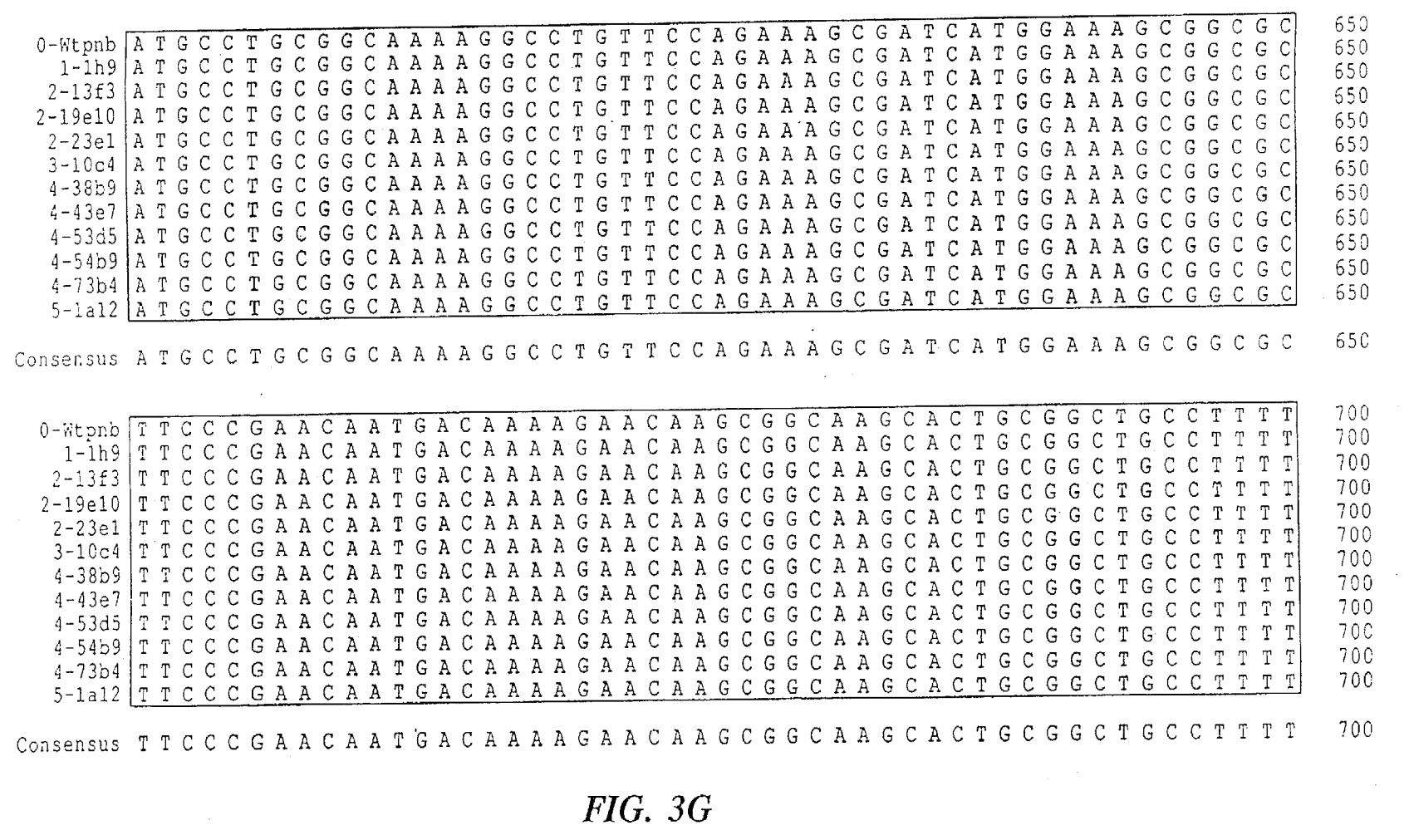
Figure 3H:
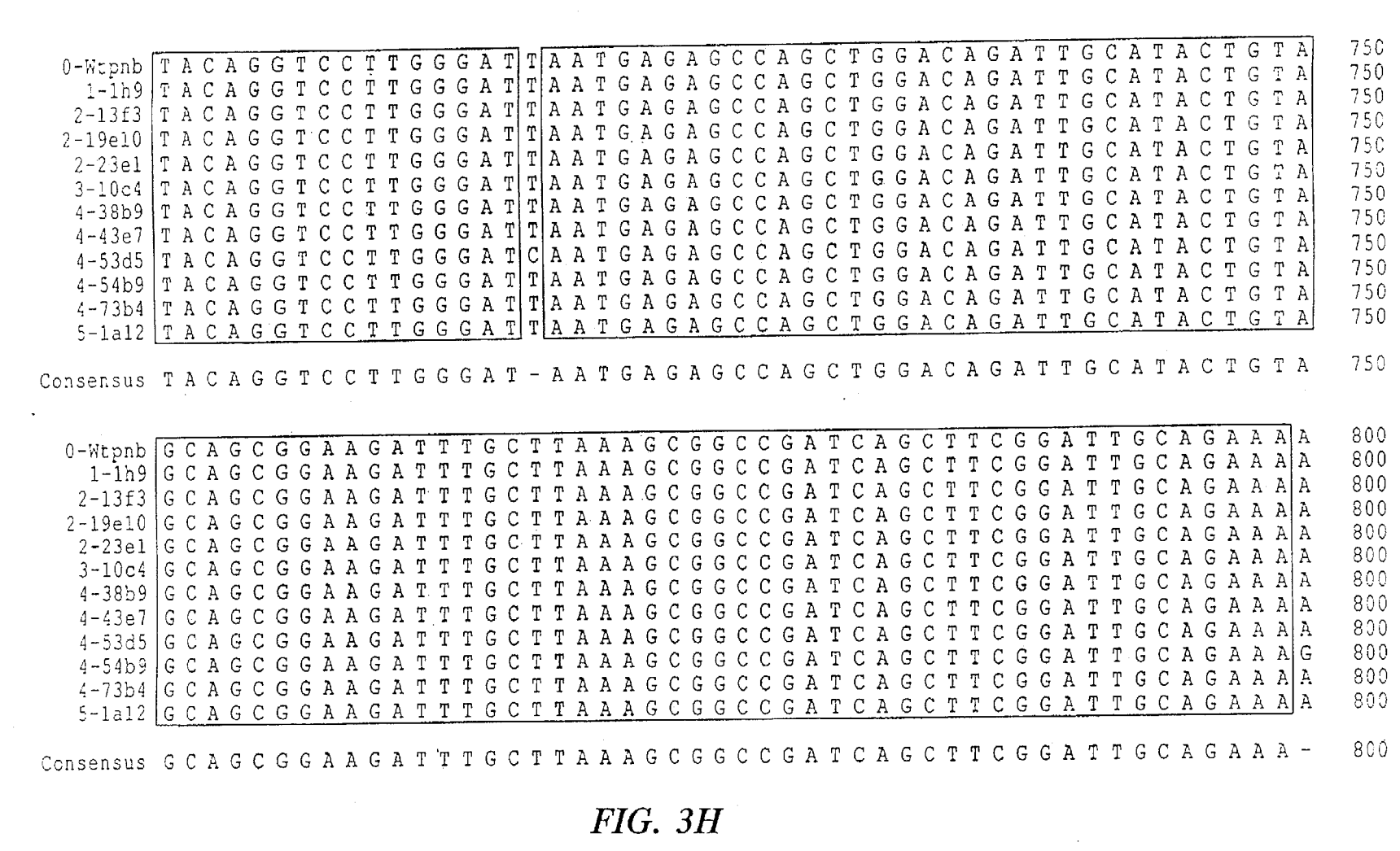
Figure 3I:
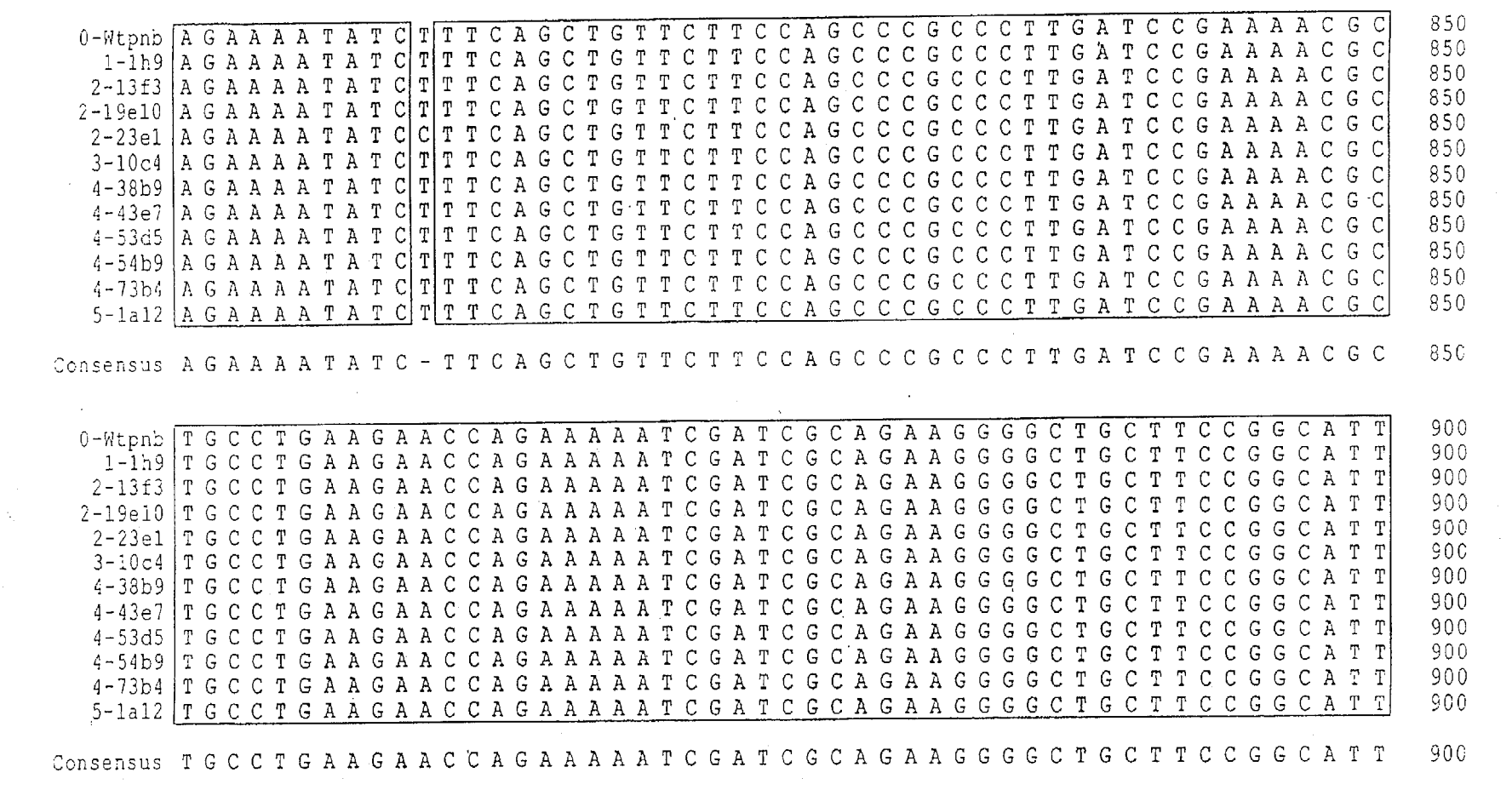
Figure 3J:
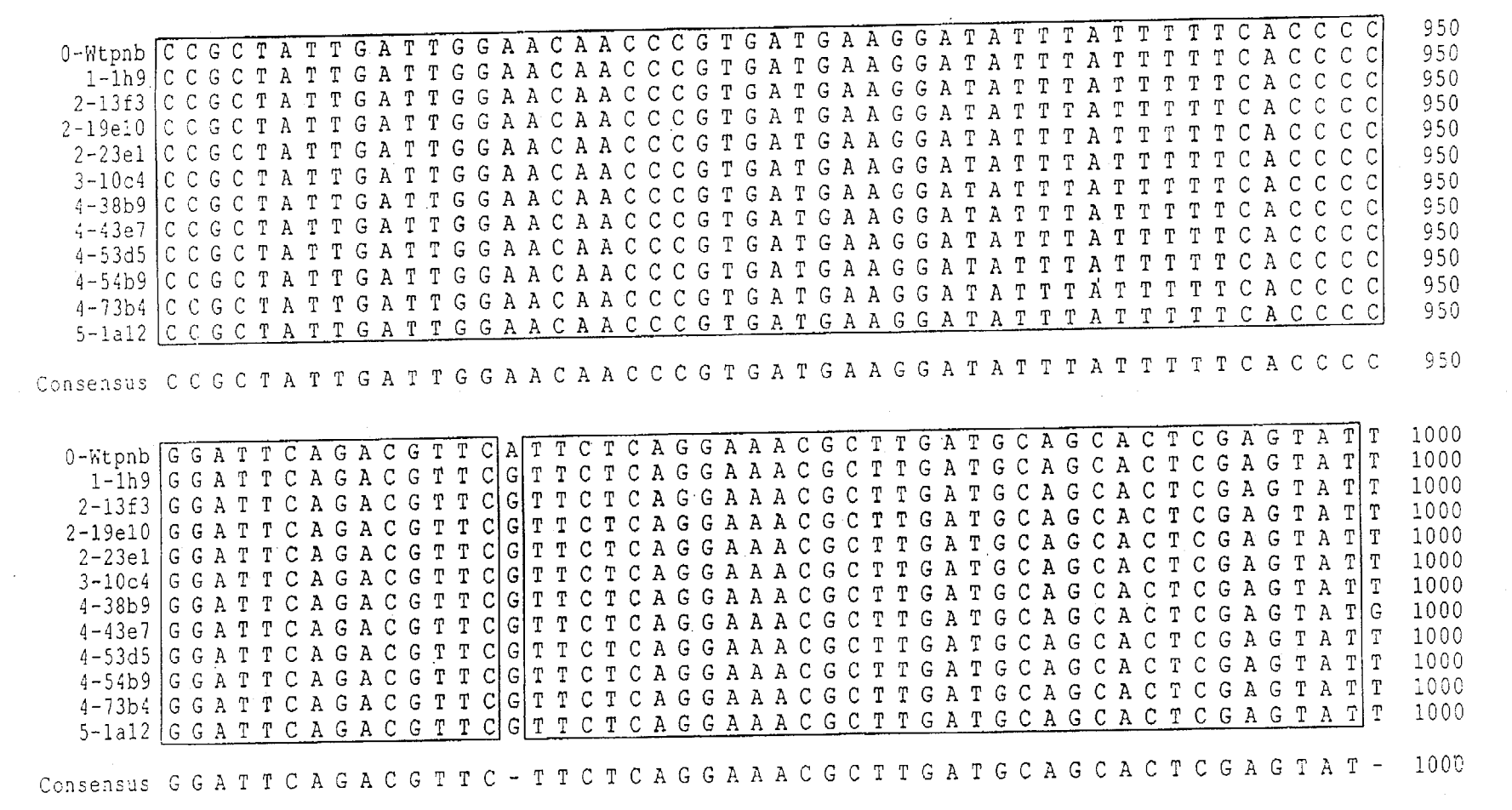
Figure 3K:
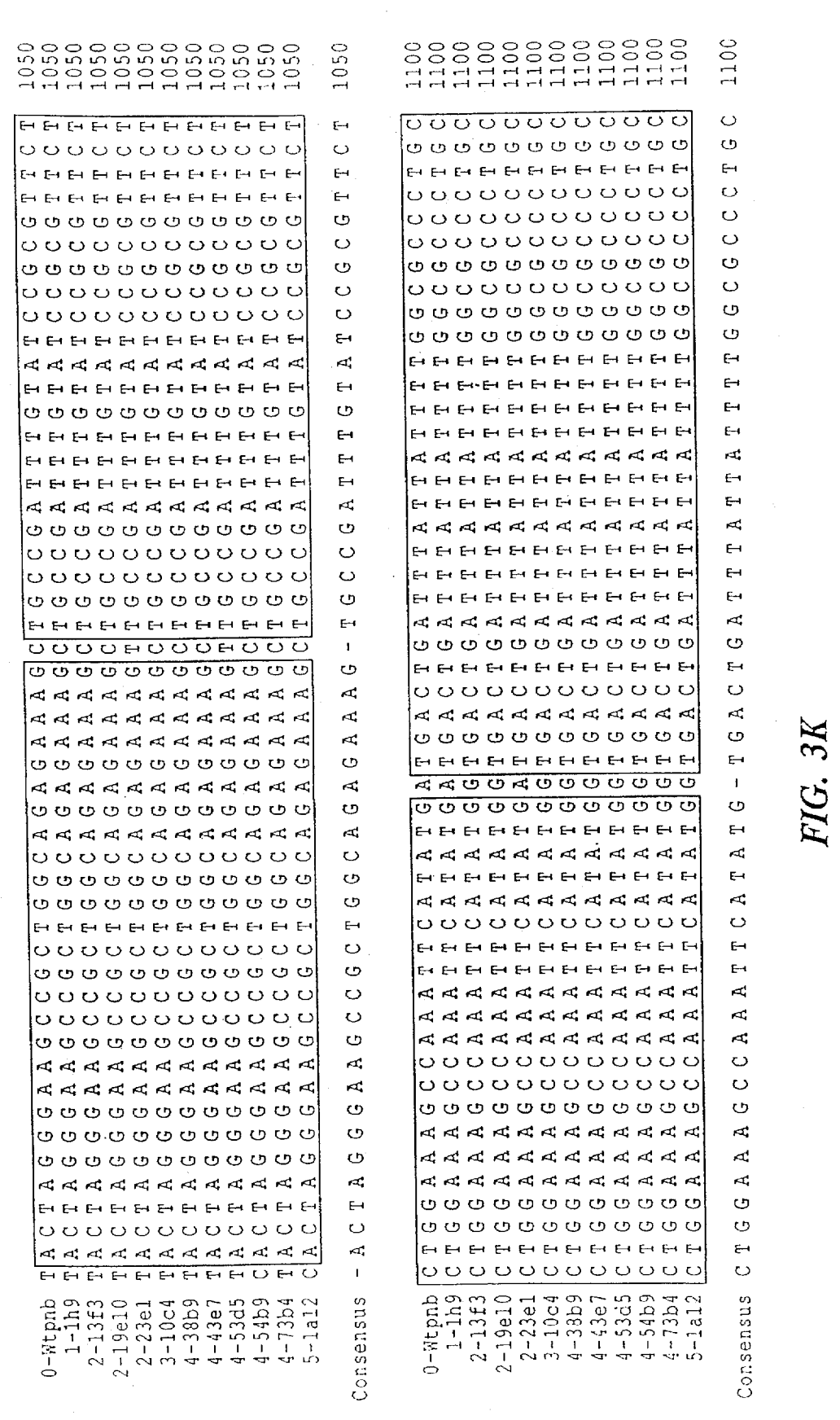
Figure 3L:
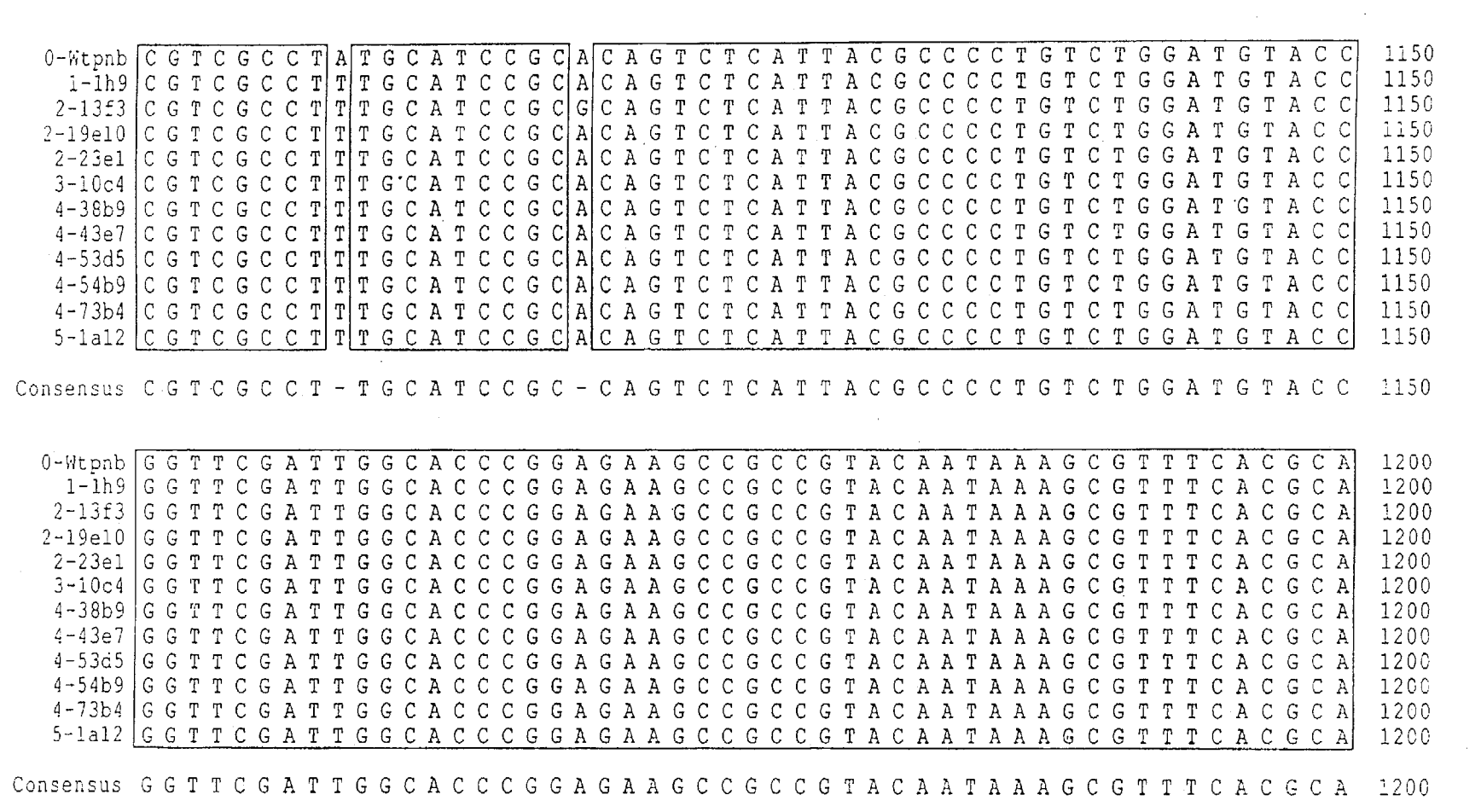
Figure 3M:
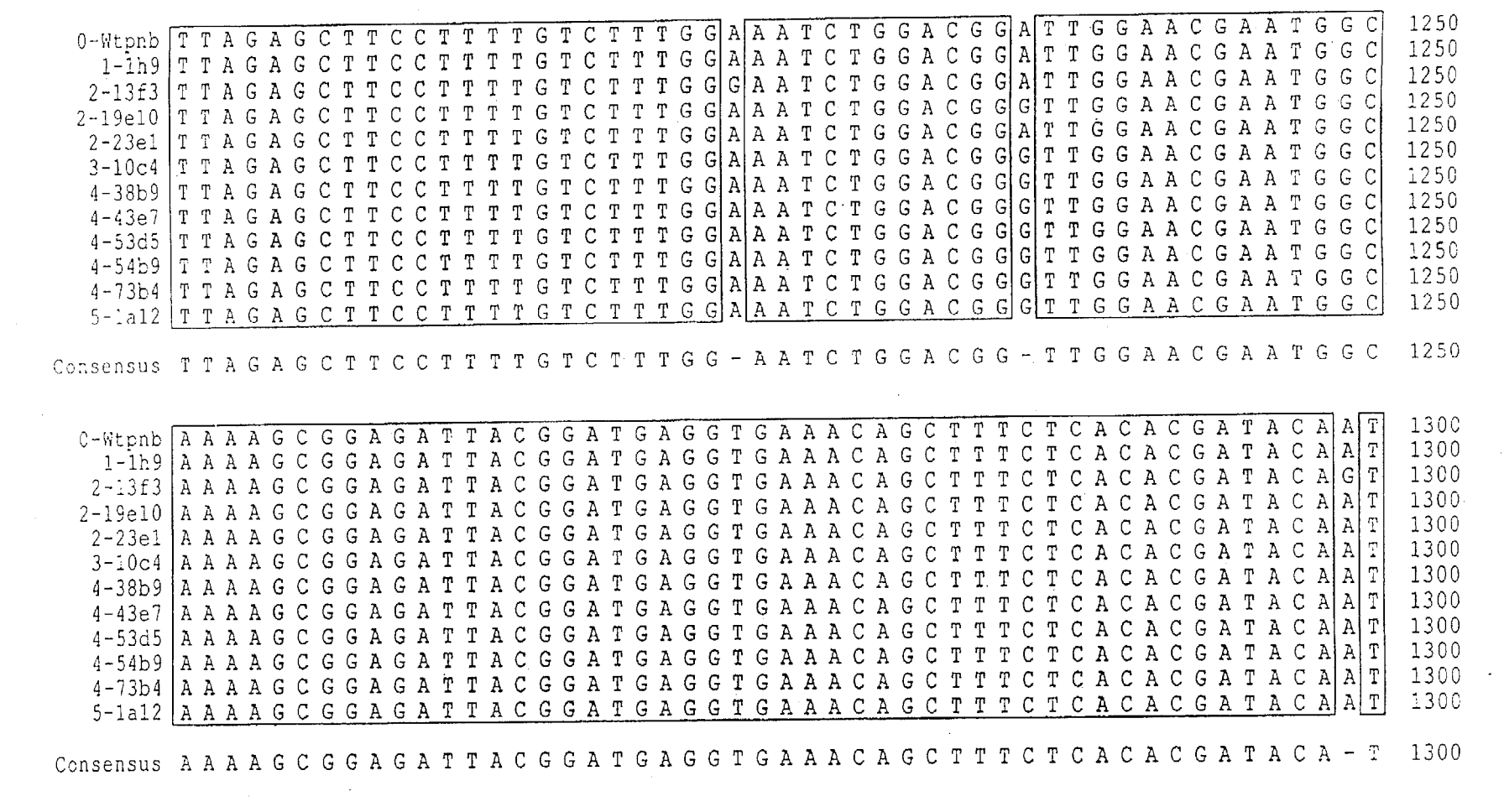
Figure 3N:
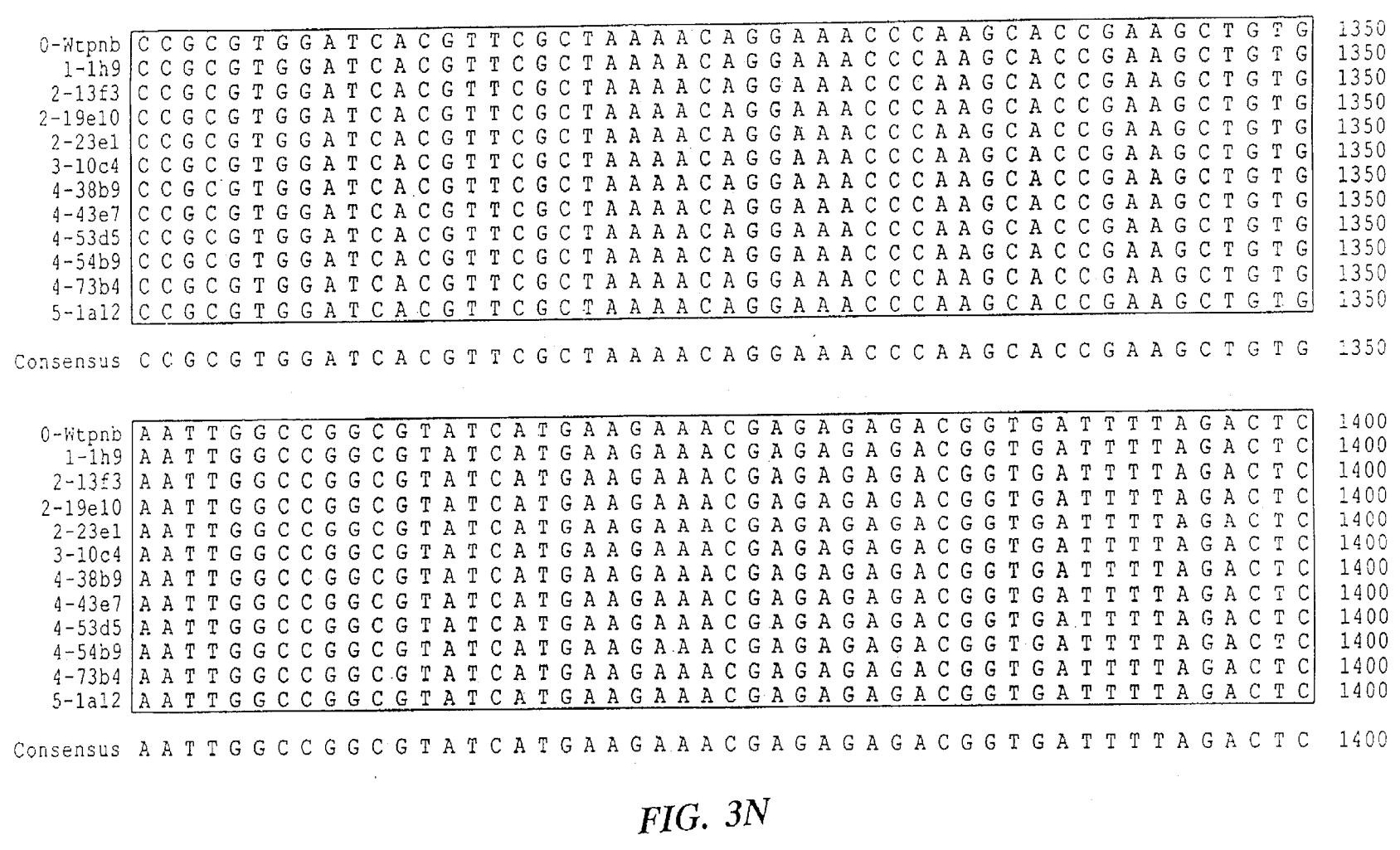

FIGS. 3a–3o show the DNA sequence alignment of enzyme variants identified in accordance with the present invention as they align with naturally occurring para-nitrobenzyl esterase (O-Wtpnb). The variants are listed from top to bottom by generation. Boxed regions indicate DNA sequence regions where all variants are identical. The columns of DNA bases not boxed are those where at least one mutation in one of the variants has occurred.

FIGS. 4a–4e are the amino acid sequence alignment of the enzyme variants. The variants are listed from top to bottom by generation. The boxed regions indicate amino acid sequence regions where the variants are all identical with naturally occurring para-nitrobenzyl esterase. The columns of amino acids not boxed are those where at least one mutation in one of the variants has occurred.

FIG. 11 shows the chemical structure of L-glutamine p-nitrobenzyl ester.

FIG. 11a–b shows graphic results of HPLC measurement of the product of variant wild type pNB esterase reaction on 1.0 mM L-glutamine p-nitrobenzyl ester in 1% dimethylformamide (DMF) after a fixed reaction time. Enzyme was added to a 25° C. reaction solution consisting of 0.1M PIPES pH 7.0, 1% (FIG. 11a) or 20% (FIG. 11b) DMF.

DETAILED DESCRIPTION OF THE INVENTION

In accordance with the present invention, a method of directed evolution is used to identify and isolate modified enzymes which have improved catalytic performance over naturally occurring para-nitrobenzyl (pNB) esterases. This technique relies on being able to screen a large number of slightly different variations of the enzyme (changes in the amino acid sequence), and then to accumulate those sequence changes. Generating the variations in a random fashion utilizes random mutagenesis, and effective mutations are accumulated in sequential generations of mutagenesis and screening for the property of interest. The serine protease subtilisin, for example, has been evolved to be almost five hundred times more active than the naturally occurring enzyme in the presence of 60% dimethylformamide (DMF) (7, 8 and 9). The present invention utilizes a related approach to identify and isolate pNB esterases which exhibit improved activity toward selected substrates, such as loracarbef-p-nitrobenzyl ester, and which exhibit improved activity under selected reaction conditions, such as in the presence of polar organic solvents.

The method in accordance with the present invention which is used to identify and isolate modified esterases having improved activity includes three basic procedures. The first procedure involves the generation of large numbers of randomly mutated esterases. The second procedure involves screening the many mutated esterases to determine which ones exhibit increased catalytic activity in selected substrates under specific reaction conditions. The third procedure involves accumulating further beneficial mutations in an 'evolved' or modified esterase. The generation of large numbers of randomly mutated esterases may be accomplished by any number of known protocols. The preferred procedure involves generating a library of modified esterase nucleic acid segments which have nucleotide sequences that differ from the nucleotide sequence of the naturally occurring or unmodified enzyme sequence. The library of mutated nucleotide sequences is then expressed in accordance with known methods for producing amino acid sequences. The procedures for random nucleic acid mutagenesis and expression of the mutated nucleic acids is described in References 7, 8, 9 and in U.S. Pat. No. 5,316,935. Many other methods for random mutagenesis and expression are known, however, and can be implemented for this purpose.

Figure 1A:
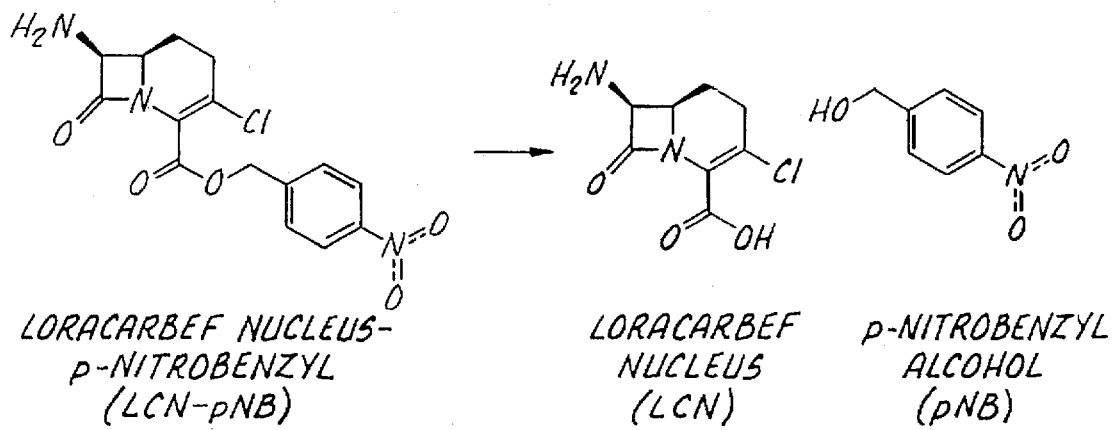
FIGS. 1a–c are diagrammatic representations of the substrates and products of reactions catalyzed by para-nitrobenzyl esterase and modifications thereof.
Figure 1B:
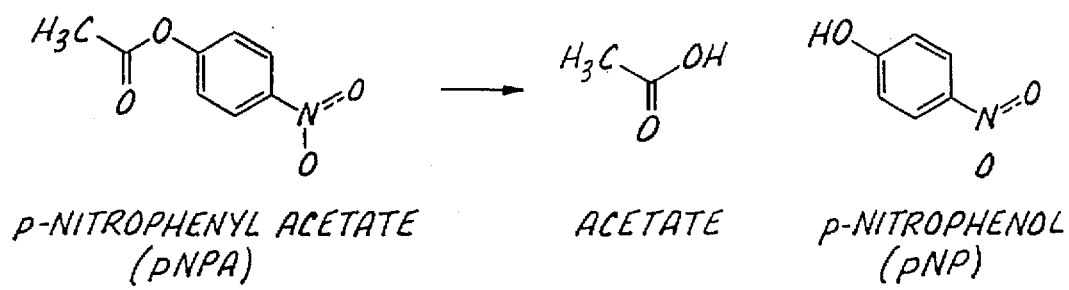
Figure 1C:
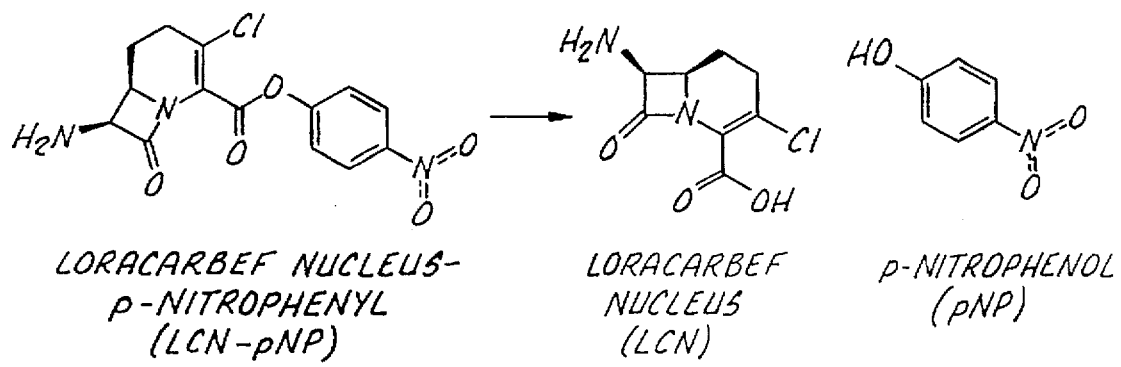

The screening of the amino acid sequences is accomplished by measuring the ability of the expressed enzymes to hydrolyze a selected substrate under selected reaction conditions. While screening can be performed directly on the desired substrate, the ease of screening can be greatly improved by using the p-nitrophenyl ester of the desired substrate. For example, if the compound of interest is loracarbef, then the p-nitrophenyl ester of the loracarbef is substituted for the p-nitrobenzyl ester (see FIG. 1c). If the sequence has the desired esterase enzyme activity, the para-nitrophenyl group will be cleaved from the substrate, as shown in FIG. 1c. The resulting free para-nitrophenol produces a yellow color in the reaction solution, which can be easily measured for both qualitative and quantitative evaluation of the amino acid sequences' performance as an esterase. This screening procedure is well-suited for evaluating the performance of modified para-nitrobenzyl esterases. This screening procedure may be used alone or in combination with the screening on the para-nitrobenzyl ester to provide confirmation of enzyme activity or to provide a more direct measurement of the ability of the amino acid sequences to catalyze p-nitrobenzyl ester cleavage for a particular compound. Other suitable nucleus compounds include other β-lactam antibiotics, peptides, peptide antibiotics (16), glycosylated peptides or amino acids (17, 18), peptides (19, 20, 21, 22, 23), natural amino acids (protected both at the C-terminus and/or acidic side chains) (21, 24, 22), non-natural amino acids (25), and other synthetic intermediates such as 2-aminobenzoate, 2-carbobenzoxyaminobenzoate (26), benzyloxycarbonyl-homoserine and benzyloxycarbonyl-O-diphenylphosphoryl-homoserine (27).

As employed herein, the term "stability," when used in reference to the stability of para-nitrobenzyl enzymes means the half-life of said enzyme when exposed to a particular set of reaction conditions, such as elevated temperature and/or organic media. In general, the higher the temperature to which the enzyme is exposed, the shorter the half-life of said enzyme (i.e., the shorter the enzyme retains its activity). Similarly, the greater levels of organic solvent to which said enzymes are exposed, the shorter the half-life of said enzyme. The phrase "catalytic activity" or simply "activity," means an increase in the $k_{cat}$ or a decrease in the KM for a given substrate, reflected in an increase in the $k_{cat}/_KM$ ratio. The above screening procedures may be conducted on a wide variety of substrates and under a wide variety of reaction conditions in order to establish the activity and/or stability of the amino acid sequences in different environments. For example, the reaction conditions can be varied from simple aqueous solutions to those containing varying amounts of organic solvents or other medium components. The amount of organic solvent or other medium components may be varied to any level. The temperature of the reaction can be varied in order to isolate variants with improved reaction rates and/or stabilities at different temperatures. Similarly, the pH of the reaction environment can be varied in order to optimize reaction rates and/or stabilities at different pH values. The reaction conditions may be varied widely in order to explore the limits of enzyme activity. The substrate can be varied in order to optimize the amino acid sequences for individual substrates or for specific combinations of substrates.

The method of the present invention was used to identify and isolate modified para-nitrobenzyl esterases which have improved ester hydrolysis activity toward several para-nitrobenzyl ester substrates in reaction solutions containing varying amounts of dimethylformamide ranging from 1 to 30 percent by volume.

The naturally occurring para-nitrobenzyl esterase has an amino acid sequence which includes numbered position ranging from 1 to 489. The amino acid sequence for this enzyme is set forth in SEQ. ID. NO. 2 and FIG. 4. The nucleotide sequence which expresses the enzyme is set forth in SEQ. ID. NO. 1 and FIG. 3. In accordance with the present invention, it was discovered that substitution of amino acids at one or more of the positions numbered 60, 94, 96, 144, 267, 271, 322, 334, 358, and 370 resulted in the production of an enzyme which exhibited increased activity toward various p-nitrobenzyl ester substrates in purely aqueous solutions and solutions containing a polar organic solvent, i.e. dimethylformamide. Any number of different amino acids may be substituted at the various identified positions with a large number of different combinations being possible where substitutions at one or more positions is accomplished. The preferred amino acid substitutions are set forth below in Table 1.

TABLE 1

| Amino Acid Position | Substitution | Abbreviation |
| --- | --- | --- |
| 60 | Ile→Val | I60V |
| 94 | Ser→Gly | S94G |
| 96 | Asn→Ser | N96S |
| 144 | Leu→Met | L144M |
| 267 | Lys→Arg | K267R |
| 271 | Phe→Leu | F271L |
| 322 | His→Arg | H322R |
| 334 | Leu→Val | L334V |
| 334 | Leu→Ser | L334S |
| 343 | Ala→Val | A343V |
| 358 | Met→Val | M358V |
| 370 | Tyr→Phe | Y370F |

Preferred modified esterases which contain one or more of the substitutions set forth in Table 1 are set forth in FIG. 4 and SEQ. ID. NOS. 4, 6, 8, 10, 12, 14, 16, 18, 20 and 22. The nucleotide sequences which expressed the preferred enzymes is set forth in FIG. 3 and SEQ. ID. NOS. 3, 5, 7, 9, 11, 13, 15, 17, 19, 21 and 23, respectively. The procedure for isolating and identifying these preferred enzymes is set forth in the examples below.

During the identification of the improved enzymes, the naturally occuring pNB esterase gene was subjected to four rounds of sequential random mutagenesis and screening to increase pNB esterase's catalytic ability toward the pNB-protected antibiotic loracarbef. Additionally, genes from positive variants isolated from the final (fourth) round were re-combined by site-specific restriction and ligation in order to combine the beneficial effects of independent mutations. By increasing the specificity towards a pNB-containing substrate and by increasing the catalytic ability in mixtures of water and non-aqueous (organic) solvent, the natural enzyme has been evolved into a number of improved enzymes which provide industrially useful tools for the deprotection of pNB esters in the amounts of organic solvents required to solubilize sufficient quantities of non-polar substrates. The above exemplary random mutagenesis and screening in accordance with the present invention are set forth in the following examples. For the purposes of this description, the reaction conditions will be limited to those which include purely aqueous or mixtures of aqueous and organic media, such as dimethylformamide (DMF). It will be understood by those of ordinary skill in the art that the method of the present invention has applications to screening enzyme activity and/or stability under a wide variety of reaction conditions and is not limited only to screening for enhanced enzyme activity in organic solvents.

EXAMPLES OF PRACTICE

Introduction

Loracarbef (LCN) is a cephalosporin-derived antibiotic marketed in modified form under the trade name LORABID. The production of loracarbef is different from many traditional antibiotics in that it is synthesized chemically with no microbial fermentation steps. This ensures that the antibiotic is free from any microbially-produced toxins generated during fermentation. While the functional antibiotic requires a free carboxylic acid moiety, the free carboxylic acid creates problems synthetically. Synthesis of loracarbef has therefore been designed to protect the carboxylic acid through an ester linkage with pNB alcohol. The pNB esterase enzyme is expected to catalyze the deprotection, that is hydrolyze the pNB ester, toward the end of the chemical synthesis. This reaction is shown in FIG. 1a. In addition to protecting the carboxylic acid, the ester-linked pNB group makes the resulting compound virtually insoluble in water.

In designing a method which directs the evolution of an enzyme towards activity and specificity on a given substrate, several important parameters require consideration. One such parameter arises from examining the frequency with which enzyme variants with enhanced performance on the desired substrate arise as a result of random mutagenesis. Nature has demonstrated repeatedly that most variations in an enzyme's amino acid sequence either do not alter the enzyme's structure or function or are deleterious. This suggests that a large number of variants need to be examined to find a variant more effective at performing the desired ester hydrolysis in FIG. 1a. A rapid procedure is required to screen large numbers of enzyme variants. Colorimetric assays are most often optimal in this regard. The reaction in FIG. 1a is problematic for rapid screening of activity because the absorbance spectra of the reactant and the two products are very similar. In addition, the reactant and products do not absorb in the visible region, making the rapid assaying of activity difficult.

Para-nitrophenyl acetate (pNPA) is a general esterase substrate. The enzyme-catalyzed hydrolysis reaction is shown in FIG. 1b. Use of the pNPA substrate solves the absorbance problem, as the nitrophenol product is yellow while the other reaction components are colorless. The ability of the alcohol oxygen to form resonance structures which participate in conjugation with the phenyl ring gives rise to the yellow color. Lowering the pH below 6.5 severely shifts the resonance structure away from the conjugation and eliminates the yellow color associated with nitrophenol solutions. The ability to form resonance structures also makes nitrophenol an excellent leaving group, as demonstrated by pNPA's gradual hydrolysis in buffer alone. This spontaneous hydrolysis accelerates with increasing pH, and at pH values above 8.5 occurs almost immediately. The pNPA substrate is also membrane permeable. This substrate is hydrolyzed rapidly by whole E. coli cells expressing pNB esterase intracellularly. The same cells, but without the expression plasmid, do not catalyze the conversion. This substrate is sterically and chemically different from the LCN-pNB substrate, however, and as such is not the most preferred choice for directing the evolution of the esterase toward activity on LCN-pNB. It does however, allow for optimization of enzyme expression in new bacterial hosts, where the increase in amount of enzyme produced translates into increased activity during screening.

In accordance with the present invention, in order to optimize generation of enzymes with improved activity toward the LCN-pNB substrate, a preferred alternate or supplemental substrate is utilized which includes the p-nitrophenyl chromophore from the pNPA substrate and as much of the loracarbef nucleus as possible. This substrate is the LCN-pNP substrate whose structure and reaction are shown in FIG. 1c. This substrate is membrane permeable, obviating the need for cell lysis during screening. The use of LCN-pNP during screening may result in an enzyme with high hydrolytic activity toward LCN-pNP, but not toward LCN-pNB. The validity of this screening approach was therefore verified by comparing the activities of nearly 70 pNB esterase variants on these two substrates.

A second parameter in directed evolution experiments is the choice of reaction conditions used during screening. The more the screening conditions differ from the desired reaction conditions, the more likely that variants found to have a positive, effect in screening will not exhibit improved performance in the desired reaction conditions. Therefore the reaction conditions used for screening should mimic as closely as possible the ultimate desired reaction conditions (temperature, pH, solvent, substrate concentration, reaction time, etc.).

Screening of Variants

The screen consisted of resuspending individual colonies of bacteria in a small volume of buffer and measuring the turbidity of the bacterial suspension using a spectrophotometer in order to estimate the cell concentration in the buffered solution. A small volume of this bacterial suspension was added to a buffered solution containing a pNP substrate, and the release of product is measured by following the formation of yellow color. The rate of product appearance was normalized to the cell concentration by the turbidity measurement. This is indicative of enzyme activity per bacterium; those colonies which generated higher activity to turbidity ratios were retested. The variant pNB esterases contained within the best clones were then purified and tested on the screening substrate (i.e. LCN-pNP) to determine the extent of improvement and on the desired pNB ester to further determine and confirm that the improvement applies to the substrate of ultimate interest.

Introduction of Random Mutations

The method of the present invention for directing the evolution of pNB esterase involves making a large library of pNB esterase genes, each with a small number of random, or nearly random, alterations in the 1500 base pair DNA sequence which codes for the pNB esterase. This collection of DNA sequences is then placed into E. coli, which translates the DNA sequences into the different amino acid sequences. Because the DNA sequence has been altered slightly, the amino acid sequence of the enzyme may be altered. The LCN-pNP and/or pNPA substrates are then used to screen out those E. coli that are producing an enzyme which appears to outperform the original. The best performer is then used to repeat this sequence of events, in multiple generations, until the desired performance goal is achieved. DNA sequence analysis of the improved enzymes provides identification of the amino acid substitutions responsible for the observed activity enhancements.

The number of random alterations introduced in the 1500 base pair sequence (substitution frequency) is a third important design parameter in directed evolution methods. If the frequency of alterations is too high, most of the enzymes produced will be inactive. If the frequency of alterations is too low, most of the DNA base substitutions produced will be an exact copy of the original DNA sequence, and the resulting enzymes will not be any different than the original. Because approximately one-third of the altered DNA sequences lead to the same amino acid sequence in a protein, the preferred number of DNA alterations per gene is greater than one. At one alteration or less per sequence, much of the DNA produced will produce exact copies of the original protein sequence, and a substantial portion of the screening effort will be spent searching through copies of the original enzyme. At more than than three alterations per sequence, on average more than two amino acid alterations per enzyme are being produced. The enzyme's activity is a function of all the alterations contained within; the activity becomes a competition between the rare alterations which are beneficial and the less rare alterations which are deleterious (7). The preferred number of alterations is therefore greater than one and not too much larger than three.

The substitution frequency is calculated as the number of substitutions made in a given sequence divided by the number of possible sites for substitution and is usually expressed as a percentage (or fractional substitution). Thus the substitution frequency required to generate one to three substitutions per gene depends on the sequence length of the DNA coding for the enzyme (or the length of the DNA sequence targeted for random mutagenesis, if smaller). Polymerase chain reaction (PCR) conditions which generate substitution rates from 0.25 to 20 substitutions per 1000 base pairs have been characterized (10, 11 and 12).

This above method, as exemplified in the following examples, can be used to direct the evolution of pNB esterase's ability to better catalyze a desired reaction. Evolution also implies accumulating improvements in activity over several generations, and this process is repeated multiple times, each time beginning with the best variant from the previous generation. A large library of genes each containing a small number DNA substitutions are generated using error-prone PCR techniques. This library is placed in E. coli, where it is translated from DNA to enzyme. The enzyme library is screened for those enzymes which outperform the original. The best new enzyme then becomes the original as the process is repeated until a desired result is achieved.

Purification of Enzymes

The purification of enzymes was accomplished by using a modification of the scheme which includes a pH precipitation, an ammonium sulfate fractionation and three chromatographic steps (6 and 4). The usual three chromatographic steps were reduced to two by replacing a dye affinity column and an ion exchange column with a single (IDA—$Cu^{2+}$) metal affinity column (IMAC). The wild type pNB esterase open reading frame contains 12 histidines, which are the amino acid residues generally responsible for retention on a metal affinity column (13). Although the surface accessibility of these histidines is unknown, the elution of pNB esterase at 4–5 mM imidazole in an imidazole gradient is consistent with one or two histidine interactions with the chromatographic support (14).

After the enzyme samples were exchanged into Tris buffer, pH 7.0, the enzyme concentrations were measured. As evidenced by SDS-PAGE, the purity of pNB esterase (estimated to be at least 95%) is not compromised by replacing the two chromatographic steps with one IMAC column. In addition to removing a chromatographic step, this replacement also conveniently removed the need for dialysis between columns, as the high salt content after the first ion exchange column does not affect the performance of the metal affinity column. Dialysis was performed only after separation on the metal affinity column.

Homology Studies

A homology search of the major protein data bases (Protein Information Resource, Swiss Protein, translated GenBank, and Protein Data Bank) revealed that pNB esterase shares significant homology with a number of known esterases. Eleven of the most homologous enzymes, representing seven distinct classes of esterases, were chosen for sequence comparisons with pNB esterase. These enzymes, their EC classification, the organism from which they were isolated, and their percent identity and similarity to pNB esterase are listed in Table 2. The enzymes were identified using a BLAST search of the PDB, PIR, SWISS-PROT, and translated GenBank databases. Percent (%) identity and % similarity were determined using the BEST-FIT tool in the GCG software package.

TABLE 2

Comparison of amino acid sequence between pNB esterase and esterases isolated from various organisms

| Enzyme | Code | Species | % Identity | % Similarity | Reference |
|---|---|---|---|---|---|
| Acetylcholinesterase | EC3.1.1.7. | Torpedo californica | 32.5 | 53.7 | 16 |
| | | Oryctolagus cuniculus | 36.0 | 58.3 | 17 |
| Butyrylcholinesterase | EC3.1.1.8. | Oryctolagus cuniculus | 35.0 | 56.7 | 18 |
| Carboxylesterase | EC3.1.1.1. | Oryctolagus cuniculus | 36.7 | 57.2 | 19 |
| | | Homo sapiens | 37.2 | 58.6 | 20 |
| | | Dictyostelium discoideum | 34.4 | 55.5 | 21 |
| Thioesterase | EC3.1.2.14. | Anas platyrhynchos | 38.7 | 58.3 | 22 |
| Thriacylglycerol lipase | EC3.1.1.3. | Geotrichum candidum | 30.4 | 48.6 | 23 |
| | | Candida rugosa | 29.1 | 49.5 | 24 |
| Cholesterol esterase | EC3.1.1.13. | Candida rugosa | 29.6 | 49.8 | 25 |
| Carbamate hydrolase | EC3.1.1.—. | Anthrobacter oxidans | 34.0 | 56.8 | 15 |

The cholinesterases are important in neurotransmission, carboxyl- and thioesterases are digestive enzymes, lipases and cholesterol esterases work on degrading lipid components. Carbamate hydrolase was discovered in the same way pNB esterase was discovered: screening for an enzyme with activity on a desired substrate, phenmedipham, an herbicide carbamate (15). Carbamates are structurally similar to esters, containing a nitrogen linkage not present in esters (R—N—COO—R' vs. R—C—COO—R'), and are known to inhibit esterases. This degradative activity was discovered in an *Arthrobacter oxidans* strain from soil samples of phenmedipham-treated fields. Starting from enzymes such as these, the method of the present invention can be used to prepare and isolate groups of modified esterases or carbamate hydrolases which have improved activity over other naturally occurring enzymes, such as those listed in Table 2.

Some of the esterases in this group of homologous enzymes are noted for the feature of substrate inhibition at high substrate concentration (26). In particular, substrate inhibition has been a well-noted feature of acetylcholinesterase analysis. While the mechanism of inhibition is not clear, people have chosen to model the inhibition using the premise that the substrate can bind at two locations within the enzyme, and do so with different binding constants (27). Butyrylcholinesterase does not share this inhibition, and this fact is often used to distinguish the two cholinesterases. Studies have determined some of the residues responsible for this behavior by altering acetylcholinesterase residues to the appropriate butyrylcholin-esterase residues and examining the inhibitory behavior (28). The fact that the inhibition characteristics can be altered by substitution shows that enzyme variants of the above types of enzymes, which are not inhibited by substrate, can be produced by the method of the present invention involving random mutagenesis and screening in high concentrations of substrate for enhanced activity.

Random Mutagenesis of pNB Esterase by Error-Prone PCR

The pNB esterase gene is flanked by the restriction site Xba I 51 base pairs prior to the start of the open reading frame and by the restriction site Bam HI 313 base pairs after the stop codon of the open reading frame (4). Small, single-stranded DNA primers were synthesized to complement regions 25 base pairs upstream of the Xba I site (forward primer) and 143 base pairs downstream of the Bam HI site (reverse primer). The locations of these primers were chosen because the DNA between the two primers is the region that will be altered and amplified during the mutagenic polymerase chain reaction (error-prone PCR). The error-prone PCR conditions used were based on the requirements that the substitution frequency be between one and three substitutions per thousand bases (1.5 to 4.5 substitutions per gene) (10). Changes in any part of the open reading frame resulting in enhanced activity are useful. Therefore the whole open reading frame was given the opportunity to be altered by the mutagenesis. Additionally, once the DNA is amplified and mutagenized, it must be inserted into a circular DNA plasmid. By cutting the amplified DNA with the restriction enzymes Xba I and Bam HI, the ends of this insert are properly prepared to ligate to the plasmid. Finally, the primers are located far enough outside of the restriction sites that the small pieces of DNA liberated when the insert is cut by Xba I and Bam HI were visible by standard gel electrophoresis techniques. This ensures that the cutting step has occurred properly, should the ligation perform poorly.

Screening and Analysis of pNB Esterase Variants

An initial round of error prone PCR was performed to produce substitutions within the pNB esterase gene. The resulting DNA product was cloned into the expression vector and expressed in *E. coli*. One thousand of the resulting colonies were screened for esterase activity on the pNPA substrate (FIG. 1B) in 20% DMF in 96 well plates (experimental details are given in Materials and Methods section below). Of the 1000 colonies selected, thirty-three were rescreened as potential positive variants. The three colonies with the highest activity to cell density (turbidity) ratio were grown, along with the wild type pNB esterase, in 1 liter cultures, and the pNB esterase variants were partially purified using the precipitation, ammonium sulfate fractionation, and a single DE-52 ion exchange column (6). These partially purified enzymes were then assayed along with wild type control for their hydrolytic activity toward the pNPA and LCN-pNB substrates.

All the variants showed higher total activity than wild type pNB esterase on the pNPA substrate, while only one, 1-1H9 (SEQ. ID. NO. 4), showed a significant increase in total activity on the targeted LCN-pNB substrate (1H9 indicates the variant designation; the initial 1—indicates round or generation number. This should be read "variant 1H9 of generation 1.") All variant designations in this specification follow this format. This variant was therefore used as the parent for the second generation of mutagenesis and screening.

Figure 5A:
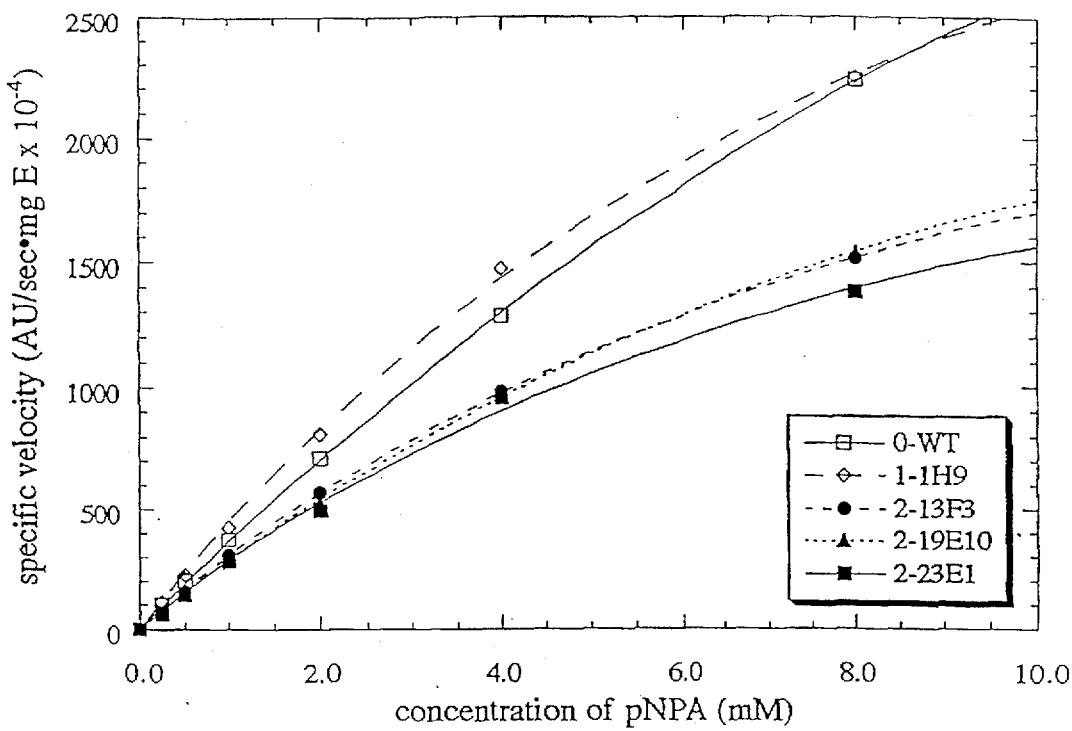
FIG. 5a shows variant and wild type pNB reaction kinetics on p-nitrophenyl acetate (pNPA) in 15% dimethylformamide (DMF). Enzymes were added to a 30° C. reaction solution consisting of 0.1M Tris-HCl pH 7.0, 15% DMF, and varying concentrations of pNPA.
Figure 5B:
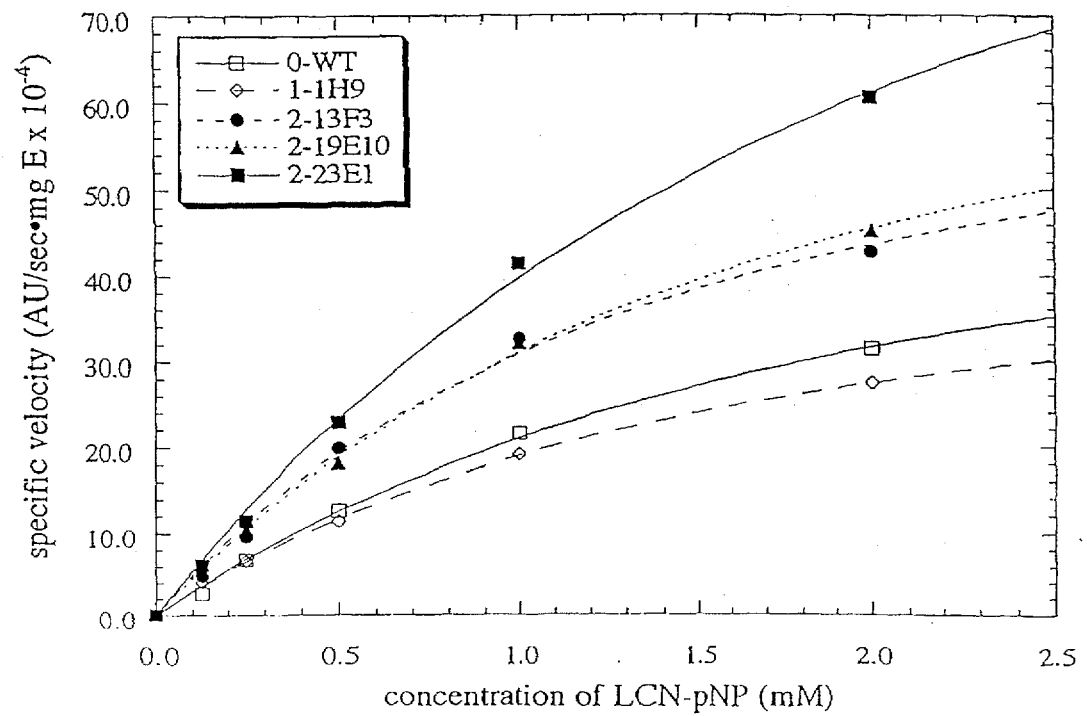
FIG. 5b is a plot of variant and wild type pNB esterase reaction kinetics on p-nitrophenyl loracarbef nucleus (LCN-pNP) in 15% dimethylformamide (DMF). Enzymes were added to a 30° C. reaction solution consisting of 0.1M Tris-HCl pH 7.0, 15% DMF, and varying concentrations of LCN-pNP.
Figure 5C:
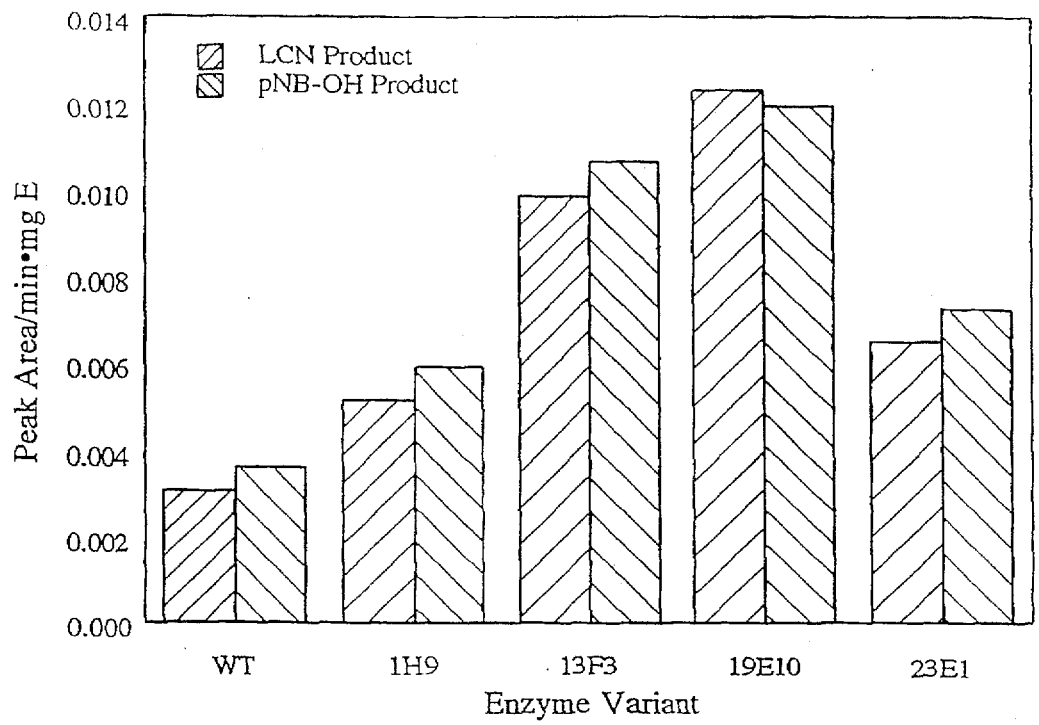
FIG. 5c shows graphic results of hydrolysis product formation, as measured by HPLC, by variant and wild type pNB esterase on 1.0 mM p-nitrobenzyl loracarbef nucleus (LCN-pNB) in 15% dimethylformamide (DMF). Enzyme were added to a 30° C. reaction solution consisting of 0.1 mM Tris-HCl pH 7.0, 15% DMF, and 1.0 mM LCN-pNB.

The second generation of the directed evolution process began with error-prone PCR on the gene isolated from variant 1-1H9. 2800 colonies were screened in 96 well plates, this time using the hybrid LCN-pNP substrate and 15% DMF. From these, 65 colonies were rescreened as potential positive variants, and again the best three were grown in 1 liter cultures along with the wild type and the 1-1H9 parent. The modified pNB esterases (2-13F3—SEQ. ID. NO. 16; 2-19E10—SEQ. ID. NO. 6; and 2-23E1—SEQ. ID. NO. 18; 1-1H9—SEQ. ID. NO. 4) and wild type—SEQ. ID. NO. 2 from these colonies were purified and assayed on all three ester substrates (pNPA, LCN-pNP, and LCN-pNB), with the results shown in FIGS. 5a, 5b and 5c. While the second round variants had lost some of their ability to hydrolyze pNPA, all three exhibited increased activity on LCN-pNP. For two second round variants, 2-13F3 and 2-19E10, the increase in activity also applied to the p-nitrobenzyl substrate, LCN-pNB. 2-23E1, the variant showing the most activity on LCN-pNP, did not show marked improvement on LCN-pNB. Because 2-19E10 showed slightly better performance characteristics on LCN-pNB, it was used for the third round of mutagenesis.

Figure 6:
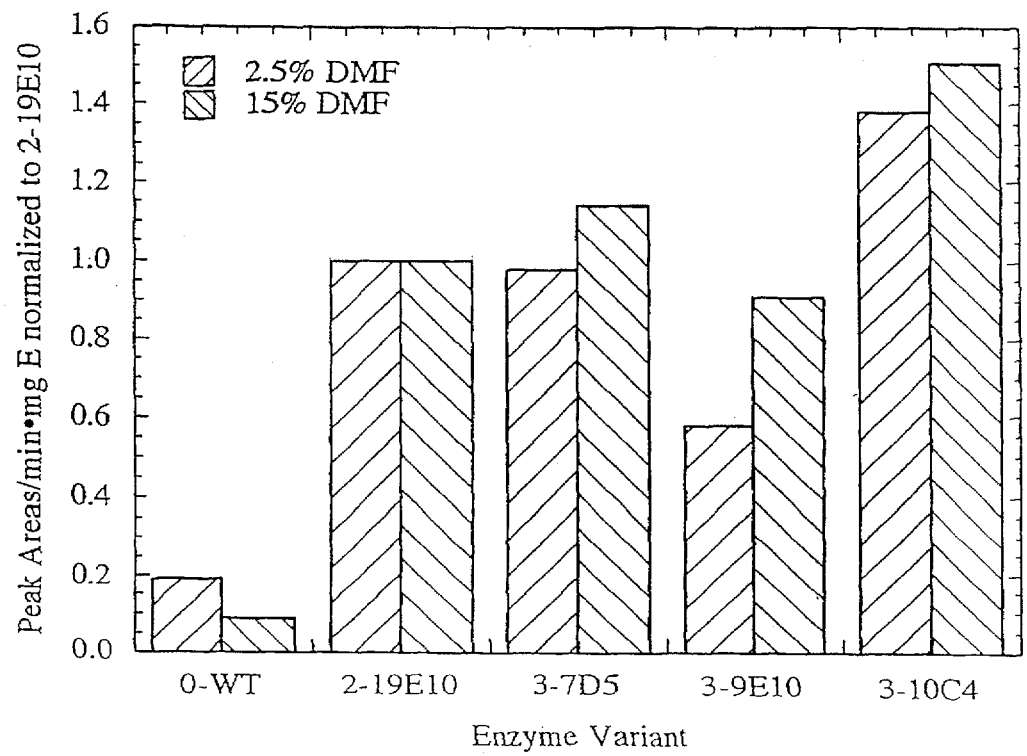
FIG. 6 shows hydrolysis product formation, as measured by HPLC, of variant and wild type pNB esterases on 0.25 mM p-nitrobenzyl loracarbef nucleus (LCN-pNB) in 2.5 and 15% dimethylformamide (DMF) at 30° C. The resulting peak areas were normalized to that of the parent of generation three, 2-19E10.

Screening of the third round of mutagenesis involved examination of 1500 colonies using the LCN-pNP substrate and 20% DMF. Forty were rescreened as potential positive variants. The three best (3-7D5, 3-9E10, and 3-10C4—SEQ. ID. NO. 8) were then grown in 500 mL cultures, and the enzymes were purified. Of these three showing best activity on LCN-pNP, only 3-10C4 showed increased activity on LCN-pNB as demonstrated in FIG. 6. 3-10C4 shows a 40% improvement in activity over 2-19E10 in 2.5% DMF and a 50% improvement in 15% DMF.

Figure 7A:
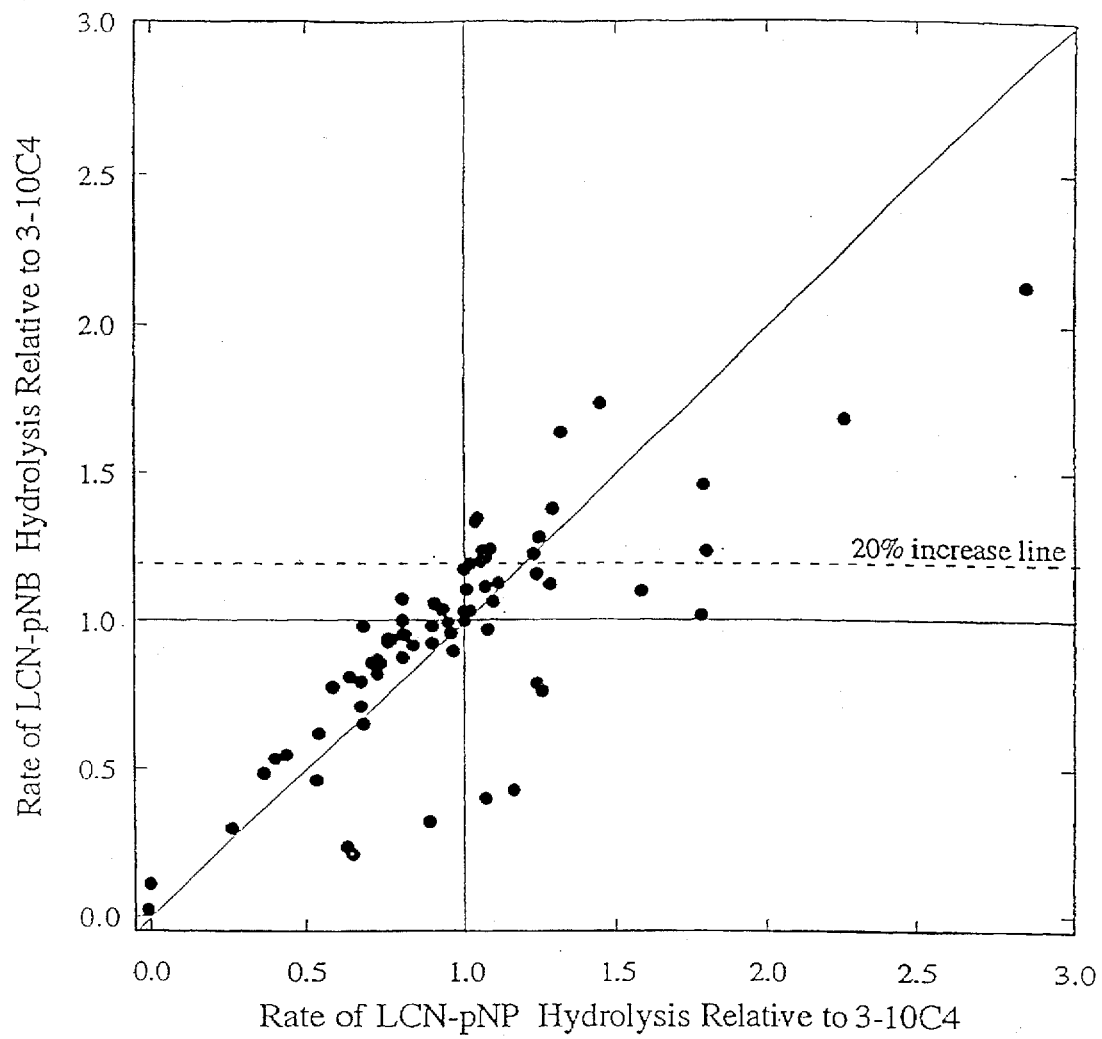
FIG. 7a is a plot of hydrolysis rates of fourth generation variants on the LCN-pNP and LCN-pNB substrates. The rates are normalized to those of the third generation variant 3-10C4. After an 8 hour induction period, whole cell screening assays were performed at 25° C. in a 0.1 mM Tris-HCl pH 7.0, 15% dimethylformamide reaction solution containing 0.8 mM of either p-nitrophenyl loracarbef nucleus (LCN-pNP) or p-nitrobenzyl loracarbef nucleus (LCN-pNB).

The fourth round of mutagenesis and screening examined 7400 colonies using LCN-pNP substrate and 20% DMF. Of these, 250 were rescreened as potential positives. Sixty-four of those either most active in 5% DMF, most active in 20% DMF, or the best ratio of activities in 20% to 5% DMF were further screened along with wild type, 1-1H9, 2-19E10, and 3-10C4 on LCN-pNB. The screening results on both LCN-pNP and LCN-pNB were normalized to the activity of the parent 3-10C4 and are shown in FIG. 7a. Of the sixty-four colonies chosen, five show activity increases of 50% or more over 3-10C4, and sixteen show increases of greater than 20% over 3-10C4. The best five variants were determined based on the ability to hydrolyze the substrate LCN-pNB only. The best variant, with over a 2-fold improvement on 3-10C4, was 4-54B9 (SEQ. ID. NO. 14). The remaining four variants all demonstrated approximately 60–65% improvement over 3-10C4; these variants were labeled 4-38B9 (SEQ. ID. NO. 10), 4-43E7 (SEQ. ID. NO. 12), 4-53D5 (SEQ. ID. NO. 20) and 4-73B4 (later found to be identical to 4-38B9.

A measure of how well the activity of these enzymes on the screening pNP substrate relates to activity on the pNB substrate was established (FIG. 7a). The overall trend demonstrates a good correlation between activities on the screening pNP and actual pNB substrates, although the distribution is skewed slightly toward the screening substrate, as demonstrated by the trend of data points to lie below the forty-five degree line. If increases in activity on one substrate correlated exactly with increases in activity on the other, then all the points would lie exactly on the 45-degree line. The strength of this correlation is an important measure of the validity of the screening strategy in accordance with the present invention. This graph shows that the screening strategy premise that the structurally similar LCN-pNP can successfully replace LCN-pNB, the hydrolysis of which is difficult to measure. Contrast this with the pNPA substrate, whose structure does not mimic the desired loracarbef substrate. Modified pNB esterase activities on pNPA do not correlate as well with activity on the loracarbef substrates.

Figure 7B:
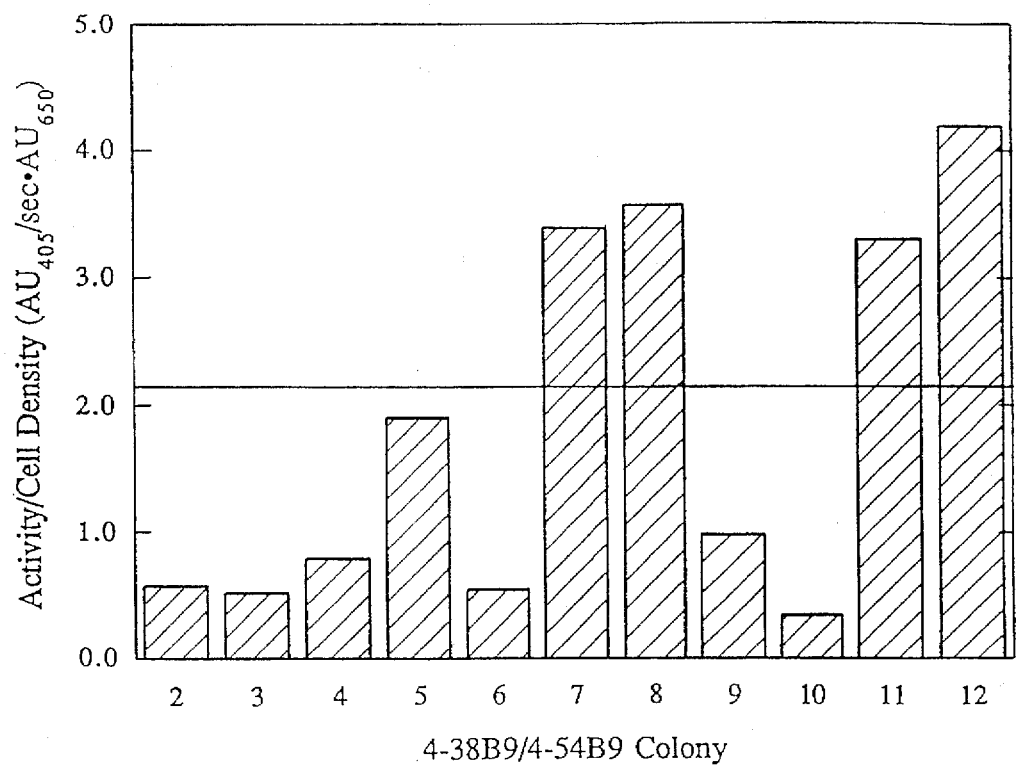
FIG. 7b is graphic results of the screening activity of ligation mixture 4-38B9 and 4-54B9. The horizontal line indicates the activity of the most active fourth round variant, 4-54B9. Colony 12, which exhibits an approximate 2-fold improvement in activity, corresponds to pNB esterase variant 5-1A12.

To demonstrate the utility of recombining beneficial mutations in the production of improved pNB esterases, a small, biased library of fifth generation variants was generated by recombining the genes from the fourth generation variants by restriction and re-ligation. The genes from the five variants from the fourth generation were individually restricted by Xho I, a restriction enzyme which cuts in the center of this gene. The DNA fragments were mixed with the DNA fragments from 4-54B9, the variant which appeared to outperform all others from the fourth generation, in pairwise fashion (e.g. one tube contained the fragments from 4-38B9 and 4-54B9, another tube contained fragments from 4-43E7 and 4-54B9, etc.). These mixtures of DNA fragments were each ligated simultaneously with the expression plasmid, transformed into E. coli, and assayed on LCN-pNP substrate in 20% DMF. The results from screening colonies expressing the recombined genes are shown in FIG. 7b. Of the four sets of ligations performed, only the mixture ligating 4-54B9 with 4-38B9 resulted in an enhancement in activity over 4-54B9. According to the screening data, this combination of mutations (labeled 5-1A12—SEQ. ID. NO. 22) displays approximately twice the activity of 4-54B9. This demonstrates that positive mutations can be combined for additional beneficial effects. Further beneficial combinations of mutations can be found by combining mutations using this or other random DNA recombination methods or by site-directed mutagenesis, once the DNA sequences are determined.

Kinetic Characterization of Evolved pNB Esterases

Figure 8A:
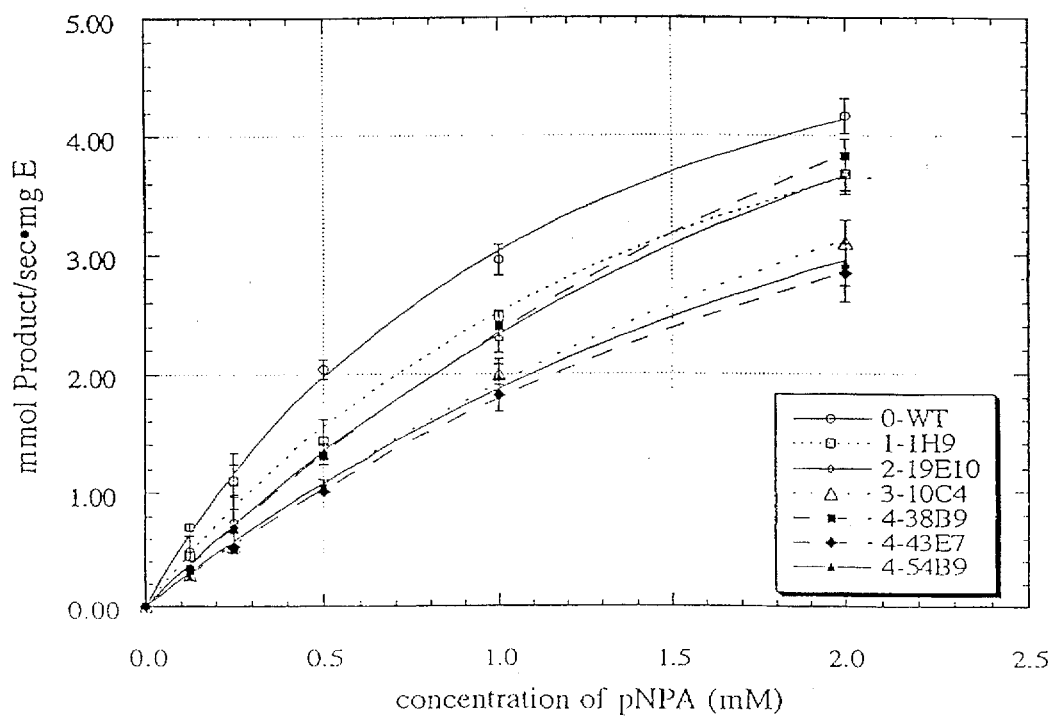
FIG. 8a is a plot of variant and wild type pNB esterase reaction kinetics on p-nitrophenyl acetate (pNPA) in aqueous buffer (0% dimethylformamide). Enzymes were added to a 30° C. reaction solution consisting of 0.1M PIPES pH 7.0 and varying concentrations of pNPA.
Figure 8B:
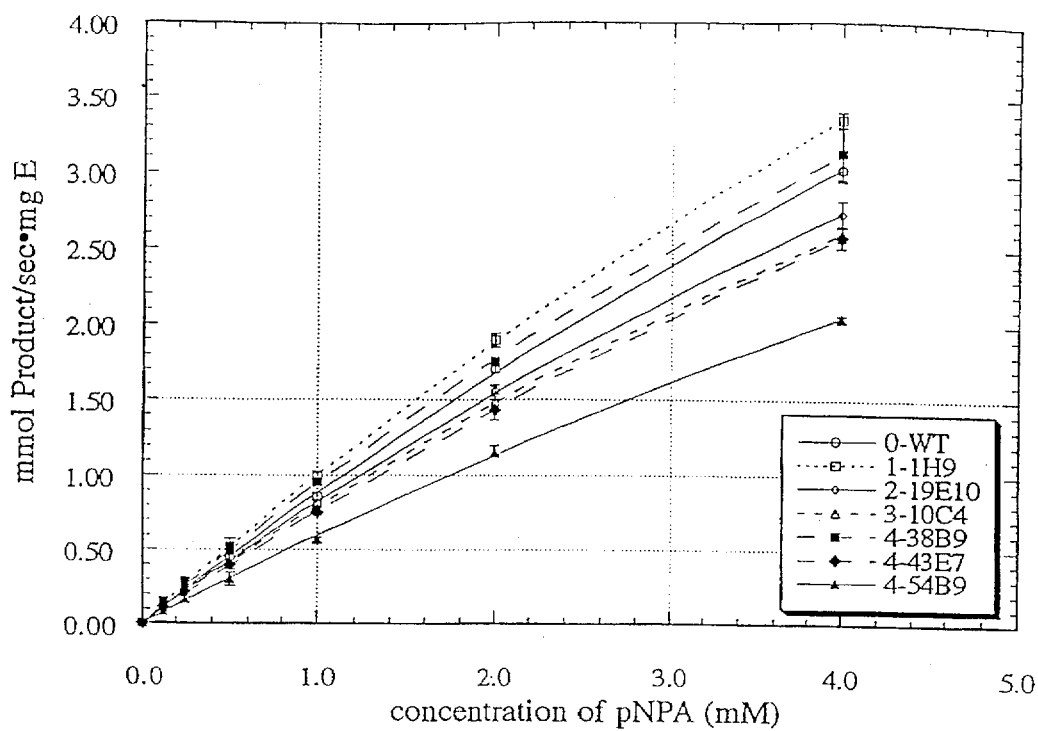
FIG. 8b is a plot of variant and wild type pNB esterase reaction kinetics on p-nitrophenyl acetate (pNPA) in 15% dimethylformamide (DMF). Enzymes were added to a 30° C. reaction solution consisting of 0.1M PIPES pH 7.0, 15% DMF, and varying concentrations of pNPA.
Figure 8C:
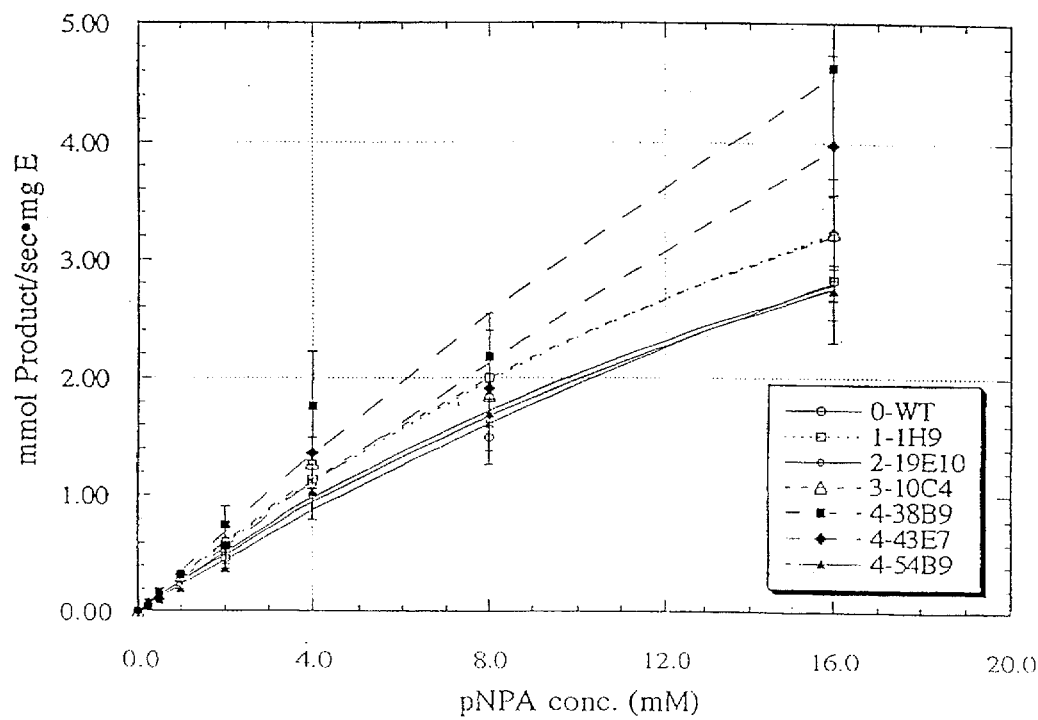
FIG. 8c is a plot of variant and wild type pNB esterase reaction kinetics on p-nitrophenyl acetate (pNPA) in 30% dimethylformamide (DMF). Enzyme were added to a 30° C. reaction solution consisting of 0.1M PIPES pH 7.0, 30% DMF, and varying concentrations of pNPA.

Bacteria expressing seven pNB esterases, O-WT (SEQ. ID. NO. 2), 1-1H9, 2-19E10, 3-10C4, 4-38B9, 4-43E7, and 4-54B9, were grown in one liter cultures, and the enzymes were purified. These purified enzymes were assayed for their ability to hydrolyze the different ester substrates in the presence of various concentrations of DMF. FIGS. 8a, b and c show the specific reaction rates on pNPA as a function of pNPA substrate concentration for this series of evolved variants from the four generations of mutagenesis and screening. Only 1-1H9 was chosen based on its performance on this substrate, and these assays performed on purified enzyme suggest that the majority of improvement in activity demonstrated by this variant during screening is due to an approximate four-fold increase in amount of enzyme produced. The wild type enzyme outperforms 1-1H9 in purely aqueous buffer (FIG. 8a). The actual screening, however, was performed in the presence of DMF, and in 15 and 30% DMF, 1-1H9 has higher specific activity towards pNPA than wild type (FIGS. 8b and 8c). Similar trends are seen for the remaining variants assayed on this substrate. Wild type is the most active enzyme in the absence of DMF, but is only average among the variants in 15% DMF. In 30% DMF, wild type drops still further relative to the pNB esterase variants. Variants 4-38B9 and 4-43E7, presumably by virtue of having been screened in DMF for four rounds of mutagenesis, are the best performers in 30% DMF.

Figure 9A:
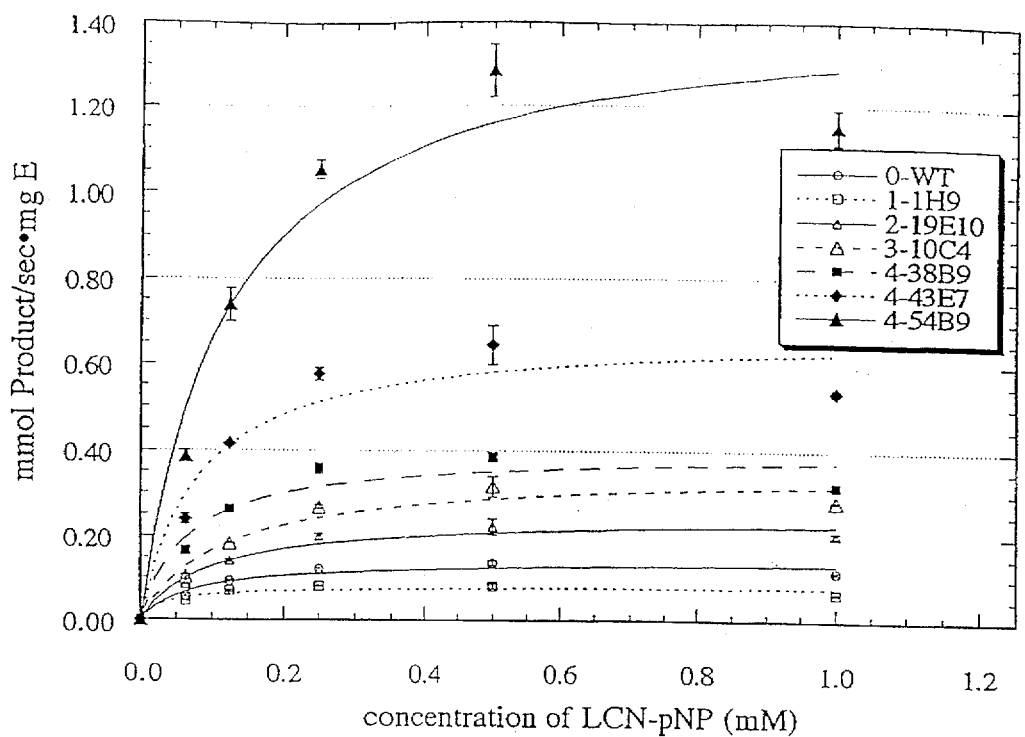
FIG. 9a is a plot of variant wild type pNB esterase kinetics on p-nitrophenyl loracarbef nucleus (LCN-pNP) in 1% dimethylformamide (DMF). Enzymes listed were added to a 30° C. reaction solution consisting of 0.1M PIPES pH 7.0, 1% DMF, and varying concentrations of LCN-pNP.

FIGS. 9a, b and c show the results of similar kinetic analyses performed using the LCN-pNP substrate with which three out of the four rounds of screening were carried out. In these plots the results of directed evolution are clearly seen. In 1, 15, and 30% DMF concentrations (FIGS. 9a, 9b, and 9c), the two variants least active on this substrate are the wild type enzyme and 1-1H9. This is not surprising given that neither of these enzymes had been screened on this substrate. Additionally, as the concentration of DMF increases, the activity of 1-1H9 increases with respect to wild type, so that in 30% DMF (FIG. 9c) enzymes display identical kinetics. The next enzyme from the bottom is 2-19E10 from the second generation of mutagenesis and screening. This variant increases the maximum reaction rate by a factor of two over wild type and three over its parent 1-1H9 at low percentages of DMF. The activity increase is sensitive to the presence of DMF, decreasing to a smaller improvement in 30% DMF. This trend continues with the 3-10C4 variant, which is 50% faster at producing product than its 2-19E10 parent in 1% DMF. 3-10C4 does not lose activity as rapidly as its parent in DMF and is 100% faster than 2-19E10 in 30% DMF. 3-10C4 is the parent of the remaining variants, all of which show enhanced activity. 4-38B9 shows the least amount of improvement, with a 20% increase in activity in 1% DMF. This increase in activity is enhanced in DMF to 50% in 30% DMF. 4-43E7 shows a constant two-fold increase in activity across all DMF ranges, and 4-54B9 is the most active of all the variants with a constant four-fold increase in activity over its parent. It is approximately 16 times more active than wild type pNB esterase. By comparing the scales of the axes, 4-54B9 retains the same activity in 30% DMF as the wild-type enzyme in 1% DMF.

Figure 10A:
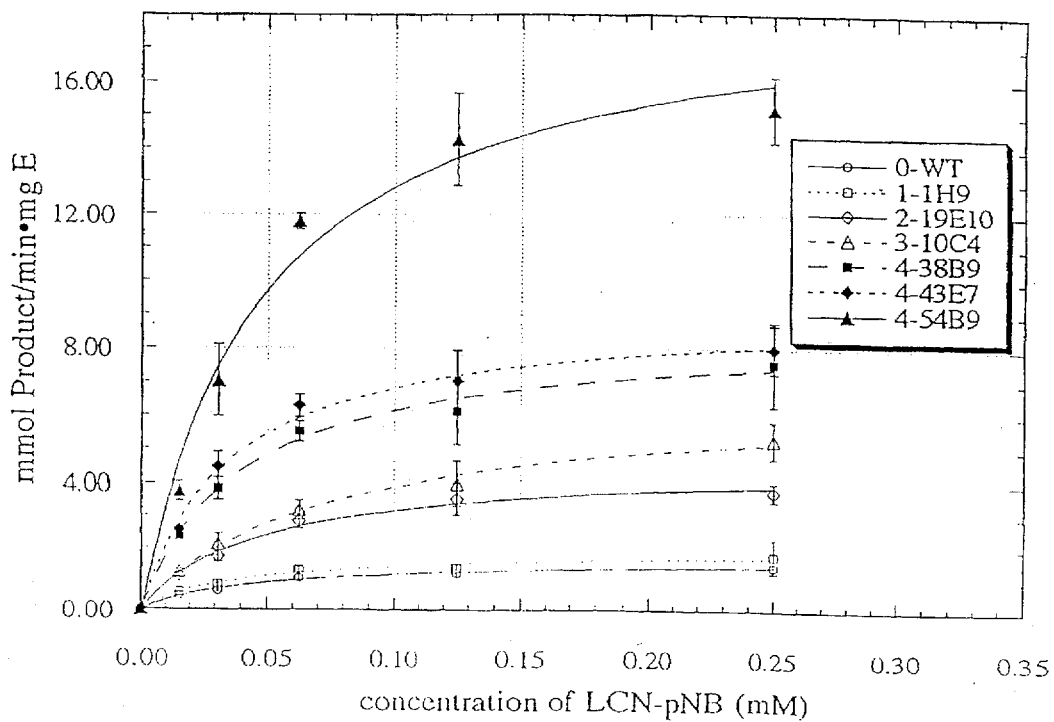
FIG. 10a is a plot of variant and wild type pNB esterase reaction kinetics on p-nitrobenzyl loracarbef nucleus (LCN-pNB) in 1% dimethylformamide (DMF). Enzymes were added to a 30° C. reaction solution consisting of 0.1M PIPES pH 7.0, 1% DMF, and varying concentrations of LCN-pNB.
Figure 10B:
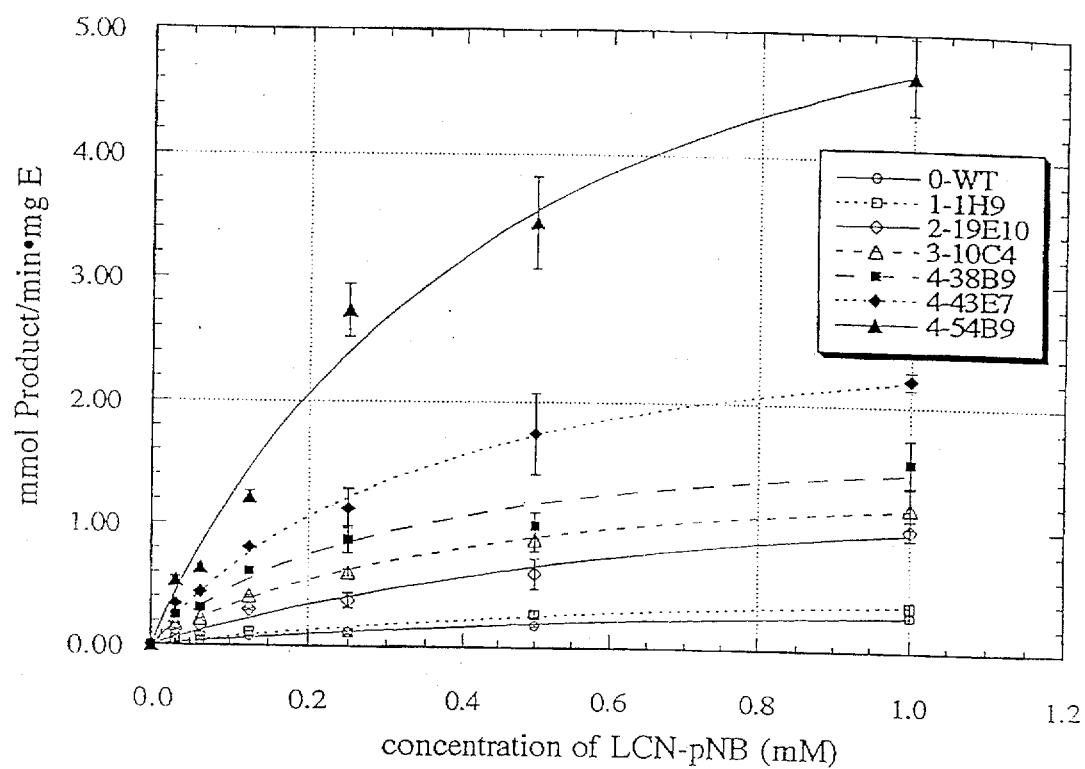
FIG. 10b is a plot of variant and wild type pNB esterase reaction kinetics on p-nitrobenzyl loracarbef nucleus (LCN-pNB) in 15% dimethylformamide (DMF). Enzyme were added to a 30° C. reaction solution consisting of 0.1M PIPES pH 7.0, 15% DMF, and varying concentrations of LCN-pNB.

FIGS. 10a and b show the kinetic data obtained on the target LCN-pNB substrate. All the same trends are observed on the LCN-pNB substrate that were seen on the screening substrate (i.e. the fourth generation variants are more active than the third generation variant, which is more active than the second generation variant, etc.), with only minor exceptions. The first exception is that 1-1H9 no longer lags wild type in specific activity on this substrate. The second is that many of the variants, and especially those in the fourth generation, exhibit slightly lower increases in activity over wild type. For example 4-54B9 is now approximately 14 times more active than wild type on LCN-pNB, versus 16 times wild type on LCN-pNP. Additionally, DMF has a bigger negative effect on the LCN-pNB hydrolysis reaction than it does the hydrolysis of LCN-pNP. On LCN-pNP, 15% DMF reduces the maximal activity by a factor of two in the two best variants in 1% DMF, while 15% DMF affects the LCN-pNB hydrolysis by reducing the maximal activity by a factor of three over the 1% DMF activity.

Figure 12:
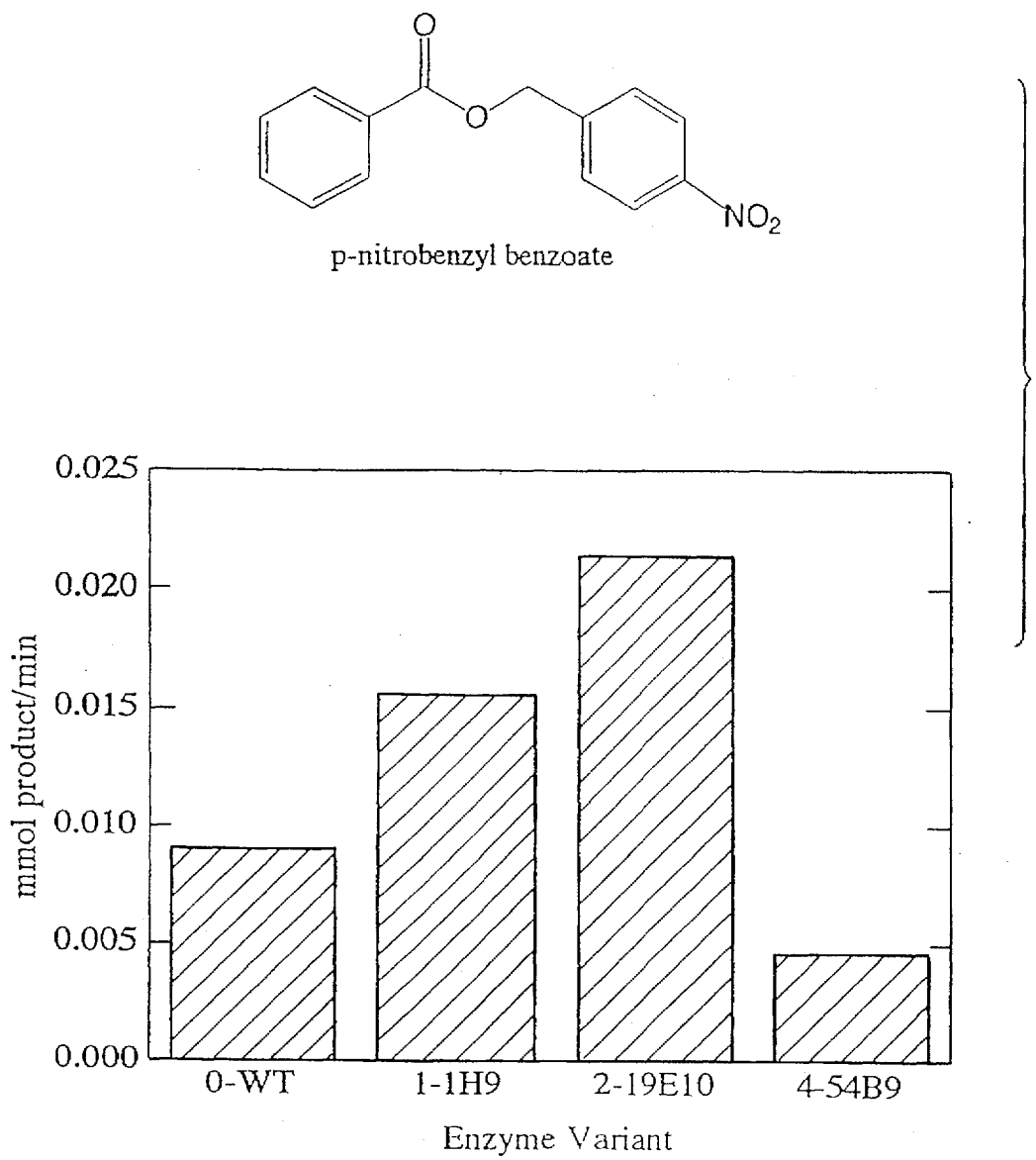
FIG. 12 shows graphic results of HPLC measurement of product of variant and wild type pNB esterase reaction on 1.0 mM p-nitrobenzyl benzoate in 20% dimethylformamide (DMF). The reaction was performed in 0.1M PIPES pH 7.0, 20% DMF and 1.0 mM substrate, 30° C.

The results shown in the FIGS. were used to calculate the $k_{cat}$, KM and $k_{cat}$/KM values reported in Table 3. In the case of the pNPA substrate, only $k_{cat}$/KM is reported because the solubility of the pNPA substrate did not permit the high substrate concentrations required to accurately determine the individual $k_{cat}$ and KM parameters. DMF dramatically increases $K_M$ while also decreasing $k_{cat}$. For the LCN substrates, the mutations accumulated during directed evolution mitigate the increased $K_M$. The effects on $k_{cat}$, however, are more prominent: $k_{cat}$ increases more than 9-fold from wild type to 4-54B9 in 15% DMF, while $K_M$ decreases by less than a factor of two on LCN-pNB. This result reflects the relatively high substrate concentration used during screening (0.8 mM). At substrate concentrations on the order of $K_M$, increased specific activity will result mainly from improvements in $k_{cat}$. These improvements are obviously the most useful for enzymes intended to be used for transformations in high substrate concentrations.

peak areas are shown for the different substrate/enzyme combinations in FIGS. 11 and 12. L-glutamine pNB is soluble in aqueous buffer. Its enzyme-catalyzed deprotection in the absence of DMF is shown in FIG. 11a. All the pNB esterases tested catalyze this reaction, with wild type being the most active. The activity of the enzyme variant decreases from generation to generation. The results are altered significantly, however, when 20% DMF is added (FIG. 11b). Under these conditions, 2-19E10 pNB esterase demonstrates the mosst activity toward removing the pNB-protecting group from L-glutamine p-nitrobenzyl ester. The first generation variant 1-1H9 outperforms wild type by 20%, and the second generation variant 2-19E10 outperforms the wild type enzyme by 60%. The fourth generation variant 4-54B9 apparently introduces a substitution which disrupts the earlier generations' enhancements of activity: this enzyme has lost the ability to catalyze this reaction better than wild type.

Figure 9B:
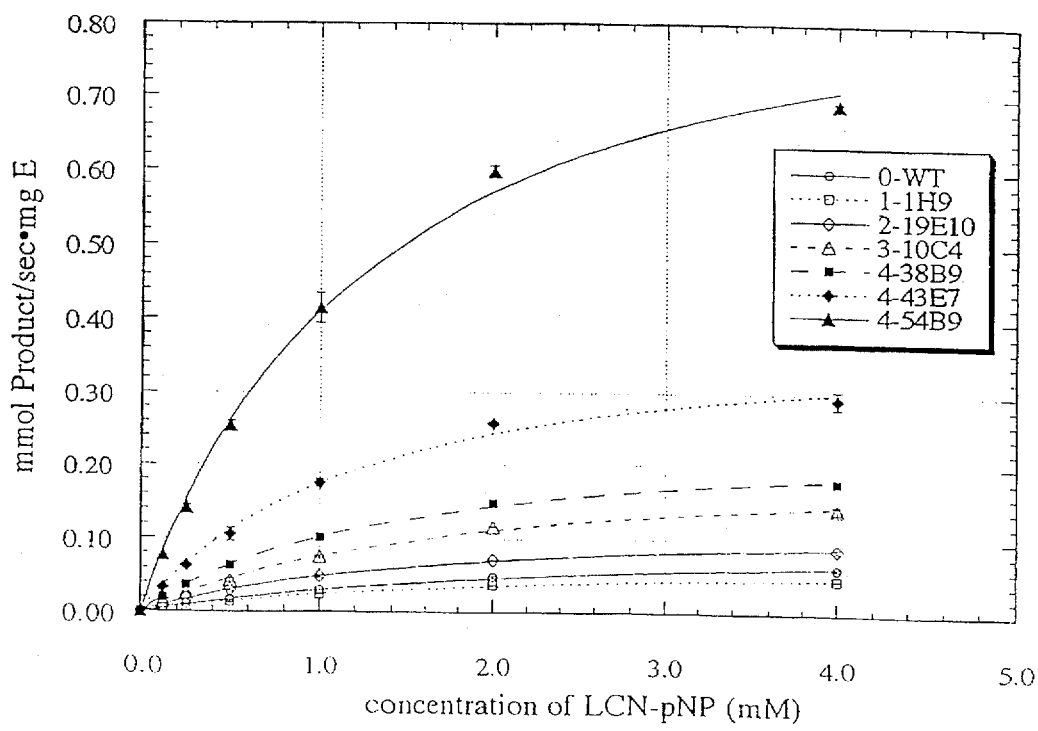
FIG. 9b is a plot of variant and wild type pNB esterase reaction kinetics on p-nitrophenyl loracarbef nucleus (LCN-pNP) in 15% dimethylformamide (DMF). Enzymes were added to a 30° C. reaction solution consisting of 0.1M PIPES pH 7.0, 15% DMF, and varying concentrations of LCN-pNP.
Figure 9C:
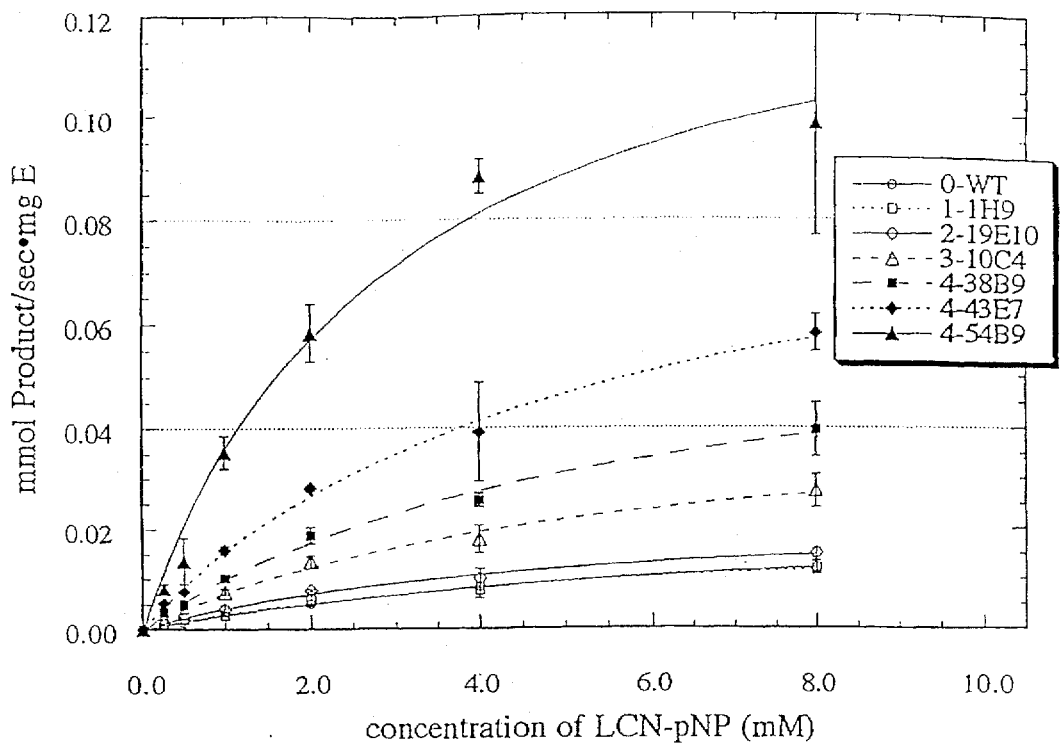
FIG. 9c is a plot of variant and wild type pNB esterase reaction kinetics on p-nitrophenyl loracarbef nucleus (LCN-pNP) in 30% dimethylformamide (DMF). Enzymes were added to a 30° C. reaction solution consisting of 0.1M PIPES pH 7.0, 30% DMF, and varying concentrations of LCN-pNP.

The hydrolysis of p-nitrobenzyl benzoate, reported in FIG. 12, shows the same trends demonstrated in FIG. 9b, although more dramatically. Because p-nitrobenzyl benzoate is not soluble in aqueous buffer, the assays on this

TABLE 3

| | p-nitrophenyl acetate | | |
|---|---|---|---|
| Variants | 0% DMF kcat/Km | 15% DMF kcat/Km | 30% DMF kcat/Km |
| 0-WT | 5.67 | 0.94 | 0.24 |
| 1-1H9 | 4.05 | 1.08 | 0.32 |
| 2-19E10 | 3.20 | 0.89 | 0.28 |
| 3-10C4 | 2.50 | 0.86 | 0.33 |
| 4-38B9 | 3.04 | 1.03 | 0.36 |
| 4-43E7 | 2.42 | 0.81 | 0.29 |
| 4-54B9 | 2.57 | 0.64 | 0.27 |

| | p-nitrophenyl loracarbef nucleus | | | | | | | | |
|---|---|---|---|---|---|---|---|---|---|
| | kcat | 0% DMF Km | kcat/Km | kcat | 15% DMF Km | kcat/Km | kcat | 30% DMF Km | kcat/Km |
| 0-WT | 0.14 | 0.07 | 2.11 | 0.10 | 2.36 | 0.04 | 0.024 | 7.55 | 0.003 |
| 1-1H9 | 0.08 | 0.03 | 2.47 | 0.07 | 1.84 | 0.04 | 0.021 | 6.05 | 0.003 |
| 2-19E10 | 0.25 | 0.09 | 2.68 | 0.12 | 1.50 | 0.08 | 0.023 | 4.67 | 0.005 |
| 3-10C4 | 0.35 | 0.11 | 3.15 | 0.21 | 1.77 | 0.12 | 0.044 | 5.18 | 0.009 |
| 4-38B9 | 0.39 | 0.06 | 6.18 | 0.25 | 1.41 | 0.17 | 0.067 | 5.68 | 0.012 |
| 4-43E7 | 0.67 | 0.08 | 8.51 | 0.40 | 1.27 | 0.31 | 0.094 | 5.09 | 0.018 |
| 4-54B9 | 1.44 | 0.12 | 12.09 | 0.93 | 1.27 | 0.73 | 0.141 | 2.92 | 0.048 |

| | p-nitrobenzyl loracarbef nucleus | | | | | |
|---|---|---|---|---|---|---|
| | kcat | 0% DMF Km | kcat/Km | kcat | 15% DMF Km | kcat/Km |
| 0-WT | 1.64 | 0.04 | 38.27 | 0.54 | 0.88 | 0.61 |
| 1-1H9 | 1.94 | 0.04 | 50.75 | 0.69 | 0.85 | 0.82 |
| 2-19E10 | 4.59 | 0.04 | 102.59 | 1.51 | 0.87 | 2.09 |
| 3-10C4 | 6.53 | 0.07 | 96.37 | 1.62 | 0.40 | 4.05 |
| 4-38B9 | 8.51 | 0.04 | 222.47 | 1.89 | 0.31 | 6.17 |
| 4-43E7 | 9.13 | 0.03 | 271.06 | 3.02 | 0.37 | 8.11 |
| 4-54B9 | 18.96 | 0.05 | 396.41 | 6.84 | 0.46 | 14.74 |

Performance of Evolved Enzymes on Other Substrates

To determine the extent to which the newly-evolved enzymes exhibited increased general p-nitrobenzyl esterase activity, four purified pNB esterases (0-WT, 1-1H9, 2-19E10, and 4-54B9) were assayed on L-glutamine p-nitrobenzyl ester and p-nitrobenzyl benzoate by HPLC, as described in Materials and Methods. The resulting product substrate were performed only in 20% DMF. In this environment, 1-1H9 is 60% better than wild type, and 2-19E10 is 2.5 times better than wild type. 4-54B9 again has lost the ability to outperform previous generation variants, including the wild type pNB esterase.

pH Studies

The pH optimum for activity of wild-type pNB esterase is 8.3 (6), while the screening for evolved pNB esterases was carried out at pH 7.0. To determine to what extent the pH-activity profiles of the pNB esterase were altered, or may have drifted, as a result of directed evolution at pH 7.0, the enzymes' abilities to hydrolyze the LCN-pNP screening substrate was measured as a function of pH. The activities generation, those being the A to G substitutions at position 1075 in two variants from generation 2, and the A to G substitution at position 181 in two variants of generation 4.

TABLE 4

Figure 13:
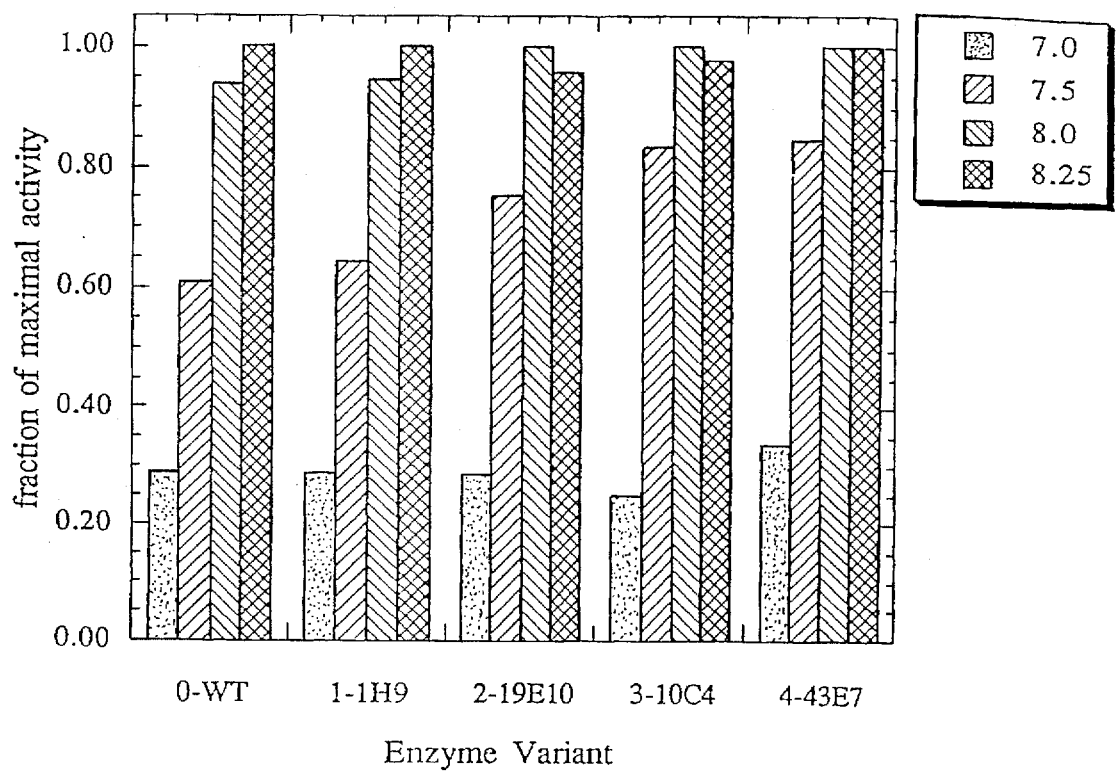
FIG. 13 shows the pH-activity profiles from pH 7.0 to 8.25 for a variant from each generation. The activity values for each variant are normalized to its maximal value. The enzyme samples were added to a 30° C. reaction solution consisting of 1% dimethylformamide (DMF), 0.5 mM p-nitrophenyl loracarbef nucleus, and 0.1M PIPES pH 7.0 to 8.25.

| DNA Pos. -12 | Gen 1 1H9 | Generation 2 | | | Gen 3 | Generation 4 | | | | | | Gen 5 |
|---|---|---|---|---|---|---|---|---|---|---|---|---|
| | | 13F3 | 19E10 A→T | 23E1 | 10C4 A→T | 38B9 A→T | 43E7 A→T | 53D5 A→T | 54B9 A→T | 73B4 A→T | 1A12 A→T |
| 87 | C→T | C→T | C→T | C→T | C→T | C→T | C→T | C→T | C→T | C→T | C→T |
| 102 | | | | | | | | | T?C | | |
| 181 | | | | | | A→G | | | | A→G | A→G |
| 255 | | | | | | | | | T→C | | |
| 283 | | | | | | | A→G | | | | |
| 290 | | A→G | | | | | | | | | |
| 291 | | | | | T→C | | | | | | |
| 333 | | | T→A | | T→A | T→A | T→A | T→A | T→A | T→A | T→A |
| 399 | | | | T→C | | | | | | | |
| 433 | | | | | T→A | T→A | T→A | T→A | T→A | T→A | T→A |
| 720 | | | | | | | | T→C | | | |
| 803 | | | | | | | | | A→G | | |
| 814 | | | | T→C | | | | | | | |
| 968 | A→G | A→G | A→G | A→G | A→G | A→G | A→G | A→G | A→G | A→G | A→G |
| 1003 | | | | | | T→G | | | | | |
| 1004 | | | | | | | | | T→C | | T→C |
| 1031 | | | | C→T | | | C→T | | | | |
| 1075 | | A→G | A→G | | A→G | A→G | A→G | A→G | A→G | A→G | A→G |
| 1112 | A→T | A→T | A→T | A→T | A→T | A→T | A→T | A→T | A→T | A→T | A→T |
| 1122 | | A→G | | | | | | | | | |
| 1239 | | | A→G | | A→G | A→G | A→G | A→G | A→G | A→G | A→G |
| 1302 | | A→G | | | | | | | | | |
| 1485 | A→G | A→G | A→G | A→G | A→G | A→G | A→G | A→G | A→G | A→G | A→G |
| 1568 | | | | | | | | | | T→A | |
| 1618 | | | | T→C | | | | | | | |
| 1658 | A→G | A→G | A→G | A→G | A→G | A→G | A→G | A→G | A→G | A→G | A→G |
| 1678 | T→C | T→C | T→C | T→C | T→C | T→C | T→C | T→C | T→C | T→C | T→C |
| 1745 | | | C→T | | C→T | C→T | C→T | C→T | C→T | C→T | C→T | normalized to the maximum activity for enzyme variants from each of the four generations are shown in FIG. 13. While the pH optima of the enzyme variants have not changed significantly, the pH-activity profiles of those from later generations have broadened slightly. In other words, reaction rates at lower pH values increase slightly more during directed evolution than does the maximum rate ~pH 8.25, which probably once again reflects the choice of pH 7.0 for screening.

Sequence Analysis

FIG. 3 presents the aligned DNA sequences of all the variants sequenced during this study. The variants are listed in order by generation, and the sequences start with DNA base one (A of the first codon ATG). The DNA bases conserved between all members of this pNB esterase family are boxed. Where a mutation has occurred, the column of DNA bases is not boxed, and a dash is indicated in the consensus sequence at the bottom of each set of rows.

Table 4 summarizes the positions of the DNA base changes in the enzyme variants with respect to the wild type pNB esterase gene sequence for all the variants sequenced during this study. Bold type indicates the substitutions not present in the previous generation parent enzyme. Horizontal lines indicate the beginning and end of the open reading frame, which starts at base position 1 and ends at position 1470. All together the sequences contain 31 substitutions, of which 29 are unambiguously unique. The two substitutions which may not be unique are those where identical substitutions were found in two different variants of the same FIG. 4 presents the amino acid sequence alignment of the pNB esterase family as translated from the DNA sequence alignment in FIG. 3. As before, the variants are listed in order by generation. The sequences start with amino acid one, and the DNA bases conserved between all members of this pNB esterase family are boxed. Where a mutation has occurred, the column of amino acid residues is not boxed, and a dash is indicated in the consensus sequence at the bottom of each set of rows.

Figure 2:
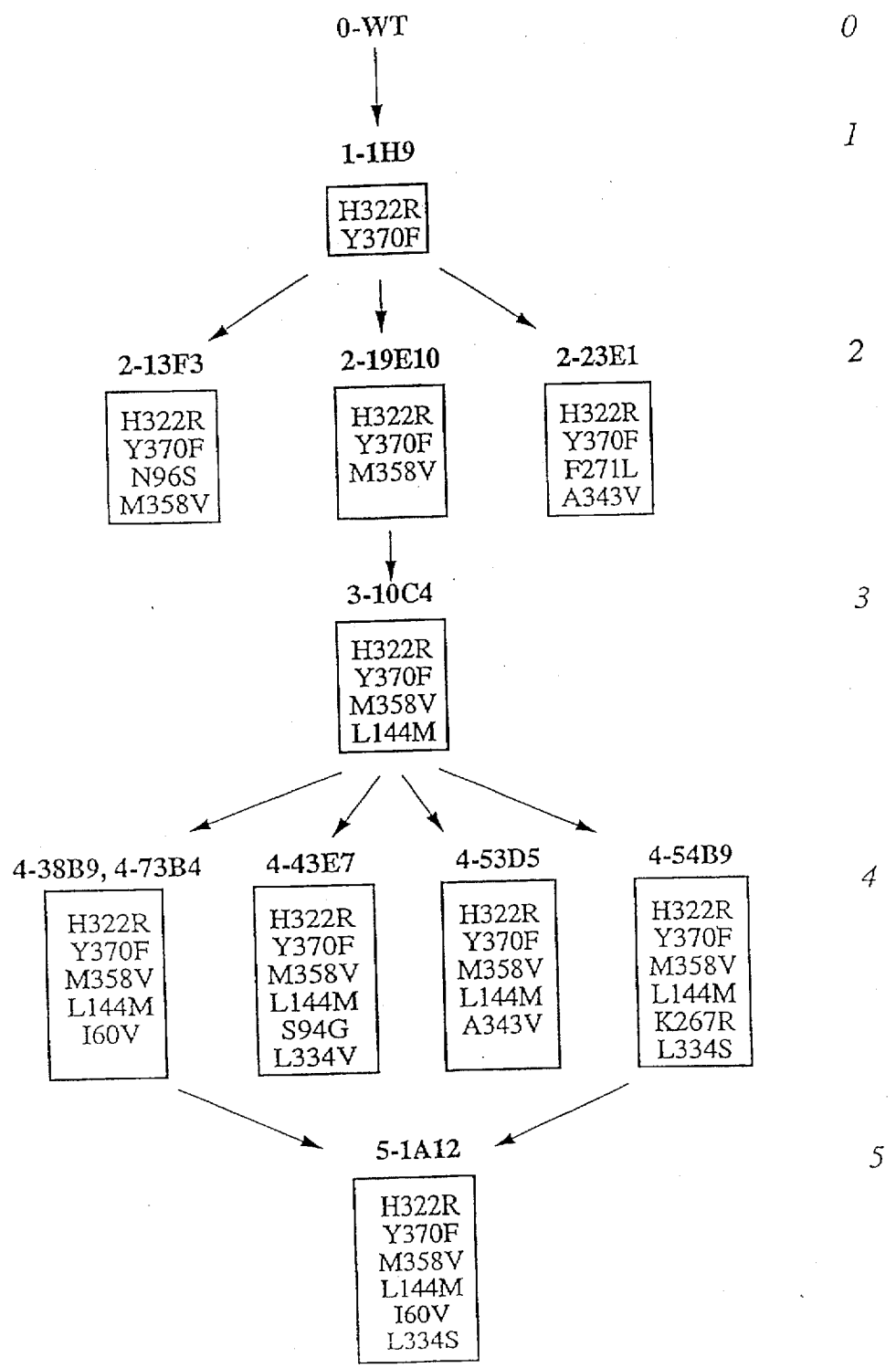
FIG. 2 is a diagram showing the amino acid substitution progression in para-nitrobenzyl esterase variants. The esterase variants are labeled in bold-type and boxed beneath each label are the amino acid substitutions present in each variant. The amino acid substitutions were determined by translation of DNA sequencing results.
Figure 4A:
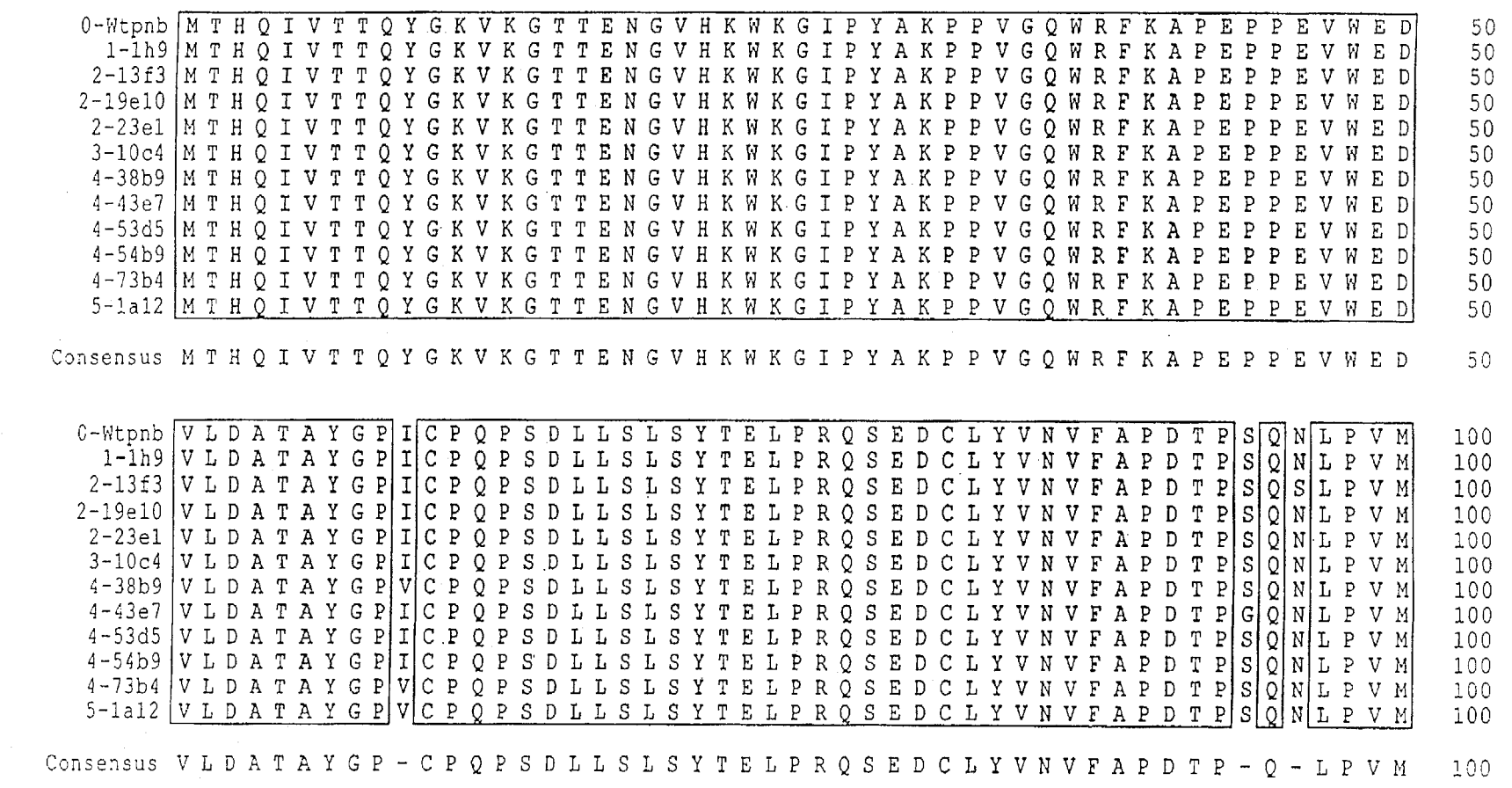
Figure 4B:
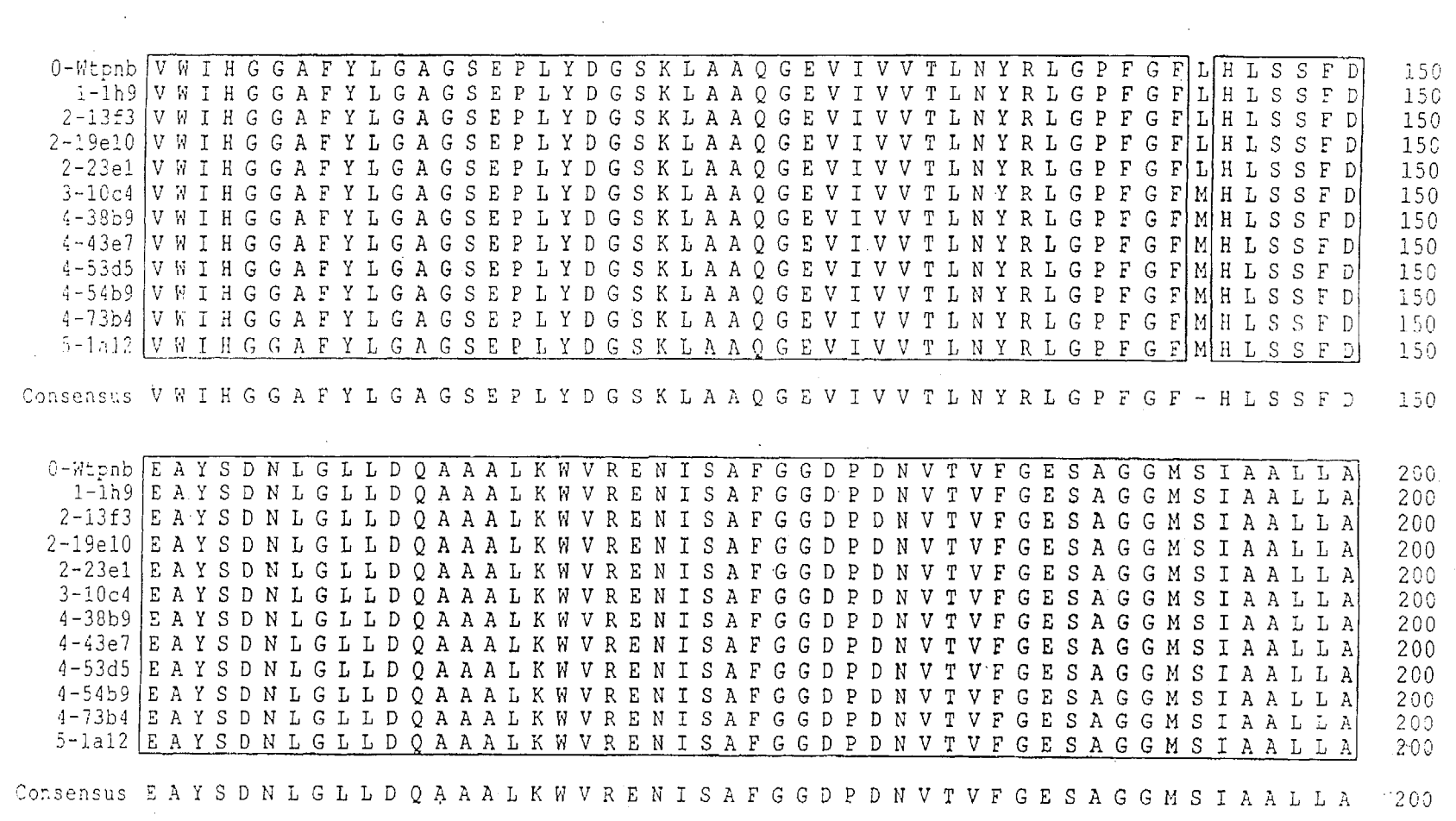
Figure 4D:
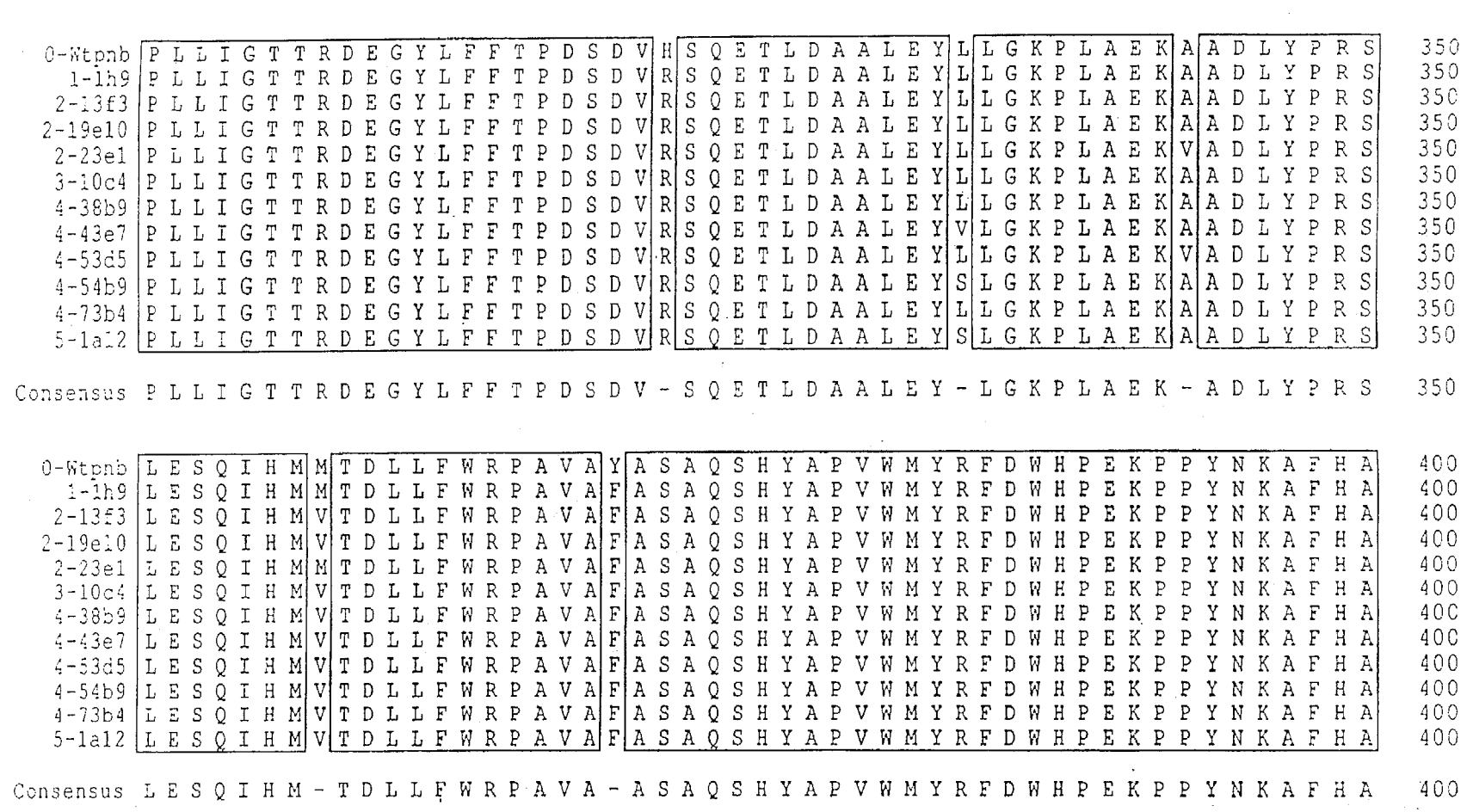
Figure 4E:
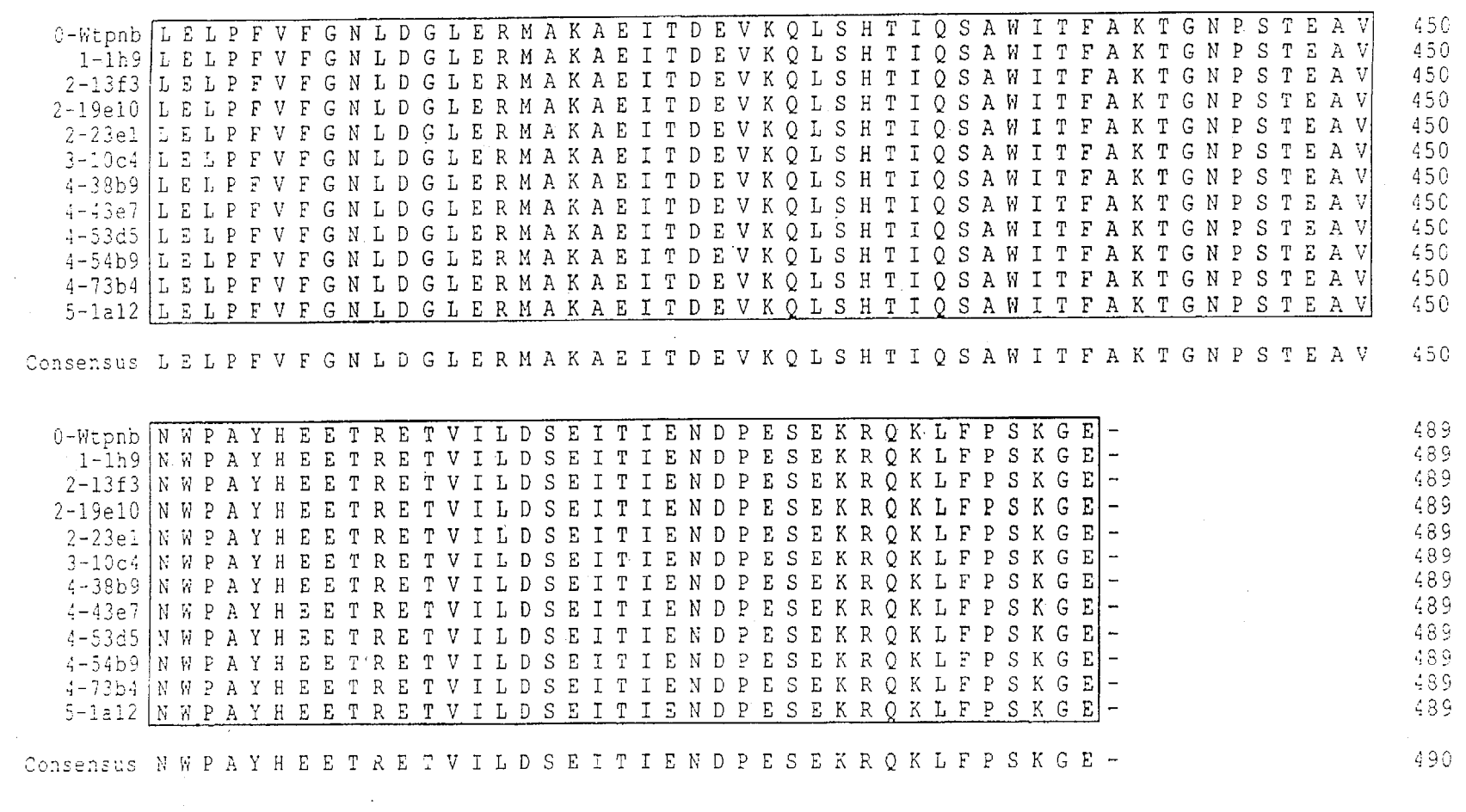

FIG. 2 is an "evolution tree" summarizing the amino acid substitutions and positions resulting from the amino acid sequence information in FIG. 4 and Table 4. All three clones sequenced from the second generation contain the substitutions observed in the 1-1H9 sequence, as well as a few new additional substitutions. This can be seen at the DNA level in Table 4 and at the protein level in FIG. 2. Two of the second generation clones contain the same DNA substitution, an A to G substitution at position 1075, which gives rise to the substitution of methionine at position 358 by valine. This residue is believed to be responsible for the increased specific activity of these two clones, as it is the only non-silent mutation in clone 2-19E10, whose catalytic activity is slightly better than 2-13F3. 2-19E10 was chosen to parent the third round of mutagenesis. One silent and one translated substitution are added to the evolutionary sequence in 3-10C4; a T to A substitution at position 433 gives rise to leucine 144 substituted by methionine. The next five sequences are progeny of 3-10C4 from the fourth generation. All have the eight DNA base substitutions of 3-10C4 in common as the cumulative result of the three previous rounds of evolution. 4-38B9 and 4-73B4 each contain only an identical open reading frame substitution, an A to G change at position 181, leading to isoleucine at position 60 changed to valine. As a result, these two variants are listed together in FIG. 2. 4-43E7 and 4-54B9 each contain two substitutions; one occurs within identical codons in the DNA sequence, giving rise to changes in leucine 334 to valine in 4-43E7 and serine in 4-54B9. 5-1A12 was created as a combination of 4-38B9 and 4-54B9 by cutting and religating these two genes near the 1000 DNA base position. S-1A12 is therefore expected to contain the isoleucine 60 to valine substitution from 4-38B9 and the leucine 334 to serine substitution from 4-54B9.

The location versus frequency of substitution was examined and the locations of substitutions resulting in amino acid changes appears distinctly non-random. Fully half of the translated substitutions DNA mutations lie within a 144 base pair stretch of DNA (less than 10% of the open reading frame). This is due to the fact that a non-random selection of enzymes were chosen for sequencing (only those exhibiting improved activity). This region of the amino acid sequence plays an important role in substrate recognition and enzyme activity.

Random Mutagenesis

The frequency of substitutions as a function of position within the gene sequence was determined. It was found that the locations of DNA substitutions in the sequenced genes are well distributed throughout the target sequence. Thus the error-prone PCR technique generates variations at random locations. The types of substitutions generated, however, are not random. Of the 29 unique substitutions, 25 were substitutions changing an A or T, 4 were substitutions of C, and none were substitutions of G. These bases were changed almost half of the time to G, with A to G changes making up the majority (9/10) of these substitutions. This non-randomness is also shown in the number of transition (purine to purine changes—A to G or C to T) to transversion (purine to pyrimidine changes—A to T/G or C to A/G or T to A/G) substitutions, where the transitions outnumber the transversions 24 to 5.

The conditions used in these examples (differing from normal PCR conditions by increases in all four dNTP concentrations) give a reported error-rate of between 1.5 and 4 base substitutions per 1000 bases. Under these conditions, the substitutions should be predominantly transitions (e.g. A to G), no transversions (e.g. A to T), and a small fraction of insertion or deletions. The sequence data presented here demonstrate a significant bias towards A to G substitutions, especially in the first two generations. We found that the substitution frequency was at the higher limit of the expected range, with the 1-1H9 variant demonstrating a substitution rate of 3.5 substitutions per 1000 bases, and highly populated with A to G changes. The third and fourth PCR reactions yielded lower mutation frequencies, with only 1 to 2.5 substitutions per 1000 bases. Transition substitutions still outnumbered transversion substitutions by 3 to 1. In no case was a G mutated.

Substitution bias in the resulting protein sequences also arises from the fact that the DNA sequence is translated to the amino acid sequence through the triplet coding ribosomes. Twenty amino acids are encoded by sixty-one triplet DNA codons, the distribution of these codons is far from even. For example, tryptophan is coded for by only one of the 64 triplet codons (TGG), while Leu is encoded by six. Single base changes within a codon are the only type of base changes we can expect to see, as the probability of making two random substitutions within one codon is small. On average, only five to six new amino acids are available to replace each amino acid in the original sequence by single base substitution. Thus, the translation process introduces non-randomness in the amino acid sequence. This is useful for directed evolution in accordance with the present invention, when one does not want to radically alter an enzyme that has some catalytic activity, but rather wants to incorporate small changes which enhance the enzyme's ability to perform. This bias towards conservative amino acid substitutions is demonstrated in the examples with most changes being conservative ones, such as tyrosine 370 to phenylalanine in 1-1H9, phenylalanine 271 to leucine in 2-23E1, and isoleucine 60 to valine in 4-38B9.

MATERIALS AND METHODS

DNA

The plasmid pNB106R was provided by Eli Lilly & Co (Indianapolis, Ind.). This plasmid contains the pNB esterase gene under the control of an altered 1 promoter, pL106 (U.S. patent application Ser. No. 07/739,280) (4). The plasmid also contains a temperature sensitive 1 CI repressor which inactivates the pL106 promoter below 35° C. Further, the plasmid contains an *E. coli* origin of replication, a plasmid copy control gene, and a tetracycline resistance gene.

Computer Work

Homology searches and sequence alignments were performed at the California Institute of Technology's Sequence Analysis Facility using the GCG Sequence Analysis Software Package version 8.0 from the Genetics Computer Group (University Research Park, Madison, Wis.). BLAST searches of the Brookhaven Protein Data Bank (PDB), the SWISS-PROT database, the Protein Information Resource database, and the translated GenBank database were performed at the National Center for Biotechnology Information using a BLAST network service (29). PHYLIP was used at the same facility to construct evolutionary trees (30).

Restriction of DNA

Plasmid and fragment DNA when required were cut with Bam HI and Xba I (Boerhinger Mannheim, Germany) in restriction buffer B at 37° C. for one hour. The resulting linear DNA was then run on a 1% agarose gel and separated into bands according to size. The appropriately sized band was excised from the gel and extracted using either the GeneClean (Bio101, Vista, Calif.) or Qiagen (Chatsworth, Calif.) method. In both cases purified DNA was eluted in Tris-EDTA buffer.

Random Mutagenesis

The pNB esterase gene (1470 base pairs (bp)) in pNB106R is flanked by an Xba I restriction site 51 bp before the start of the ORF and by a Bam HI site 313 bp downstream from the stop codon (4). PCR primers (3'-GAGCACATCAGATCTATTAAC-5' and 3'-GGAGTGGCTCACAGTCGGT-GG-5') were synthesized to complement regions 25 bp upstream of the Xba I site and 143 bp downstream of the Bam HI site to allow andom mutagenesis over a 2000 bp region including the entire pNB esterase open reading frame. A solution containing 1 mM dNTPs, 16.6 mM $(NH_4)_2SO_4$, 67 mM Tris-HCl (pH 8.8), 6.1 mM $MgCl_2$, 6.7 mM EDTA (pH 8.0), and 10 mM b-mercaptoethanol, 6 mg of forward and reverse primers, 10 ng of plasmid pNB106R and 2.5 units of Taq DNA polymerase (Perkin Elmer-Cetus, Foster City, Calif.) in a total volume of 100 mL were covered with 2–3 drops of light mineral oil (Sigma, St. Louis, Mo.)). The sample was then placed in a well containing 2–3 drops of mineral oil of a Precision Scientific thermal cycler. The thermal cycler repeats the following steps: 1 minute at 94° C., 2 minutes at 42° C., and 1 minute at 72° C. for 25 cycles. These conditions should generate an error frequency of approximately one substitution per 1000 bases, or approximately 1.5 substitutions per gene copy (10). The fragment of DNA amplified by this technique was then subjected to a phenol/chloroform extraction and ethanol precipitation. The DNA was restricted and purified as described above.

Competent Cell Preparation

Competent TG1 cells were prepared according to the CaCl2 method (31). TG1 cells were grown overnight at 37° C. in a 3 mL culture of LB broth. The cells were diluted 1:200 in fresh LB and allowed to grow to an $OD_{600}$ of 0.35 to 0.40. They were placed on ice for 1 hour and spun at maximum speed in a 4° C. Beckman tabletop centrifuge. The cell pellet was resuspended in 0.5 volumes of 0.1M $CaCl_2$ and allowed to sit on ice for 30 minutes to 1 hour and recentrifuged as before. The cell pellets were resuspended in sterile 0.02 volumes of 0.1M $CaCl_2$, 10% v/v glycerol and frozen at −70° C. until use.

Ligation and Transformation

Ligation reactions were performed using T4 DNA ligase (Boehringer-Mannheim, Germany). Vector DNA (the entire pNB106R plasmid excluding the pNB esterase gene between Xba I and Bam HI), insert DNA (the pNB esterase gene between Xba I and Bam HI), 10X ligation buffer, water and enzyme were combined and incubated at 4° C. overnight (12–16 hours). The solution was incubated with previously prepared competent cells on ice for 1 hour. The cells were then heat shocked at 42° C. for 1 minute, supplied with an equal volume of LB media, and incubated at 30° C. for 45 minutes. This solution was then plated onto LB plates containing tetracycline to 20 mg/mL (LB Tet plates).

Screening

Transformants arising from ligations of pNBE vector and randomly mutagenized inserts were allowed to grow for 36 to 48 hours before shifting to 42° C. to induce expression of the pNB esterase gene. After an eight hour induction period, each colony was picked with a sterile toothpick and resuspended in a unique well of a 96 well plate containing 200 mL of 0.1M Tris-HCl, pH 7.0. The turbidity of each well was measured as the absorbance at 620 nm adjusted by a cell-free reference well by a 96 well plate reader. A 20 mL aliquot from each well was pipetted into a second 96 well plate, to which was added 200 mL of a substrate solution containing 0.8 mM para-nitrophenyl acetate (pNPA) and 0.4% (v/v) acetonitrile or para-nitrophenyl loracarbef nucleus (LCN-pNP), 0.1M Tris-HCl pH 7.0, and between 0 and 30% v/v dimethylformamide (EM Science Guaranteed Reagent grade). The resulting reaction was monitored using the 96 well plate reader at 405 nm. Reactions were typically monitored for 11 data points varying from 15 seconds between data points for 0% DMF measurements to 180 seconds between data points for 30% DMF. The slopes of the best-fit lines through the resulting 11 data points for each of the 96 wells were normalized by the corresponding absorbance at 620 nm measured previously. These normalized values were compared, and the wells exhibiting the highest activity to turbidity ratios were plated onto LB Tet plates. Two single colonies from these plates were restreaked on LB Tet plates to provide single colony isolates for further testing. Two single colonies from each of these second plates (four colonies total) were then arrayed onto LB Tet plates using sterile toothpicks. This collection of potential variants was then rescreened using the activity to turbidity ratio assay again. Of those that showed better activity to turbidity than wild type, the best three were chosen for larger scale culture and purification.

Crude screening was performed on the fourth generation variants using the LCN-pNB substrate using a similar whole cell assay. 0.10 ml samples of the resuspended colonies were removed from each well of the 96 well plate and added to a quartz cuvette containing a 1000 ml reaction solution consisting of 2.5% DMF, 0.1M Tris-HCl pH 7.0, and 0.25 mM LCN-pNB. The absorbance at 291 nm of each sample was measured for 2.5 min. using a UV spectrophotometer. Initial rates were measured for both the LCN-pNP substrate in the 96 well plate assay (above) and the LCN-pNB substrate in quartz cuvettes. Both sets of slopes generated from the initial rate data were normalized to the turbidity measurements at 620 nm.

Cell Culture

Single colonies were inoculated into 5 mL LB Tet culture tubes and allowed to grow overnight at 30° C. The contents of these tubes were then used to inoculate a one-liter culture of LB Tet and allowed to grow to maximum turbidity. These one-liter cultures were decanted into sterile centrifuge bottles and spun at 6000 rpms in a JA-10 rotor for 15 minutes in a Beckman centrifuge. The cell pellets were resuspended in LB Tet pre-warmed to 42° C. The flasks were placed in a 42° C. incubator and allowed to shake for 8 hours (4). The cells were harvested by similar centrifugation and resuspended in a centrifuge tube in 25 mL of Buffer A (Lysis Buffer), consisting of 10 mM potassium phosphate, 1 mM b-mercaptoethanol, and 0.5 mM EDTA, pH 7.0.

Cell Lysis

A French Press was used to lyse the harvested cells. The lysis was accomplished by placing the chilled sample into a steel housing, which was compressed to 20,000 atmospheres. A small needle valve was then opened and the cells were released to ambient conditions, causing the cells to rupture. This process was repeated three times to insure complete lysis. The steel housing was kept chilled prior to use at 4° C. and the samples were stored before and after on ice.

Purification

After lysis the cell debris was pelleted by centrifugation at 12,000 g in a JA-20 rotor for 15 minutes at 4° C. (6). The cell lysate supernatant was adjusted to pH 5.0 with HCl, and the newly formed precipitate was removed by centrifugation at 12,000 g in a Beckman JA-20 rotor for 30 minutes at 4° C. The supernatant volume was measured and ammonium sulfate was dissolved to 45% saturation at 0° C. For reference, the ammonium sulfate saturation amount used for calculations was 41.22 g/100 mL solution at 0° C. The solution was chilled to 0° C. on ice for 5 minutes and centrifuged in a JA-20 rotor at 12,000 g for 30 min. at 4° C. The supernatant was transferred to a new centrifuge tube, where ammonium sulfate was added to bring the final amount to 85% saturation at 0° C. Centrifugation was performed as before, and the supernatant discarded. The pellet was redissolved in Buffer B (10 mM Tris-HCl, 50 mM NaCl, 1 mM b-mercaptoethanol, and 0.5 mM EDTA, pH 8.5), placed in an Amicon® spin filtration unit (Centricon—10) and buffer exchanged three times with Buffer B to remove the ammonium sulfate. The resulting protein sample was applied to a DEAE-sepharose column (2.5 cm ID×10 cm high) pre-equilibrated in Buffer B. The column was rinsed with buffer B until the baseline was restored. The column was then rinsed with buffer C (10 mM Tris-HCl, 50 mM NaCl, pH 7.0) until the pH reached 7.0. An NaCl gradient from 50 to 500 mM in buffer C (300 mls total volume) was passed through the column and fractions collected. Those fractions containing activity were pooled and then applied to an immobilized metal affinity chromatography (IMAC) column (2.5 cm ID×10 cm high, Fast-flow Chelating Sepharose, Pharmacia, Sweden) prepared as per the manufacturer's instructions. The column was first pretreated by rinsing with three column volumes of (one column volume was approximately 50 ml) 0.5M NaCl, 50 mM EDTA pH 8.5 to remove all chelated metal ions, 2M NaCl to remove any ionically bound material, and 1M NaOH to remove any denatured protein. Copper as 100 mM copper sulfate in 100 mM sodium acetate pH 4.6 was reloaded onto the IMAC column, washed with 20 mM sodium phosphate, 0.5M NaCl, 50 mM imidazole pH 7.2 until pH 7.2, and finally equilibrated with five column volumes of 20 mM sodium phosphate, 0.5M NaCl, 1 mM imidazole for loading. The sample was applied to the column and the column washed with the 1 mM imidazole solution until baseline was restored. A linear gradient formed by 100 mls of 1 mM and 10 mM imidazole solutions (200 mls total volume) was applied, and fractions were collected. All tubes demonstrating higher than background activity were pooled, concentrated, and buffer exchanged into 0.1M Tris-HCl, pH 7.0 in the Amicon Centricon-10 units as before.

SDS-Page Gels

SDS-Page gels were used to determine purity of protein solutions. Separating gels were made of 10% acrylamide and allowed to gel under butanol. After gelling the butanol was removed and a 4% acrylamide stacking gel was poured on top of the separating gel. Up to 5 mL of concentrated protein samples were mixed with 20 mL loading buffer (10% glycerol, 1% SDS, etc.) and boiled for 4 minutes. The 25 mL samples were loaded onto the gel and run at 200 V for approximately 30 minutes, at which time the loading buffer dye reached the bottom of the gel. The gel was removed from the apparatus and stained using a Coomasie blue stain solution. After staining a minimum of 45 minutes, the Coomasie blue stain was poured off and destain was added. This was allowed to incubate until the solution approximated the color of the gel, at which time the destain was poured off and new destain was added. The gel was then dried and sealed in plastic for further handling.

Protein Concentration Assays

Protein samples were assayed using the Bio-Rad Protein Assay Reagent. The reagent was diluted 1:4 in water and filtered to remove any particulates. 20 mL of protein sample was combined with 980 mL of dilute reagent in a 2 mL spectrophotometer cuvette and allowed to incubate for 10–30 minutes. The samples' absorbance was then measured at 595 nm and compared to that of a sample of known enzyme concentration.

Kinetic Assays

Kinetic assays were performed on three substrates: pNPA, LCN-pNP, and p-nitrobenzyl loracarbef nucleus (LCN-pNB). For pNPA and LCN-pNP substrates, final concentrations varying from 0.0625 mM to 16 mM and 0, 15, and 30% DMF in 0.1M PIPES (Sigma), pH 7.0 were combined with equal volumes of enzyme samples. These samples were mixed simultaneously in a 96 well plate and monitored with the 96 well plate reader. The absorbance values were recorded, linearly regressed, and then used for calculating kinetic parameters. For the LCN-pNB substrate, final concentrations varying from 0.0156 mM to 8.0 mM and 0, 15 and 30% DMF in PIPES, pH 7.0 were combined with enzyme samples in a quartz cuvette and were measured in a spectrophotometer at 289 nm. All assays were measured in triplicate.

Additionally, assays on pNB containing substrates were performed by adding a reaction mix containing 1.0 mM substrate in 1 to 20% DMF and 0.1M phosphate buffer, pH 7.0 to a small volume of enzyme solution, incubating at room temperature for 20 to 60 minutes, and then stopping the reaction with an equal volume of acetonitrile. The samples were then injected into an HPLC containing a C18 chromatography column and reaction products were separated using a gradient between 95% 1 mM triethylamine pH 2.5/5% methanol and 100% methanol. The resulting peaks were monitored at 270 nm and recorded on an IBM PC data acquisition system. These peaks were then numerically integrated and used for comparison between enzyme samples.

The preceding examples demonstrate the usefulness of the present invention in preparing, isolating and identifying esterases which have improved stability and/or ester hydrolysis activity in organic media relative to the natural enzyme.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
  ( A ) ORGANISM:
  ( C ) INDIVIDUAL ISOLATE: 0- Wtpnb ( i x ) FEATURE:
  ( A ) NAME/KEY: CDS
  ( B ) LOCATION: complement (1..1470)

( x i ) SEQUENCE DESCRIPTION: SEQ ID NO:1:

| | | | | | | |
|---|---|---|---|---|---|---|
| ATGACTCATC | AAATAGTAAC | GACTCAATAC | GGCAAAGTAA | AAGGCACAAC | GGAAAACGGC | 60 |
| GTACATAAGT | GGAAAGGCAT | CCCCTATGCC | AAGCCGCCTG | TCGGACAATG | GCGTTTTAAA | 120 |
| GCACCTGAGC | CGCCTGAAGT | GTGGGAAGAT | GTCCTTGATG | CCACAGCGTA | CGGTCCTATT | 180 |
| TGCCCGCAGC | CGTCTGATTT | GCTCTCACTG | TCGTATACAG | AGCTGCCCCG | CCAGTCCGAG | 240 |
| GATTGCTTGT | ATGTCAATGT | ATTTGCGCCT | GACACTCCAA | GTCAAAATCT | TCCTGTCATG | 300 |
| GTGTGGATTC | ACGGAGGCGC | TTTTTATCTT | GGAGCGGGCA | GTGAGCCATT | GTATGACGGA | 360 |
| TCAAAACTTG | CGGCACAGGG | AGAAGTCATT | GTCGTTACAT | TGAACTATCG | GCTGGGGCCG | 420 |
| TTTGGCTTTT | TGCACTTGTC | TTCGTTTGAT | GAGGCGTATT | CCGATAACCT | TGGGCTTTTA | 480 |
| GACCAAGCCG | CCGCGCTGAA | ATGGGTGCGG | GAGAATATCT | CAGCGTTTGG | CGGTGATCCC | 540 |
| GATAACGTAA | CAGTATTTGG | AGAATCCGCC | GGCGGCATGA | GCATTGCCGC | GCTGCTCGCT | 600 |
| ATGCCTGCGG | CAAAAGGCCT | GTTCCAGAAA | GCGATCATGG | AAAGCGGCGC | TTCCCGAACA | 660 |
| ATGACAAAAG | AACAAGCGGC | AAGCACTGCG | GCTGCCTTTT | TACAGGTCCT | TGGGATTAAT | 720 |
| GAGAGCCAGC | TGGACAGATT | GCATACTGTA | GCAGCGGAAG | ATTTGCTTAA | AGCGGCCGAT | 780 |
| CAGCTTCGGA | TTGCAGAAAA | AGAAAATATC | TTTCAGCTGT | TCTTCCAGCC | CGCCCTTGAT | 840 |
| CCGAAAACGC | TGCCTGAAGA | ACCAGAAAAA | TCGATCGCAG | AAGGGGCTGC | TTCCGGCATT | 900 |
| CCGCTATTGA | TTGGAACAAC | CCGTGATGAA | GGATATTTAT | TTTTCACCCC | GGATTCAGAC | 960 |
| GTTCATTCTC | AGGAAACGCT | TGATGCAGCA | CTCGAGTATT | TACTAGGGAA | GCCGCTGGCA | 1020 |
| GAGAAAGCTG | CCGATTTGTA | TCCGCGTTCT | CTGGAAAGCC | AAATTCATAT | GATGACTGAT | 1080 |
| TTATTATTTT | GGCGCCCTGC | CGTCGCCTAT | GCATCCGCAC | AGTCTCATTA | CGCCCCTGTC | 1140 |
| TGGATGTACC | GGTTCGATTG | GCACCCGGAG | AAGCCGCCGT | ACAATAAAGC | GTTTCACGCA | 1200 |
| TTAGAGCTTC | CTTTTGTCTT | TGGAAATCTG | GACGGATTGG | AACGAATGGC | AAAAGCGGAG | 1260 |
| ATTACGGATG | AGGTGAAACA | GCTTTCTCAC | ACGATACAAT | CCGCGTGGAT | CACGTTCGCT | 1320 |
| AAAACAGGAA | ACCCAAGCAC | CGAAGCTGTG | AATTGGCCGG | CGTATCATGA | AGAAACGAGA | 1380 |
| GAGACGGTGA | TTTTAGACTC | AGAGATTACG | ATCGAAAACG | ATCCCGAATC | TGAAAAAAGG | 1440 |
| CAGAAGCTAT | TCCCTTCAAA | AGGAGAATAA | | | | 1470 |

( 2 ) INFORMATION FOR SEQ ID NO:2:

( i ) SEQUENCE CHARACTERISTICS:
    ( A ) LENGTH: 489 amino acids
    ( B ) TYPE: amino acid
    ( D ) TOPOLOGY: linear ( i i ) MOLECULE TYPE: enzyme ( x i ) SEQUENCE DESCRIPTION: SEQ ID NO:2:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
            20                  25                  30
```

```
Pro Val Gly Gln Trp Arg Phe Lys Ala Pro Glu Pro Pro Glu Val Trp
         35                  40                  45
Glu Asp Val Leu Asp Ala Thr Ala Tyr Gly Pro Ile Cys Pro Gln Pro
         50                  55                  60
Ser Asp Leu Leu Ser Leu Ser Tyr Thr Glu Leu Pro Arg Gln Ser Glu
65                   70                  75                   80
Asp Cys Leu Tyr Val Asn Val Phe Ala Pro Asp Thr Pro Ser Gln Asn
                 85                  90                  95
Leu Pro Val Met Val Trp Ile His Gly Gly Ala Phe Tyr Leu Gly Ala
                100                 105                 110
Gly Ser Glu Pro Leu Tyr Asp Gly Ser Lys Leu Ala Ala Gln Gly Glu
        115                 120                 125
Val Ile Val Val Thr Leu Asn Tyr Arg Leu Gly Pro Phe Gly Phe Leu
    130                 135                 140
His Leu Ser Ser Phe Asp Glu Ala Tyr Ser Asp Asn Leu Gly Leu Leu
145                 150                 155                 160
Asp Gln Ala Ala Ala Leu Lys Trp Val Arg Glu Asn Ile Ser Ala Phe
                165                 170                 175
Gly Gly Asp Pro Asp Asn Val Thr Val Phe Gly Glu Ser Ala Gly Gly
            180                 185                 190
Met Ser Ile Ala Ala Leu Leu Ala Met Pro Ala Ala Lys Gly Leu Phe
            195                 200                 205
Gln Lys Ala Ile Met Glu Ser Gly Ala Ser Arg Thr Met Thr Lys Glu
    210                 215                 220
Gln Ala Ala Ser Thr Ala Ala Ala Phe Leu Gln Val Leu Gly Ile Asn
225                 230                 235                 240
Glu Ser Gln Leu Asp Arg Leu His Thr Val Ala Ala Glu Asp Leu Leu
                245                 250                 255
Lys Ala Ala Asp Gln Leu Arg Ile Ala Glu Lys Glu Asn Ile Phe Gln
            260                 265                 270
Leu Phe Phe Gln Pro Ala Leu Asp Pro Lys Thr Leu Pro Glu Glu Pro
        275                 280                 285
Glu Lys Ser Ile Ala Glu Gly Ala Ala Ser Gly Ile Pro Leu Leu Ile
    290                 295                 300
Gly Thr Thr Arg Asp Glu Gly Tyr Leu Phe Phe Thr Pro Asp Ser Asp
305                 310                 315                 320
Val His Ser Gln Glu Thr Leu Asp Ala Ala Leu Glu Tyr Leu Leu Gly
                325                 330                 335
Lys Pro Leu Ala Glu Lys Ala Ala Asp Leu Tyr Pro Arg Ser Leu Glu
            340                 345                 350
Ser Gln Ile His Met Met Thr Asp Leu Leu Phe Trp Arg Pro Ala Val
        355                 360                 365
Ala Tyr Ala Ser Ala Gln Ser His Tyr Ala Pro Val Trp Met Tyr Arg
    370                 375                 380
Phe Asp Trp His Pro Glu Lys Pro Pro Tyr Asn Lys Ala Phe His Ala
385                 390                 395                 400
Leu Glu Leu Pro Phe Val Phe Gly Asn Leu Asp Gly Leu Glu Arg Met
                405                 410                 415
Ala Lys Ala Glu Ile Thr Asp Glu Val Lys Gln Leu Ser His Thr Ile
            420                 425                 430
Gln Ser Ala Trp Ile Thr Phe Ala Lys Thr Gly Asn Pro Ser Thr Glu
        435                 440                 445
Ala Val Asn Trp Pro Ala Tyr His Glu Glu Thr Arg Glu Thr Val Ile
```

| | 450 | | | | 455 | | | | 460 | | | | |
|---|---|---|---|---|---|---|---|---|---|---|---|---|---|
Leu Asp Ser Glu Ile Thr Ile Glu Asn Asp Pro Glu Ser Glu Lys Arg
465 470 475 480
Gln Lys Leu Phe Pro Ser Lys Gly Glu
485

( 2 ) INFORMATION FOR SEQ ID NO:3:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE: 1-1h9

( i x ) FEATURE:
        ( A ) NAME/KEY: CDS
        ( B ) LOCATION: complement (1..1470)

( x i ) SEQUENCE DESCRIPTION: SEQ ID NO:3:

```
ATGACTCATC AAATAGTAAC GACTCAATAC GGCAAAGTAA AAGGCACAAC GGAAAACGGC        60
GTACATAAGT GGAAAGGCAT CCCTTATGCC AAGCCGCCTG TCGGACAATG GCGTTTTAAA       120
GCACCTGAGC CGCCTGAAGT GTGGGAAGAT GTCCTTGATG CCACAGCGTA CGGTCCTATT       180
TGCCCGCAGC CGTCTGATTT GCTCTCACTG TCGTATACAG AGCTGCCCCG CCAGTCCGAG       240
GATTGCTTGT ATGTCAATGT ATTTGCGCCT GACACTCCAA GTCAAAATCT TCCTGTCATG       300
GTGTGGATTC ACGGAGGCGC TTTTTATCTT GGAGCGGGCA GTGAGCCATT GTATGACGGA       360
TCAAAACTTG CGGCACAGGG AGAAGTCATT GTCGTTACAT GAACTATCG GCTGGGGCCG        420
TTTGGCTTTT TGCACTTGTC TTCGTTTGAT GAGGCGTATT CCGATAACCT GGGCTTTTA        480
GACCAAGCCG CCGCGCTGAA ATGGGTGCGG GAGAATATCT CAGCGTTTGG CGGTGATCCC       540
GATAACGTAA CAGTATTTGG AGAATCCGCC GGCGGCATGA GCATTGCCGC GCTGCTCGCT       600
ATGCCTGCGG CAAAAGGCCT GTTCCAGAAA GCGATCATGG AAAGCGGCGC TTCCCGAACA       660
ATGACAAAAG AACAAGCGGC AAGCACTGCG GCTGCCTTTT TACAGGTCCT TGGGATTAAT       720
GAGAGCCAGC TGGACAGATT GCATACTGTA GCAGCGGAAG ATTTGCTTAA AGCGGCCGAT       780
CAGCTTCGGA TTGCAGAAAA AGAAAATATC TTTCAGCTGT CTTCCAGCC CGCCCTTGAT        840
CCGAAAACGC TGCCTGAAGA ACCAGAAAAA TCGATCGCAG AAGGGGCTGC TTCCGGCATT       900
CCGCTATTGA TTGGAACAAC CCGTGATGAA GGATATTTAT TTTCACCCC GGATTCAGAC        960
GTTCGTTCTC AGGAAACGCT TGATGCAGCA CTCGAGTATT TACTAGGGAA GCCGCTGGCA      1020
GAGAAAGCTG CCGATTTGTA TCCGCGTTCT CTGGAAAGCC AAATTCATAT GATGACTGAT      1080
TTATTATTTT GGCGCCCTGC CGTCGCCTTT GCATCCGCAC AGTCTCATTA CGCCCCTGTC      1140
TGGATGTACC GGTTCGATTG GCACCCGGAG AAGCCGCCGT ACAATAAAGC GTTTCACGCA      1200
TTAGAGCTTC CTTTTGTCTT TGGAAATCTG GACGGATTGG AACGAATGGC AAAAGCGGAG      1260
ATTACGGATG AGGTGAAACA GCTTTCTCAC ACGATACAAT CCGCGTGGAT CACGTTCGCT      1320
AAAACAGGAA ACCCAAGCAC CGAAGCTGTG AATTGGCCGG CGTATCATGA AGAAACGAGA      1380
GAGACGGTGA TTTTAGACTC AGAGATTACG ATCGAAAACG ATCCCGAATC TGAAAAAAGG      1440
```

CAGAAGCTAT TCCCTTCAAA AGGAGAATAA       1470

( 2 ) INFORMATION FOR SEQ ID NO:4:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: enzyme ( x i ) SEQUENCE DESCRIPTION: SEQ ID NO:4:

```
Met Thr His Gln Ile Val Thr Thr Gln Tyr Gly Lys Val Lys Gly Thr
 1           5                  10                  15

Thr Glu Asn Gly Val His Leu Trp Lys Gly Ile Pro Tyr Ala Lys Pro
            20                  25                  30

Pro Val Gly Gln Trp Arg Phe Lys Ala Pro Glu Pro Pro Glu Val Trp
            35                  40                  45

Glu Asp Val Leu Asp Ala Thr Ala Tyr Gly Pro Ile Cys Pro Gln Pro
        50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Leu Leu Gly
                325                 330                 335

Lys Pro Leu Ala Glu Lys Ala Ala Asp Leu Tyr Pro Arg Ser Leu Glu
            340                 345                 350
```

| Ser | Gln | Ile | His | Met | Met | Thr | Asp | Leu | Leu | Phe | Trp | Arg | Pro | Ala | Val |
|---|---|---|---|---|---|---|---|---|---|---|---|---|---|---|---|
| | | 355 | | | | 360 | | | | | | 365 | | | |

| Ala | Phe | Ala | Ser | Ala | Gln | Ser | His | Tyr | Ala | Pro | Val | Trp | Met | Tyr | Arg |
|---|---|---|---|---|---|---|---|---|---|---|---|---|---|---|---|
| | 370 | | | | | 375 | | | | | 380 | | | | |

| Phe | Asp | Trp | His | Pro | Glu | Lys | Pro | Pro | Tyr | Asn | Lys | Ala | Phe | His | Ala |
|---|---|---|---|---|---|---|---|---|---|---|---|---|---|---|---|
| 385 | | | | | 390 | | | | | 395 | | | | | 400 |

| Leu | Glu | Leu | Pro | Phe | Val | Phe | Gly | Asn | Leu | Asp | Gly | Leu | Glu | Arg | Met |
|---|---|---|---|---|---|---|---|---|---|---|---|---|---|---|---|
| | | | | 405 | | | | | 410 | | | | | 415 | |

| Ala | Lys | Ala | Glu | Ile | Thr | Asp | Glu | Val | Lys | Gln | Leu | Ser | His | Thr | Ile |
|---|---|---|---|---|---|---|---|---|---|---|---|---|---|---|---|
| | | | 420 | | | | | 425 | | | | | 430 | | |

| Gln | Ser | Ala | Trp | Ile | Thr | Phe | Ala | Lys | Thr | Gly | Asn | Pro | Ser | Thr | Glu |
|---|---|---|---|---|---|---|---|---|---|---|---|---|---|---|---|
| | | 435 | | | | | 440 | | | | | 445 | | | |

| Ala | Val | Asn | Trp | Pro | Ala | Tyr | His | Glu | Glu | Thr | Arg | Glu | Thr | Val | Ile |
|---|---|---|---|---|---|---|---|---|---|---|---|---|---|---|---|
| | 450 | | | | | 455 | | | | | 460 | | | | |

| Leu | Asp | Ser | Glu | Ile | Thr | Ile | Glu | Asn | Asp | Pro | Glu | Ser | Glu | Lys | Arg |
|---|---|---|---|---|---|---|---|---|---|---|---|---|---|---|---|
| 465 | | | | | 470 | | | | | 475 | | | | | 480 |

| Gln | Lys | Leu | Phe | Pro | Ser | Lys | Gly | Glu |
|---|---|---|---|---|---|---|---|---|
| | | | | 485 | | | | |

(2) INFORMATION FOR SEQ ID NO:5:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 2-19E10

(ix) FEATURE:
        (A) NAME/KEY: CDS
        (B) LOCATION: complement (1..1470)

(xi) SEQUENCE DESCRIPTION: SEQ ID NO:5:

```
ATGACTCATC  AAATAGTAAC  GACTCAATAC  GGCAAAGTAA  AAGGCACAAC  GGAAAACGGC    60
GTACATAAGT  GGAAAGGCAT  CCCTTATGCC  AAGCCGCCTG  TCGGACAATG  GCGTTTTAAA   120
GCACCTGAGC  CGCCTGAAGT  GTGGGAAGAT  GTCCTTGATG  CCACAGCGTA  CGGTCCTATT   180
TGCCCGCAGC  CGTCTGATTT  GCTCTCACTG  TCGTATACAG  AGCTGCCCCG  CCAGTCCGAG   240
GATTGCTTGT  ATGTCAATGT  ATTTGCGCCT  GACACTCCAA  GTCAAAATCT  TCCTGTCATG   300
GTGTGGATTC  ACGGAGGCGC  TTTTTATCTA  GGAGCGGGCA  GTGAGCCATT  GTATGACGGA   360
TCAAAACTTG  CGGCACAGGG  AGAAGTCATT  GTCGTTACAT  TGAACTATCG  GCTGGGGCCG   420
TTTGGCTTTT  TGCACTTGTC  TTCGTTTGAT  GAGGCGTATT  CCGATAACCT  TGGGCTTTTA   480
GACCAAGCCG  CCGCGCTGAA  ATGGGTGCGG  GAGAATATCT  CAGCGTTTGG  CGGTGATCCC   540
GATAACGTAA  CAGTATTTGG  AGAATCCGCC  GGCGGCATGA  GCATTGCCGC  GCTGCTCGCT   600
ATGCCTGCGG  CAAAAGGCCT  GTTCCAGAAA  GCGATCATGG  AAAGCGGCGC  TTCCCGAACA   660
ATGACAAAAG  AACAAGCGGC  AAGCACTGCG  GCTGCCTTTT  TACAGGTCCT  TGGGATTAAT   720
GAGAGCCAGC  TGGACAGATT  GCATACTGTA  GCAGCGGAAG  ATTTGCTTAA  AGCGGCCGAT   780
CAGCTTCGGA  TTGCAGAAAA  AGAAAATATC  TTTCAGCTGT  TCTTCCAGCC  CGCCCTTGAT   840
```

```
CCGAAAACGC TGCCTGAAGA ACCAGAAAAA TCGATCGCAG AAGGGGCTGC TTCCGGCATT      900
CCGCTATTGA TTGGAACAAC CCGTGATGAA GGATATTTAT TTTTCACCCC GGATTCAGAC      960
GTTCGTTCTC AGGAAACGCT TGATGCAGCA CTCGAGTATT TACTAGGGAA GCCGCTGGCA     1020
GAGAAAGCTG CCGATTTGTA TCCGCGTTCT CTGGAAAGCC AAATTCATAT GGTGACTGAT     1080
TTATTATTTT GGCGCCCTGC CGTCGCCTTT GCATCCGCAC AGTCTCATTA CGCCCCTGTC     1140
TGGATGTACC GGTTCGATTG GCACCCGGAG AAGCCGCCGT ACAATAAAGC GTTTCACGCA     1200
TTAGAGCTTC CTTTTGTCTT TGGAAATCTG GACGGGTTGG AACGAATGGC AAAAGCGGAG     1260
ATTACGGATG AGGTGAAACA GCTTTCTCAC ACGATACAAT CCGCGTGGAT CACGTTCGCT     1320
AAAACAGGAA ACCCAAGCAC CGAAGCTGTG AATTGGCCGG CGTATCATGA GAAACGAGA      1380
GAGACGGTGA TTTTAGACTC AGAGATTACG ATCGAAAACG ATCCCGAATC TGAAAAAGG      1440
CAGAAGCTAT TCCCTTCAAA AGGAGAATAA                                      1470
```

( 2 ) INFORMATION FOR SEQ ID NO:6:

( i ) SEQUENCE CHARACTERISTICS:
( A ) LENGTH: 489 amino acids
( B ) TYPE: amino acid
( D ) TOPOLOGY: linear ( i i ) MOLECULE TYPE: enzyme ( x i ) SEQUENCE DESCRIPTION: SEQ ID NO:6:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Pro Glu Val Trp
            35                  40                  45

Glu Asp Val Leu Asp Ala Thr Ala Tyr Gly Pro Ile Cys Pro Gln Pro
        50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240
```

| Glu | Ser | Gln | Leu | Asp | Arg | Leu | His | Thr | Val | Ala | Ala | Glu | Asp | Leu | Leu |
|---|---|---|---|---|---|---|---|---|---|---|---|---|---|---|---|
| | | | | 245 | | | | 250 | | | | | | 255 | |

| Lys | Ala | Ala | Asp | Gln | Leu | Arg | Ile | Ala | Glu | Lys | Glu | Asn | Ile | Phe | Gln |
|---|---|---|---|---|---|---|---|---|---|---|---|---|---|---|---|
| | | | 260 | | | | 265 | | | | | | 270 | | |

| Leu | Phe | Phe | Gln | Pro | Ala | Leu | Asp | Pro | Lys | Thr | Leu | Pro | Glu | Glu | Pro |
|---|---|---|---|---|---|---|---|---|---|---|---|---|---|---|---|
| | | 275 | | | | | 280 | | | | | 285 | | | |

| Glu | Lys | Ser | Ile | Ala | Glu | Gly | Ala | Ala | Ser | Gly | Ile | Pro | Leu | Leu | Ile |
|---|---|---|---|---|---|---|---|---|---|---|---|---|---|---|---|
| | 290 | | | | | 295 | | | | | 300 | | | | |

| Gly | Thr | Thr | Arg | Asp | Glu | Gly | Tyr | Leu | Phe | Phe | Thr | Pro | Asp | Ser | Asp |
|---|---|---|---|---|---|---|---|---|---|---|---|---|---|---|---|
| 305 | | | | | 310 | | | | | 315 | | | | | 320 |

| Val | Arg | Ser | Gln | Glu | Thr | Leu | Asp | Ala | Ala | Leu | Glu | Tyr | Leu | Leu | Gly |
|---|---|---|---|---|---|---|---|---|---|---|---|---|---|---|---|
| | | | | 325 | | | | 330 | | | | | 335 | | |

| Lys | Pro | Leu | Ala | Glu | Lys | Ala | Ala | Asp | Leu | Tyr | Pro | Arg | Ser | Leu | Glu |
|---|---|---|---|---|---|---|---|---|---|---|---|---|---|---|---|
| | | | 340 | | | | 345 | | | | | 350 | | | |

| Ser | Gln | Ile | His | Met | Val | Thr | Asp | Leu | Leu | Phe | Trp | Arg | Pro | Ala | Val |
|---|---|---|---|---|---|---|---|---|---|---|---|---|---|---|---|
| | | 355 | | | | 360 | | | | | 365 | | | | |

| Ala | Phe | Ala | Ser | Ala | Gln | Ser | His | Tyr | Ala | Pro | Val | Trp | Met | Tyr | Arg |
|---|---|---|---|---|---|---|---|---|---|---|---|---|---|---|---|
| | 370 | | | | | 375 | | | | | 380 | | | | |

| Phe | Asp | Trp | His | Pro | Glu | Lys | Pro | Pro | Tyr | Asn | Lys | Ala | Phe | His | Ala |
|---|---|---|---|---|---|---|---|---|---|---|---|---|---|---|---|
| 385 | | | | | 390 | | | | | 395 | | | | | 400 |

| Leu | Glu | Leu | Pro | Phe | Val | Phe | Gly | Asn | Leu | Asp | Gly | Leu | Glu | Arg | Met |
|---|---|---|---|---|---|---|---|---|---|---|---|---|---|---|---|
| | | | | 405 | | | | | 410 | | | | | 415 | |

| Ala | Lys | Ala | Glu | Ile | Thr | Asp | Glu | Val | Lys | Gln | Leu | Ser | His | Thr | Ile |
|---|---|---|---|---|---|---|---|---|---|---|---|---|---|---|---|
| | | | 420 | | | | | 425 | | | | | 430 | | |

| Gln | Ser | Ala | Trp | Ile | Thr | Phe | Ala | Lys | Thr | Gly | Asn | Pro | Ser | Thr | Glu |
|---|---|---|---|---|---|---|---|---|---|---|---|---|---|---|---|
| | | | 435 | | | | | 440 | | | | | 445 | | |

| Ala | Val | Asn | Trp | Pro | Ala | Tyr | His | Glu | Glu | Thr | Arg | Glu | Thr | Val | Ile |
|---|---|---|---|---|---|---|---|---|---|---|---|---|---|---|---|
| | 450 | | | | | 455 | | | | | 460 | | | | |

| Leu | Asp | Ser | Glu | Ile | Thr | Ile | Glu | Asn | Asp | Pro | Glu | Ser | Glu | Lys | Arg |
|---|---|---|---|---|---|---|---|---|---|---|---|---|---|---|---|
| 465 | | | | | 470 | | | | | 475 | | | | | 480 |

| Gln | Lys | Leu | Phe | Pro | Ser | Lys | Gly | Glu |
|---|---|---|---|---|---|---|---|---|
| | | | | 485 | | | | |

(2) INFORMATION FOR SEQ ID NO:7:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 3-10c4

(ix) FEATURE:
        (A) NAME/KEY: CDS
        (B) LOCATION: complement (1..1470)

(xi) SEQUENCE DESCRIPTION: SEQ ID NO:7:

```
ATGACTCATC AAATAGTAAC GACTCAATAC GGCAAAGTAA AAGGCACAAC GGAAAACGGC      60

GTACATAAGT GGAAAGGCAT CCCTTATGCC AAGCCGCCTG TCGGACAATG GCGTTTTAAA     120

GCACCTGAGC CGCCTGAAGT GTGGGAAGAT GTCCTTGATG CCACAGCGTA CGGTCCTATT     180

TGCCCGCAGC CGTCTGATTT GCTCTCACTG TCGTATACAG AGCTGCCCCG CCAGTCCGAG     240
```

| | | | | | |
|---|---|---|---|---|---|
| GATTGCTTGT | ATGTCAATGT | ATTTGCGCCT | GACACTCCAA | GTCAAAACCT | TCCTGTCATG | 300
| GTGTGGATTC | ACGGAGGCGC | TTTTTATCTA | GGAGCGGGCA | GTGAGCCATT | GTATGACGGA | 360
| TCAAAACTTG | CGGCACAGGG | AGAAGTCATT | GTCGTTACAT | TGAACTATCG | GCTGGGGCCG | 420
| TTTGGCTTTA | TGCACTTGTC | TTCGTTTGAT | GAGGCGTATT | CCGATAACCT | TGGGCTTTTA | 480
| GACCAAGCCG | CCGCGCTGAA | ATGGGTGCGG | GAGAATATCT | CAGCGTTTGG | CGGTGATCCC | 540
| GATAACGTAA | CAGTATTTGG | AGAATCCGCC | GGCGGCATGA | GCATTGCCGC | GCTGCTCGCT | 600
| ATGCCTGCGG | CAAAAGGCCT | GTTCCAGAAA | GCGATCATGG | AAAGCGGCGC | TTCCCGAACA | 660
| ATGACAAAAG | AACAAGCGGC | AAGCACTGCG | GCTGCCTTTT | TACAGGTCCT | TGGGATTAAT | 720
| GAGAGCCAGC | TGGACAGATT | GCATACTGTA | GCAGCGGAAG | ATTTGCTTAA | AGCGGCCGAT | 780
| CAGCTTCGGA | TTGCAGAAAA | AGAAAATATC | TTTCAGCTGT | CTTCCAGCC | CGCCCTTGAT | 840
| CCGAAAACGC | TGCCTGAAGA | ACCAGAAAAA | TCGATCGCAG | AAGGGGCTGC | TTCCGGCATT | 900
| CCGCTATTGA | TTGGAACAAC | CCGTGATGAA | GGATATTTAT | TTTTCACCCC | GGATTCAGAC | 960
| GTTCGTTCTC | AGGAAACGCT | TGATGCAGCA | CTCGAGTATT | TACTAGGGAA | GCCGCTGGCA | 1020
| GAGAAAGCTG | CCGATTTGTA | TCCGCGTTCT | CTGGAAAGCC | AAATTCATAT | GGTGACTGAT | 1080
| TTATTATTTT | GGCGCCCTGC | CGTCGCCTTT | GCATCCGCAC | AGTCTCATTA | CGCCCCTGTC | 1140
| TGGATGTACC | GGTTCGATTG | GCACCCGGAG | AAGCCGCCGT | ACAATAAAGC | GTTCACGCA | 1200
| TTAGAGCTTC | CTTTTGTCTT | TGGAAATCTG | GACGGGTTGG | AACGAATGGC | AAAAGCGGAG | 1260
| ATTACGGATG | AGGTGAAACA | GCTTTCTCAC | ACGATACAAT | CCGCGTGGAT | CACGTTCGCT | 1320
| AAAACAGGAA | ACCCAAGCAC | CGAAGCTGTG | AATTGGCCGG | CGTATCATGA | AGAAACGAGA | 1380
| GAGACGGTGA | TTTTAGACTC | AGAGATTACG | ATCGAAAACG | ATCCCGAATC | TGAAAAAGG | 1440
| CAGAAGCTAT | TCCCTTCAAA | AGGAGAATAA | | | | 1470

( 2 ) INFORMATION FOR SEQ ID NO:8:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: enzyme ( x i ) SEQUENCE DESCRIPTION: SEQ ID NO:8:

| Met | Thr | His | Gln | Ile | Val | Thr | Thr | Gln | Tyr | Gly | Lys | Val | Lys | Gly | Thr |
|---|---|---|---|---|---|---|---|---|---|---|---|---|---|---|---|
| 1 | | | | 5 | | | | | 10 | | | | | 15 | |
| Thr | Glu | Asn | Gly | Val | His | Leu | Trp | Lys | Gly | Ile | Pro | Tyr | Ala | Lys | Pro |
| | | | 20 | | | | | 25 | | | | | 30 | | |
| Pro | Val | Gly | Gln | Trp | Arg | Phe | Lys | Ala | Pro | Glu | Pro | Pro | Glu | Val | Trp |
| | | | 35 | | | | | 40 | | | | | 45 | | |
| Glu | Asp | Val | Leu | Asp | Ala | Thr | Ala | Tyr | Gly | Pro | Ile | Cys | Pro | Gln | Pro |
| | 50 | | | | | 55 | | | | | 60 | | | | |
| Ser | Asp | Leu | Leu | Ser | Leu | Ser | Tyr | Thr | Glu | Leu | Pro | Arg | Gln | Ser | Glu |
| 65 | | | | | 70 | | | | | 75 | | | | | 80 |
| Asp | Cys | Leu | Tyr | Val | Asn | Val | Phe | Ala | Pro | Asp | Thr | Pro | Ser | Gln | Asn |
| | | | | 85 | | | | | 90 | | | | | 95 | |
| Leu | Pro | Val | Met | Val | Trp | Ile | His | Gly | Gly | Ala | Phe | Tyr | Leu | Gly | Ala |
| | | | 100 | | | | | 105 | | | | | 110 | | |
| Gly | Ser | Glu | Pro | Leu | Tyr | Asp | Gly | Ser | Lys | Leu | Ala | Ala | Gln | Gly | Glu |
| | | | 115 | | | | | 120 | | | | | 125 | | |
| Val | Ile | Val | Val | Thr | Leu | Asn | Tyr | Arg | Leu | Gly | Pro | Phe | Gly | Phe | Met |

|   |   |   |   |   |   |   |   |   |   |   |   |   |   |   |
|---|---|---|---|---|---|---|---|---|---|---|---|---|---|---|
|   |   | 130 |   |   |   |   | 135 |   |   |   |   | 140 |   |   |
| His | Leu | Ser | Ser | Phe | Asp | Glu | Ala | Tyr | Ser | Asp | Asn | Leu | Gly | Leu | Leu |
| 145 |   |   |   |   | 150 |   |   |   | 155 |   |   |   |   | 160 |
| Asp | Gln | Ala | Ala | Ala | Leu | Lys | Trp | Val | Arg | Glu | Asn | Ile | Ser | Ala | Phe |
|   |   |   |   | 165 |   |   |   | 170 |   |   |   |   | 175 |   |
| Gly | Gly | Asp | Pro | Asp | Asn | Val | Thr | Val | Phe | Gly | Glu | Ser | Ala | Gly | Gly |
|   |   |   | 180 |   |   |   | 185 |   |   |   |   | 190 |   |   |
| Met | Ser | Ile | Ala | Ala | Leu | Leu | Ala | Met | Pro | Ala | Ala | Lys | Gly | Leu | Phe |
|   |   | 195 |   |   |   | 200 |   |   |   |   | 205 |   |   |   |
| Gln | Lys | Ala | Ile | Met | Glu | Ser | Gly | Ala | Ser | Arg | Thr | Met | Thr | Lys | Glu |
|   | 210 |   |   |   |   | 215 |   |   |   | 220 |   |   |   |   |
| Gln | Ala | Ala | Ser | Thr | Ala | Ala | Ala | Phe | Leu | Gln | Val | Leu | Gly | Ile | Asn |
| 225 |   |   |   |   | 230 |   |   |   | 235 |   |   |   |   | 240 |
| Glu | Ser | Gln | Leu | Asp | Arg | Leu | His | Thr | Val | Ala | Ala | Glu | Asp | Leu | Leu |
|   |   |   | 245 |   |   |   | 250 |   |   |   |   | 255 |   |   |
| Lys | Ala | Ala | Asp | Gln | Leu | Arg | Ile | Ala | Glu | Lys | Glu | Asn | Ile | Phe | Gln |
|   |   |   | 260 |   |   |   | 265 |   |   |   |   | 270 |   |   |
| Leu | Phe | Phe | Gln | Pro | Ala | Leu | Asp | Pro | Lys | Thr | Leu | Pro | Glu | Glu | Pro |
|   |   | 275 |   |   |   | 280 |   |   |   |   | 285 |   |   |   |
| Glu | Lys | Ser | Ile | Ala | Glu | Gly | Ala | Ala | Ser | Gly | Ile | Pro | Leu | Leu | Ile |
|   | 290 |   |   |   |   | 295 |   |   |   | 300 |   |   |   |   |
| Gly | Thr | Thr | Arg | Asp | Glu | Gly | Tyr | Leu | Phe | Phe | Thr | Pro | Asp | Ser | Asp |
| 305 |   |   |   |   | 310 |   |   |   | 315 |   |   |   |   | 320 |
| Val | Arg | Ser | Gln | Glu | Thr | Leu | Asp | Ala | Ala | Leu | Glu | Tyr | Leu | Leu | Gly |
|   |   |   |   | 325 |   |   |   | 330 |   |   |   |   | 335 |   |
| Lys | Pro | Leu | Ala | Glu | Lys | Ala | Ala | Asp | Leu | Tyr | Pro | Arg | Ser | Leu | Glu |
|   |   |   | 340 |   |   |   | 345 |   |   |   |   | 350 |   |   |
| Ser | Gln | Ile | His | Met | Val | Thr | Asp | Leu | Leu | Phe | Trp | Arg | Pro | Ala | Val |
|   |   | 355 |   |   |   |   | 360 |   |   |   |   | 365 |   |   |
| Ala | Phe | Ala | Ser | Ala | Gln | Ser | His | Tyr | Ala | Pro | Val | Trp | Met | Tyr | Arg |
|   | 370 |   |   |   |   | 375 |   |   |   |   | 380 |   |   |   |
| Phe | Asp | Trp | His | Pro | Glu | Lys | Pro | Pro | Tyr | Asn | Lys | Ala | Phe | His | Ala |
| 385 |   |   |   |   | 390 |   |   |   | 395 |   |   |   |   | 400 |
| Leu | Glu | Leu | Pro | Phe | Val | Phe | Gly | Asn | Leu | Asp | Gly | Leu | Glu | Arg | Met |
|   |   |   |   | 405 |   |   |   | 410 |   |   |   |   | 415 |   |
| Ala | Lys | Ala | Glu | Ile | Thr | Asp | Glu | Val | Lys | Gln | Leu | Ser | His | Thr | Ile |
|   |   |   | 420 |   |   |   | 425 |   |   |   |   | 430 |   |   |
| Gln | Ser | Ala | Trp | Ile | Thr | Phe | Ala | Lys | Thr | Gly | Asn | Pro | Ser | Thr | Glu |
|   |   | 435 |   |   |   | 440 |   |   |   |   | 445 |   |   |   |
| Ala | Val | Asn | Trp | Pro | Ala | Tyr | His | Glu | Glu | Thr | Arg | Glu | Thr | Val | Ile |
|   | 450 |   |   |   |   | 455 |   |   |   | 460 |   |   |   |   |
| Leu | Asp | Ser | Glu | Ile | Thr | Ile | Glu | Asn | Asp | Pro | Glu | Ser | Glu | Lys | Arg |
| 465 |   |   |   |   | 470 |   |   |   | 475 |   |   |   |   | 480 |
| Gln | Lys | Leu | Phe | Pro | Ser | Lys | Gly | Glu |
|   |   |   |   | 485 |

( 2 ) INFORMATION FOR SEQ ID NO:9:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( A ) ORGANISM:
    ( C ) INDIVIDUAL ISOLATE: 4-38b9

( i x ) FEATURE:
    ( A ) NAME/KEY: CDS
    ( B ) LOCATION: complement (1..1470)

( x i ) SEQUENCE DESCRIPTION: SEQ ID NO:9:

```
ATGACTCATC AAATAGTAAC GACTCAATAC GGCAAAGTAA AAGGCACAAC GGAAAACGGC      60
GTACATAAGT GGAAAGGCAT CCCTTATGCC AAGCCGCCTG TCGGACAATG GCGTTTTAAA     120
GCACCTGAGC CGCCTGAAGT GTGGGAAGAT GTCCTTGATG CCACAGCGTA CGGTCCTGTT     180
TGCCCGCAGC CGTCTGATTT GCTCTCACTG TCGTATACAG AGCTGCCCCG CCAGTCCGAG     240
GATTGCTTGT ATGTCAATGT ATTTGCGCCT GACACTCCAA GTCAAACCT TCCTGTCATG      300
GTGTGGATTC ACGGAGGCGC TTTTTATCTA GGAGCGGGCA GTGAGCCATT GTATGACGGA     360
TCAAAACTTG CGGCACAGGG AGAAGTCATT GTCGTTACAT GAACTATCG GCTGGGGCCG     420
TTTGGCTTTA TGCACTTGTC TTCGTTTGAT GAGGCGTATT CCGATAACCT TGGGCTTTTA    480
GACCAAGCCG CCGCGCTGAA ATGGGTGCGG GAGAATATCT CAGCGTTTGG CGGTGATCCC    540
GATAACGTAA CAGTATTTGG AGAATCCGCC GGCGGCATGA GCATTGCCGC GCTGCTCGCT    600
ATGCCTGCGG CAAAAGGCCT GTTCCAGAAA GCGATCATGG AAAGCGGCGC TTCCCGAACA    660
ATGACAAAAG AACAAGCGGC AAGCACTGCG GCTGCCTTTT TACAGGTCCT TGGGATTAAT    720
GAGAGCCAGC TGGACAGATT GCATACTGTA GCAGCGGAAG ATTTGCTTAA AGCGGCCGAT    780
CAGCTTCGGA TTGCAGAAAA AGAAAATATC TTTCAGCTGT CTTCCAGCC CGCCCTTGAT     840
CCGAAAACGC TGCCTGAAGA ACCAGAAAAA TCGATCGCAG AAGGGGCTGC TTCCGGCATT    900
CCGCTATTGA TTGGAACAAC CCGTGATGAA GGATATTTAT TTTTCACCCC GGATTCAGAC    960
GTTCGTTCTC AGGAAACGCT TGATGCAGCA CTCGAGTATT TACTAGGGAA GCCGCTGGCA   1020
GAGAAAGCTG CCGATTTGTA TCCGCGTTCT CTGGAAAGCC AAATTCATAT GGTGACTGAT    1080
TTATTATTTT GGCGCCCTGC CGTCGCCTTT GCATCCGCAC AGTCTCATTA CGCCCCTGTC   1140
TGGATGTACC GGTTCGATTG GCACCCGGAG AAGCCGCCGT ACAATAAAGC GTTTCACGCA   1200
TTAGAGCTTC CTTTTGTCTT TGGAAATCTG GACGGGTTGG AACGAATGGC AAAAGCGGAG    1260
ATTACGGATG AGGTGAAACA GCTTTCTCAC ACGATACAAT CCGCGTGGAT CACGTTCGCT    1320
AAAACAGGAA ACCCAAGCAC CGAAGCTGTG AATTGGCCGG CGTATCATGA AGAAACGAGA    1380
GAGACGGTGA TTTTAGACTC AGAGATTACG ATCGAAAACG ATCCCGAATC TGAAAAAAGG    1440
CAGAAGCTAT TCCCTTCAAA AGGAGAATAA                                     1470
```

( 2 ) INFORMATION FOR SEQ ID NO:10:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: enzyme ( x i ) SEQUENCE DESCRIPTION: SEQ ID NO:10:

```
Met Thr His Gln Ile Val Thr Thr Gln Tyr Gly Lys Val Lys Gly Thr
 1               5                  10                  15
Thr Glu Asn Gly Val His Leu Trp Lys Gly Ile Pro Tyr Ala Lys Pro
             20                  25                  30
```

-continued

Pro Val Gly Gln Trp Arg Phe Lys Ala Pro Glu Pro Glu Val Trp
         35                      40                45

Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
65                  70                  75                      80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Leu Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

( 2 ) INFORMATION FOR SEQ ID NO:11:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE: 4-43e7

( i x ) FEATURE:
        ( A ) NAME/KEY: CDS
        ( B ) LOCATION: complement (1..1470)

( x i ) SEQUENCE DESCRIPTION: SEQ ID NO:11:

```
ATGACTCATC AAATAGTAAC GACTCAATAC GGCAAAGTAA AAGGCACAAC GGAAAACGGC    60

GTACATAAGT GGAAAGGCAT CCCTTATGCC AAGCCGCCTG TCGGACAATG GCGTTTTAAA   120

GCACCTGAGC CGCCTGAAGT GTGGGAAGAT GTCCTTGATG CCACAGCGTA CGGTCCTATT   180

TGCCCGCAGC CGTCTGATTT GCTCTCACTG TCGTATACAG AGCTGCCCCG CCAGTCCGAG   240

GATTGCTTGT ATGTCAATGT ATTTGCGCCT GACACTCCAG GTCAAAACCT TCCTGTCATG   300

GTGTGGATTC ACGGAGGCGC TTTTTATCTA GGAGCGGGCA GTGAGCCATT GTATGACGGA   360

TCAAAACTTG CGGCACAGGG AGAAGTCATT GTCGTTACAT GAACTATCG GCTGGGGCCG   420

TTTGGCTTTA TGCACTTGTC TTCGTTTGAT GAGGCGTATT CCGATAACCT TGGGCTTTTA   480

GACCAAGCCG CCGCGCTGAA ATGGGTGCGG GAGAATATCT CAGCGTTTGG CGGTGATCCC   540

GATAACGTAA CAGTATTTGG AGAATCCGCC GGCGGCATGA GCATTGCCGC GCTGCTCGCT   600

ATGCCTGCGG CAAAAGGCCT GTTCCAGAAA GCGATCATGG AAAGCGGCGC TTCCCGAACA   660

ATGACAAAAG AACAAGCGGC AAGCACTGCG GCTGCCTTTT TACAGGTCCT TGGGATTAAT   720

GAGAGCCAGC TGGACAGATT GCATACTGTA GCAGCGGAAG ATTTGCTTAA AGCGGCCGAT   780

CAGCTTCGGA TTGCAGAAAA AGAAAATATC TTTCAGCTGT TCTTCCAGCC CGCCCTTGAT   840

CCGAAAACGC TGCCTGAAGA ACCAGAAAAA TCGATCGCAG AAGGGGCTGC TTCCGGCATT   900

CCGCTATTGA TTGGAACAAC CCGTGATGAA GGATATTTAT TTTCACCCC GGATTCAGAC   960

GTTCGTTCTC AGGAAACGCT TGATGCAGCA CTCGAGTATT TACTAGGGAA GCCGCTGGCA  1020

GAGAAAGCTG CCGATTTGTA TCCGCGTTCT CTGGAAAGCC AAATTCATAT GGTGACTGAT  1080

TTATTATTTT GGCGCCCTGC CGTCGCCTTT GCATCCGCAC AGTCTCATTA CGCCCCTGTC  1140

TGGATGTACC GGTTCGATTG CACCCGGAG AAGCCGCCGT ACAATAAAGC GTTTCACGCA  1200

TTAGAGCTTC CTTTTGTCTT TGGAAATCTG GACGGGTTGG AACGAATGGC AAAAGCGGAG  1260

ATTACGGATG AGGTGAAACA GCTTTCTCAC ACGATACAAT CCGCGTGGAT CACGTTCGCT  1320

AAAACAGGAA ACCCAAGCAC CGAAGCTGTG AATTGGCCGG CGTATCATGA AGAAACGAGA  1380

GAGACGGTGA TTTTAGACTC AGAGATTACG ATCGAAAACG ATCCCGAATC TGAAAAAAGG  1440
```

CAGAAGCTAT TCCCTTCAAA AGGAGAATAA                                    1470

( 2 ) INFORMATION FOR SEQ ID NO:12:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: enzyme ( x i ) SEQUENCE DESCRIPTION: SEQ ID NO:12:

```
Met  Thr  His  Gln  Ile  Val  Thr  Thr  Gln  Tyr  Gly  Lys  Val  Lys  Gly  Thr
  1                   5                  10                      15

Thr  Glu  Asn  Gly  Val  His  Leu  Trp  Lys  Gly  Ile  Pro  Tyr  Ala  Lys  Pro
                20                  25                      30

Pro  Val  Gly  Gln  Trp  Arg  Phe  Lys  Ala  Pro  Glu  Pro  Glu  Val  Trp
           35                       40                  45

Glu  Asp  Val  Leu  Asp  Ala  Thr  Ala  Tyr  Gly  Pro  Ile  Cys  Pro  Gln  Pro
     50                       55                  60

Ser  Asp  Leu  Leu  Ser  Leu  Ser  Tyr  Thr  Glu  Leu  Pro  Arg  Gln  Ser  Glu
 65                       70                  75                           80

Asp  Cys  Leu  Tyr  Val  Asn  Val  Phe  Ala  Pro  Asp  Thr  Pro  Gly  Gln  Asn
                     85                       90                       95

Leu  Pro  Val  Met  Val  Trp  Ile  His  Gly  Gly  Ala  Phe  Tyr  Leu  Gly  Ala
               100                      105                     110

Gly  Ser  Glu  Pro  Leu  Tyr  Asp  Gly  Ser  Lys  Leu  Ala  Ala  Gln  Gly  Glu
          115                      120                     125

Val  Ile  Val  Val  Thr  Leu  Asn  Tyr  Arg  Leu  Gly  Pro  Phe  Gly  Phe  Met
     130                      135                     140

His  Leu  Ser  Ser  Phe  Asp  Glu  Ala  Tyr  Ser  Asp  Asn  Leu  Gly  Leu  Leu
145                      150                     155                      160

Asp  Gln  Ala  Ala  Ala  Leu  Lys  Trp  Val  Arg  Glu  Asn  Ile  Ser  Ala  Phe
                165                      170                     175

Gly  Gly  Asp  Pro  Asp  Asn  Val  Thr  Val  Phe  Gly  Glu  Ser  Ala  Gly  Gly
          180                      185                     190

Met  Ser  Ile  Ala  Ala  Leu  Leu  Ala  Met  Pro  Ala  Ala  Lys  Gly  Leu  Phe
          195                      200                     205

Gln  Lys  Ala  Ile  Met  Glu  Ser  Gly  Ala  Ser  Arg  Thr  Met  Thr  Lys  Glu
     210                      215                     220

Gln  Ala  Ala  Ser  Thr  Ala  Ala  Ala  Phe  Leu  Gln  Val  Leu  Gly  Ile  Asn
225                      230                     235                      240

Glu  Ser  Gln  Leu  Asp  Arg  Leu  His  Thr  Val  Ala  Ala  Glu  Asp  Leu  Leu
                245                      250                     255

Lys  Ala  Ala  Asp  Gln  Leu  Arg  Ile  Ala  Glu  Lys  Glu  Asn  Ile  Phe  Gln
           260                      265                     270

Leu  Phe  Phe  Gln  Pro  Ala  Leu  Asp  Pro  Lys  Thr  Leu  Pro  Glu  Glu  Pro
          275                      280                     285

Glu  Lys  Ser  Ile  Ala  Glu  Gly  Ala  Ala  Ser  Gly  Ile  Pro  Leu  Leu  Ile
     290                      295                     300

Gly  Thr  Thr  Arg  Asp  Glu  Gly  Tyr  Leu  Phe  Phe  Thr  Pro  Asp  Ser  Asp
305                      310                     315                      320

Val  Arg  Ser  Gln  Glu  Thr  Leu  Asp  Ala  Ala  Leu  Glu  Tyr  Val  Leu  Gly
                325                      330                     335

Lys  Pro  Leu  Ala  Glu  Lys  Ala  Ala  Asp  Leu  Tyr  Pro  Arg  Ser  Leu  Glu
           340                      345                     350
```

| | | | | | | | | | | | | | |
|---|---|---|---|---|---|---|---|---|---|---|---|---|---|
|Ser|Gln|Ile<br>355|His|Met|Val|Thr|Asp<br>360|Leu|Leu|Phe|Trp|Arg<br>365|Pro|Ala|Val|
|Ala|Phe<br>370|Ala|Ser|Ala|Gln|Ser<br>375|His|Tyr|Ala|Pro|Val<br>380|Trp|Met|Tyr|Arg|
|Phe<br>385|Asp|Trp|His|Pro|Glu<br>390|Lys|Pro|Pro|Tyr|Asn<br>395|Lys|Ala|Phe|His|Ala<br>400|
|Leu|Glu|Leu|Pro|Phe<br>405|Val|Phe|Gly|Asn|Leu<br>410|Asp|Gly|Leu|Glu|Arg<br>415|Met|
|Ala|Lys|Ala|Glu<br>420|Ile|Thr|Asp|Glu|Val<br>425|Lys|Gln|Leu|Ser|His<br>430|Thr|Ile|
|Gln|Ser|Ala<br>435|Trp|Ile|Thr|Phe|Ala<br>440|Lys|Thr|Gly|Asn|Pro<br>445|Ser|Thr|Glu|
|Ala|Val|Asn<br>450|Trp|Pro|Ala|Tyr|His<br>455|Glu|Glu|Thr|Arg|Glu<br>460|Thr|Val|Ile|
|Leu|Asp<br>465|Ser|Glu|Ile|Thr|Ile<br>470|Glu|Asn|Asp|Pro|Glu<br>475|Ser|Glu|Lys|Arg<br>480|
|Gln|Lys|Leu|Phe|Pro<br>485|Ser|Lys|Gly|Glu| | | | | | | |

( 2 ) INFORMATION FOR SEQ ID NO:13:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE: 4-54b9

( i x ) FEATURE:
        ( A ) NAME/KEY: CDS
        ( B ) LOCATION: complement (1..1470)

( x i ) SEQUENCE DESCRIPTION: SEQ ID NO:13:

```
ATGACTCATC AAATAGTAAC GACTCAATAC GGCAAAGTAA AAGGCACAAC GGAAAACGGC    60
GTACATAAGT GGAAAGGCAT CCCTTATGCC AAGCCGCCCG TCGGACAATG GCGTTTTAAA   120
GCACCTGAGC CGCCTGAAGT GTGGGAAGAT GTCCTTGATG CCACAGCGTA CGGTCCTATT   180
TGCCCGCAGC CGTCTGATTT GCTCTCACTG TCGTATACAG AGCTGCCCCG CCAGTCCGAG   240
GATTGCTTGT ATGTCAATGT ATTTGCGCCT GACACTCCAA GTCAAAACCT TCCTGTCATG   300
GTGTGGATTC ACGGAGGCGC TTTTTATCTA GGAGCGGGCA GTGAGCCATT GTATGACGGA   360
TCAAAACTTG CGGCACAGGG AGAAGTCATT GTCGTTACAT GAACTATCG GCTGGGGCCG    420
TTTGGCTTTA TGCACTTGTC TTCGTTTGAT GAGGCGTATT CCGATAACCT TGGGCTTTTA   480
GACCAAGCCG CCGCGCTGAA ATGGGTGCGG GAGAATATCT CAGCGTTTGG CGGTGATCCC   540
GATAACGTAA CAGTATTTGG AGAATCCGCC GGCGGCATGA GCATTGCCGC GCTGCTCGCT   600
ATGCCTGCGG CAAAAGGCCT GTTCCAGAAA GCGATCATGG AAAGCGGCGC TTCCCGAACA   660
ATGACAAAAG AACAAGCGGC AAGCACTGCG GCTGCCTTTT TACAGGTCCT TGGGATTAAT   720
GAGAGCCAGC TGGACAGATT GCATACTGTA GCAGCGGAAG ATTTGCTTAA GCGGCCGAT    780
CAGCTTCGGA TTGCAGAAAA AGAAATATC TTTCAGCTGT TCTTCCAGCC CGCCCTTGAT    840
```

```
CCGAAAACGC TGCCTGAAGA ACCAGAAAAA TCGATCGCAG AAGGGGCTGC TTCCGGCATT      900
CCGCTATTGA TTGGAACAAC CCGTGATGAA GGATATTTAT TTTTCACCCC GGATTCAGAC      960
GTTCGTTCTC AGGAAACGCT TGATGCAGCA CTCGAGTATT TACTAGGGAA GCCGCTGGCA     1020
GAGAAAGCTG CCGATTTGTA TCCGCGTTCT CTGGAAAGCC AAATTCATAT GGTGACTGAT     1080
TTATTATTTT GGCGCCCTGC CGTCGCCTTT GCATCCGCAC AGTCTCATTA CGCCCCTGTC     1140
TGGATGTACC GGTTCGATTG CACCCGGAG  AAGCCGCCGT ACAATAAAGC GTTTCACGCA     1200
TTAGAGCTTC CTTTTGTCTT TGGAAATCTG GACGGGTTGG AACGAATGGC AAAAGCGGAG     1260
ATTACGGATG AGGTGAAACA GCTTTCTCAC ACGATACAAT CCGCGTGGAT CACGTTCGCT     1320
AAAACAGGAA ACCCAAGCAC CGAAGCTGTG AATTGGCCGG CGTATCATGA AGAAACGAGA     1380
GAGACGGTGA TTTTAGACTC AGAGATTACG ATCGAAAACG ATCCGAATC  TGAAAAAAGG     1440
CAGAAGCTAT TCCCTTCAAA AGGAGAATAA                                     1470
```

(2) INFORMATION FOR SEQ ID NO:14:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:14:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Pro Glu Val Trp
            35                  40                  45

Glu Asp Val Leu Asp Ala Thr Ala Tyr Gly Pro Ile Cys Pro Gln Pro
 50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
210                 215                 220

Gln Ala Ala Ser Thr Ala Ala Ala Phe Leu Gln Val Leu Gly Ile Asn
225                 230                 235                 240
```

| Glu | Ser | Gln | Leu | Asp | Arg | Leu | His | Thr | Val | Ala | Ala | Glu | Asp | Leu | Leu |
|---|---|---|---|---|---|---|---|---|---|---|---|---|---|---|---|
| | | | | 245 | | | | 250 | | | | | | 255 | |

| Lys | Ala | Ala | Asp | Gln | Leu | Arg | Ile | Ala | Glu | Arg | Glu | Asn | Ile | Phe | Gln |
|---|---|---|---|---|---|---|---|---|---|---|---|---|---|---|---|
| | | | 260 | | | | 265 | | | | | 270 | | | |

| Leu | Phe | Phe | Gln | Pro | Ala | Leu | Asp | Pro | Lys | Thr | Leu | Pro | Glu | Glu | Pro |
|---|---|---|---|---|---|---|---|---|---|---|---|---|---|---|---|
| | | 275 | | | | | 280 | | | | | 285 | | | |

| Glu | Lys | Ser | Ile | Ala | Glu | Gly | Ala | Ala | Ser | Gly | Ile | Pro | Leu | Leu | Ile |
|---|---|---|---|---|---|---|---|---|---|---|---|---|---|---|---|
| | 290 | | | | | 295 | | | | | 300 | | | | |

| Gly | Thr | Thr | Arg | Asp | Glu | Gly | Tyr | Leu | Phe | Phe | Thr | Pro | Asp | Ser | Asp |
|---|---|---|---|---|---|---|---|---|---|---|---|---|---|---|---|
| 305 | | | | | 310 | | | | | 315 | | | | | 320 |

| Val | Arg | Ser | Gln | Glu | Thr | Leu | Asp | Ala | Ala | Leu | Glu | Tyr | Ser | Leu | Gly |
|---|---|---|---|---|---|---|---|---|---|---|---|---|---|---|---|
| | | | | 325 | | | | | 330 | | | | | 335 | |

| Lys | Pro | Leu | Ala | Glu | Lys | Ala | Ala | Asp | Leu | Tyr | Pro | Arg | Ser | Leu | Glu |
|---|---|---|---|---|---|---|---|---|---|---|---|---|---|---|---|
| | | | 340 | | | | | 345 | | | | | 350 | | |

| Ser | Gln | Ile | His | Met | Val | Thr | Asp | Leu | Leu | Phe | Trp | Arg | Pro | Ala | Val |
|---|---|---|---|---|---|---|---|---|---|---|---|---|---|---|---|
| | | 355 | | | | | 360 | | | | | 365 | | | |

| Ala | Phe | Ala | Ser | Ala | Gln | Ser | His | Tyr | Ala | Pro | Val | Trp | Met | Tyr | Arg |
|---|---|---|---|---|---|---|---|---|---|---|---|---|---|---|---|
| | 370 | | | | | 375 | | | | | 380 | | | | |

| Phe | Asp | Trp | His | Pro | Glu | Lys | Pro | Pro | Tyr | Asn | Lys | Ala | Phe | His | Ala |
|---|---|---|---|---|---|---|---|---|---|---|---|---|---|---|---|
| 385 | | | | | 390 | | | | | 395 | | | | | 400 |

| Leu | Glu | Leu | Pro | Phe | Val | Phe | Gly | Asn | Leu | Asp | Gly | Leu | Glu | Arg | Met |
|---|---|---|---|---|---|---|---|---|---|---|---|---|---|---|---|
| | | | | 405 | | | | | 410 | | | | | 415 | |

| Ala | Lys | Ala | Glu | Ile | Thr | Asp | Glu | Val | Lys | Gln | Leu | Ser | His | Thr | Ile |
|---|---|---|---|---|---|---|---|---|---|---|---|---|---|---|---|
| | | | 420 | | | | | 425 | | | | | 430 | | |

| Gln | Ser | Ala | Trp | Ile | Thr | Phe | Ala | Lys | Thr | Gly | Asn | Pro | Ser | Thr | Glu |
|---|---|---|---|---|---|---|---|---|---|---|---|---|---|---|---|
| | | 435 | | | | | 440 | | | | | 445 | | | |

| Ala | Val | Asn | Trp | Pro | Ala | Tyr | His | Glu | Glu | Thr | Arg | Glu | Thr | Val | Ile |
|---|---|---|---|---|---|---|---|---|---|---|---|---|---|---|---|
| | 450 | | | | | 455 | | | | | 460 | | | | |

| Leu | Asp | Ser | Glu | Ile | Thr | Ile | Glu | Asn | Asp | Pro | Glu | Ser | Glu | Lys | Arg |
|---|---|---|---|---|---|---|---|---|---|---|---|---|---|---|---|
| 465 | | | | | 470 | | | | | 475 | | | | | 480 |

| Gln | Lys | Leu | Phe | Pro | Ser | Lys | Gly | Glu |
|---|---|---|---|---|---|---|---|---|
| | | | | 485 | | | | |

( 2 ) INFORMATION FOR SEQ ID NO:15:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE: 2-13f3

( i x ) FEATURE:
        ( A ) NAME/KEY: CDS
        ( B ) LOCATION: complement (1..1470)

( x i ) SEQUENCE DESCRIPTION: SEQ ID NO:15:

| ATGACTCATC | AAATAGTAAC | GACTCAATAC | GGCAAAGTAA | AAGGCACAAC | GGAAAACGGC | 60 |
| GTACATAAGT | GGAAAGGCAT | CCCTTATGCC | AAGCCGCCTG | TCGGACAATG | GCGTTTTAAA | 120 |
| GCACCTGAGC | CGCCTGAAGT | GTGGGAAGAT | GTCCTTGATG | CCACAGCGTA | CGGTCCTATT | 180 |
| TGCCCGCAGC | CGTCTGATTT | GCTCTCACTG | TCGTATACAG | AGCTGCCCCG | CCAGTCCGAG | 240 |

| | | | | | |
|---|---|---|---|---|---|
| GATTGCTTGT | ATGTCAATGT | ATTTGCGCCT | GACACTCCAA | GTCAAAGTCT | TCCTGTCATG | 300
| GTGTGGATTC | ACGGAGGCGC | TTTTTATCTT | GGAGCGGGCA | GTGAGCCATT | GTATGACGGA | 360
| TCAAAACTTG | CGGCACAGGG | AGAAGTCATT | GTCGTTACAT | TGAACTATCG | GCTGGGGCCG | 420
| TTTGGCTTTT | TGCACTTGTC | TTCGTTTGAT | GAGGCGTATT | CCGATAACCT | GGGCTTTTA | 480
| GACCAAGCCG | CCGCGCTGAA | ATGGGTGCGG | GAGAATATCT | CAGCGTTTGG | CGGTGATCCC | 540
| GATAACGTAA | CAGTATTTGG | AGAATCCGCC | GGCGGCATGA | GCATTGCCGC | GCTGCTCGCT | 600
| ATGCCTGCGG | CAAAAGGCCT | GTTCCAGAAA | GCGATCATGG | AAAGCGGCGC | TTCCCGAACA | 660
| ATGACAAAAG | AACAAGCGGC | AAGCACTGCG | GCTGCCTTTT | TACAGGTCCT | TGGGATTAAT | 720
| GAGAGCCAGC | TGGACAGATT | GCATACTGTA | GCAGCGGAAG | ATTTGCTTAA | AGCGGCCGAT | 780
| CAGCTTCGGA | TTGCAGAAAA | AGAAAATATC | TTTCAGCTGT | TCTTCCAGCC | CGCCCTTGAT | 840
| CCGAAAACGC | TGCCTGAAGA | ACCAGAAAAA | TCGATCGCAG | AAGGGGCTGC | TTCCGGCATT | 900
| CCGCTATTGA | TTGGAACAAC | CCGTGATGAA | GGATATTTAT | TTTCACCCC | GGATTCAGAC | 960
| GTTCGTTCTC | AGGAAACGCT | TGATGCAGCA | CTCGAGTATT | TACTAGGGAA | GCCGCTGGCA | 1020
| GAGAAAGCTG | CCGATTTGTA | TCCGCGTTCT | CTGGAAAGCC | AAATTCATAT | GGTGACTGAT | 1080
| TTATTATTTT | GGCGCCCTGC | CGTCGCCTTT | GCATCCGCGC | AGTCTCATTA | CGCCCCTGTC | 1140
| TGGATGTACC | GGTTCGATTG | GCACCCGGAG | AAGCCGCCGT | ACAATAAAGC | GTTCACGCA | 1200
| TTAGAGCTTC | CTTTTGTCTT | TGGGAATCTG | GACGGATTGG | AACGAATGGC | AAAAGCGGAG | 1260
| ATTACGGATG | AGGTGAAACA | GCTTTCTCAC | ACGATACAGT | CCGCGTGGAT | CACGTTCGCT | 1320
| AAAACAGGAA | ACCCAAGCAC | CGAAGCTGTG | AATTGGCCGG | CGTATCATGA | AGAAACGAGA | 1380
| GAGACGGTGA | TTTTAGACTC | AGAGATTACG | ATCGAAAACG | ATCCCGAATC | TGAAAAAAGG | 1440
| CAGAAGCTAT | TCCCTTCAAA | AGGAGAATAA | | | | 1470

( 2 ) INFORMATION FOR SEQ ID NO:16:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: enzyme ( x i ) SEQUENCE DESCRIPTION: SEQ ID NO:16:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Glu Val Trp
             35                  40                  45

Glu Asp Val Leu Asp Ala Thr Ala Tyr Gly Pro Ile Cys Pro Gln Pro
     50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Ser
                 85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
```

|     |     |     |     |     | 130 |     |     |     | 135 |     |     |     |     | 140 |     |
|---|---|---|---|---|---|---|---|---|---|---|---|---|---|---|---|

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
            165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200             205

Gln Lys Ala Ile Met Glu Ser Gly Ala Ser Arg Thr Met Thr Lys Glu
    210             215                 220

Gln Ala Ala Ser Thr Ala Ala Phe Leu Gln Val Leu Gly Ile Asn
225             230             235                 240

Glu Ser Gln Leu Asp Arg Leu His Thr Val Ala Ala Glu Asp Leu Leu
            245             250             255

Lys Ala Ala Asp Gln Leu Arg Ile Ala Glu Lys Glu Asn Ile Phe Gln
        260             265             270

Leu Phe Phe Gln Pro Ala Leu Asp Pro Lys Thr Leu Pro Glu Glu Pro
    275             280             285

Glu Lys Ser Ile Ala Glu Gly Ala Ala Ser Gly Ile Pro Leu Leu Ile
    290             295             300

Gly Thr Thr Arg Asp Glu Gly Tyr Leu Phe Phe Thr Pro Asp Ser Asp
305             310             315             320

Val Arg Ser Gln Glu Thr Leu Asp Ala Ala Leu Glu Tyr Leu Leu Gly
            325             330             335

Lys Pro Leu Ala Glu Lys Ala Ala Asp Leu Tyr Pro Arg Ser Leu Glu
        340             345             350

Ser Gln Ile His Met Val Thr Asp Leu Leu Phe Trp Arg Pro Ala Val
        355             360             365

Ala Phe Ala Ser Ala Gln Ser His Tyr Ala Pro Val Trp Met Tyr Arg
    370             375             380

Phe Asp Trp His Pro Glu Lys Pro Pro Tyr Asn Lys Ala Phe His Ala
385             390             395             400

Leu Glu Leu Pro Phe Val Phe Gly Asn Leu Asp Gly Leu Glu Arg Met
            405             410             415

Ala Lys Ala Glu Ile Thr Asp Glu Val Lys Gln Leu Ser His Thr Ile
        420             425             430

Gln Ser Ala Trp Ile Thr Phe Ala Lys Thr Gly Asn Pro Ser Thr Glu
        435             440             445

Ala Val Asn Trp Pro Ala Tyr His Glu Glu Thr Arg Glu Thr Val Ile
    450             455             460

Leu Asp Ser Glu Ile Thr Ile Glu Asn Asp Pro Glu Ser Glu Lys Arg
465             470             475             480

Gln Lys Leu Phe Pro Ser Lys Gly Glu
            485

( 2 ) INFORMATION FOR SEQ ID NO:17:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO (iv) ANTI-SENSE: NO (vi) ORIGINAL SOURCE:
    (A) ORGANISM:
    (C) INDIVIDUAL ISOLATE: 2-23e1

(ix) FEATURE:
    (A) NAME/KEY: CDS
    (B) LOCATION: complement (1..1470)

(xi) SEQUENCE DESCRIPTION: SEQ ID NO:17:

| | | | | | |
|---|---|---|---|---|---|
| ATGACTCATC | AAATAGTAAC | GACTCAATAC | GGCAAAGTAA | AAGGCACAAC | GGAAAACGGC | 60 |
| GTACATAAGT | GGAAAGGCAT | CCCTTATGCC | AAGCCGCCTG | TCGGACAATG | GCGTTTTAAA | 120 |
| GCACCTGAGC | CGCCTGAAGT | GTGGGAAGAT | GTCCTTGATG | CCACAGCGTA | CGGTCCTATT | 180 |
| TGCCCGCAGC | CGTCTGATTT | GCTCTCACTG | TCGTATACAG | AGCTGCCCCG | CCAGTCCGAG | 240 |
| GATTGCTTGT | ATGTCAATGT | ATTTGCGCCT | GACACTCCAA | GTCAAATCT | TCCTGTCATG | 300 |
| GTGTGGATTC | ACGGAGGCGC | TTTTTATCTT | GGAGCGGGCA | GTGAGCCATT | GTATGACGGA | 360 |
| TCAAAACTTG | CGGCACAGGG | AGAAGTCATT | GTCGTCACAT | TGAACTATCG | GCTGGGGCCG | 420 |
| TTTGGCTTTT | TGCACTTGTC | TTCGTTTGAT | GAGGCGTATT | CCGATAACCT | TGGGCTTTTA | 480 |
| GACCAAGCCG | CCGCGCTGAA | ATGGGTGCGG | GAGAATATCT | CAGCGTTTGG | CGGTGATCCC | 540 |
| GATAACGTAA | CAGTATTTGG | AGAATCCGCC | GGCGGCATGA | GCATTGCCGC | GCTGCTCGCT | 600 |
| ATGCCTGCGG | CAAAAGGCCT | GTTCCAGAAA | GCGATCATGG | AAAGCGGCGC | TTCCCGAACA | 660 |
| ATGACAAAAG | AACAAGCGGC | AAGCACTGCG | GCTGCCTTTT | TACAGGTCCT | TGGGATTAAT | 720 |
| GAGAGCCAGC | TGGACAGATT | GCATACTGTA | GCAGCGGAAG | ATTTGCTTAA | AGCGGCCGAT | 780 |
| CAGCTTCGGA | TTGCAGAAAA | AGAAAATATC | CTTCAGCTGT | TCTTCCAGCC | CGCCCTTGAT | 840 |
| CCGAAAACGC | TGCCTGAAGA | ACCAGAAAAA | TCGATCGCAG | AAGGGGCTGC | TTCCGGCATT | 900 |
| CCGCTATTGA | TTGGAACAAC | CCGTGATGAA | GGATATTTAT | TTTCACCCC | GGATTCAGAC | 960 |
| GTTCGTTCTC | AGGAAACGCT | TGATGCAGCA | CTCGAGTATT | TACTAGGGAA | GCCGCTGGCA | 1020 |
| GAGAAAGTTG | CCGATTTGTA | TCCGCGTTCT | CTGGAAAGCC | AAATTCATAT | GATGACTGAT | 1080 |
| TTATTATTTT | GGCGCCCTGC | CGTCGCCTTT | GCATCCGCAC | AGTCTCATTA | CGCCCCTGTC | 1140 |
| TGGATGTACC | GGTTCGATTG | GCACCCGGAG | AAGCCGCCGT | ACAATAAAGC | GTTTCACGCA | 1200 |
| TTAGAGCTTC | CTTTTGTCTT | TGGAAATCTG | GACGGATTGG | AACGAATGGC | AAAAGCGGAG | 1260 |
| ATTACGGATG | AGGTGAAACA | GCTTTCTCAC | ACGATACAAT | CCGCGTGGAT | CACGTTCGCT | 1320 |
| AAAACAGGAA | ACCCAAGCAC | CGAAGCTGTG | AATTGGCCGG | CGTATCATGA | AGAAACGAGA | 1380 |
| GAGACGGTGA | TTTAGACTC | AGAGATTACG | ATCGAAAACG | ATCCCGAATC | TGAAAAAAGG | 1440 |
| CAGAAGCTAT | TCCCTTCAAA | AGGAGAATAA | | | | 1470 |

(2) INFORMATION FOR SEQ ID NO:18:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:18:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
            20                  25                  30
```

-continued

| Pro | Val | Gly | Gln | Trp | Arg | Phe | Lys | Ala | Pro | Glu | Pro | Glu | Val | Trp |
|---|---|---|---|---|---|---|---|---|---|---|---|---|---|---|
| | | 35 | | | | 40 | | | | 45 | | | | |

| Glu | Asp | Val | Leu | Asp | Ala | Thr | Ala | Tyr | Gly | Pro | Ile | Cys | Pro | Gln | Pro |
|---|---|---|---|---|---|---|---|---|---|---|---|---|---|---|---|
| | 50 | | | | | 55 | | | | | 60 | | | | |

| Ser | Asp | Leu | Leu | Ser | Leu | Ser | Tyr | Thr | Glu | Leu | Pro | Arg | Gln | Ser | Glu |
|---|---|---|---|---|---|---|---|---|---|---|---|---|---|---|---|
| 65 | | | | | 70 | | | | | 75 | | | | | 80 |

| Asp | Cys | Leu | Tyr | Val | Asn | Val | Phe | Ala | Pro | Asp | Thr | Pro | Ser | Gln | Asn |
|---|---|---|---|---|---|---|---|---|---|---|---|---|---|---|---|
| | | | | 85 | | | | | 90 | | | | | 95 | |

| Leu | Pro | Val | Met | Val | Trp | Ile | His | Gly | Gly | Ala | Phe | Tyr | Leu | Gly | Ala |
|---|---|---|---|---|---|---|---|---|---|---|---|---|---|---|---|
| | | | 100 | | | | | 105 | | | | | 110 | | |

| Gly | Ser | Glu | Pro | Leu | Tyr | Asp | Gly | Ser | Lys | Leu | Ala | Ala | Gln | Gly | Glu |
|---|---|---|---|---|---|---|---|---|---|---|---|---|---|---|---|
| | | 115 | | | | | 120 | | | | | 125 | | | |

| Val | Ile | Val | Val | Thr | Leu | Asn | Tyr | Arg | Leu | Gly | Pro | Phe | Gly | Phe | Leu |
|---|---|---|---|---|---|---|---|---|---|---|---|---|---|---|---|
| | 130 | | | | | 135 | | | | | 140 | | | | |

| His | Leu | Ser | Ser | Phe | Asp | Glu | Ala | Tyr | Ser | Asp | Asn | Leu | Gly | Leu | Leu |
|---|---|---|---|---|---|---|---|---|---|---|---|---|---|---|---|
| 145 | | | | | 150 | | | | | 155 | | | | | 160 |

| Asp | Gln | Ala | Ala | Ala | Leu | Lys | Trp | Val | Arg | Glu | Asn | Ile | Ser | Ala | Phe |
|---|---|---|---|---|---|---|---|---|---|---|---|---|---|---|---|
| | | | | 165 | | | | | 170 | | | | | 175 | |

| Gly | Gly | Asp | Pro | Asp | Asn | Val | Thr | Val | Phe | Gly | Glu | Ser | Ala | Gly | Gly |
|---|---|---|---|---|---|---|---|---|---|---|---|---|---|---|---|
| | | | 180 | | | | | 185 | | | | | 190 | | |

| Met | Ser | Ile | Ala | Ala | Leu | Leu | Ala | Met | Pro | Ala | Ala | Lys | Gly | Leu | Phe |
|---|---|---|---|---|---|---|---|---|---|---|---|---|---|---|---|
| | | 195 | | | | | 200 | | | | | 205 | | | |

| Gln | Lys | Ala | Ile | Met | Glu | Ser | Gly | Ala | Ser | Arg | Thr | Met | Thr | Lys | Glu |
|---|---|---|---|---|---|---|---|---|---|---|---|---|---|---|---|
| | 210 | | | | | 215 | | | | | 220 | | | | |

| Gln | Ala | Ala | Ser | Thr | Ala | Ala | Ala | Phe | Leu | Gln | Val | Leu | Gly | Ile | Asn |
|---|---|---|---|---|---|---|---|---|---|---|---|---|---|---|---|
| 225 | | | | | 230 | | | | | 235 | | | | | 240 |

| Glu | Ser | Gln | Leu | Asp | Arg | Leu | His | Thr | Val | Ala | Ala | Glu | Asp | Leu | Leu |
|---|---|---|---|---|---|---|---|---|---|---|---|---|---|---|---|
| | | | | 245 | | | | | 250 | | | | | 255 | |

| Lys | Ala | Ala | Asp | Gln | Leu | Arg | Ile | Ala | Glu | Lys | Glu | Asn | Ile | Leu | Gln |
|---|---|---|---|---|---|---|---|---|---|---|---|---|---|---|---|
| | | | 260 | | | | | 265 | | | | | 270 | | |

| Leu | Phe | Phe | Gln | Pro | Ala | Leu | Asp | Pro | Lys | Thr | Leu | Pro | Glu | Glu | Pro |
|---|---|---|---|---|---|---|---|---|---|---|---|---|---|---|---|
| | 275 | | | | | 280 | | | | | 285 | | | | |

| Glu | Lys | Ser | Ile | Ala | Glu | Gly | Ala | Ala | Ser | Gly | Ile | Pro | Leu | Leu | Ile |
|---|---|---|---|---|---|---|---|---|---|---|---|---|---|---|---|
| | 290 | | | | | 295 | | | | | 300 | | | | |

| Gly | Thr | Thr | Arg | Asp | Glu | Gly | Tyr | Leu | Phe | Phe | Thr | Pro | Asp | Ser | Asp |
|---|---|---|---|---|---|---|---|---|---|---|---|---|---|---|---|
| 305 | | | | | 310 | | | | | 315 | | | | | 320 |

| Val | Arg | Ser | Gln | Glu | Thr | Leu | Asp | Ala | Ala | Leu | Glu | Tyr | Leu | Leu | Gly |
|---|---|---|---|---|---|---|---|---|---|---|---|---|---|---|---|
| | | | | 325 | | | | | 330 | | | | | 335 | |

| Lys | Pro | Leu | Ala | Glu | Lys | Val | Ala | Asp | Leu | Tyr | Pro | Arg | Ser | Leu | Glu |
|---|---|---|---|---|---|---|---|---|---|---|---|---|---|---|---|
| | | | 340 | | | | | 345 | | | | | 350 | | |

| Ser | Gln | Ile | His | Met | Met | Thr | Asp | Leu | Leu | Phe | Trp | Arg | Pro | Ala | Val |
|---|---|---|---|---|---|---|---|---|---|---|---|---|---|---|---|
| | | 355 | | | | | 360 | | | | | 365 | | | |

| Ala | Phe | Ala | Ser | Ala | Gln | Ser | His | Tyr | Ala | Pro | Val | Trp | Met | Tyr | Arg |
|---|---|---|---|---|---|---|---|---|---|---|---|---|---|---|---|
| | 370 | | | | | 375 | | | | | 380 | | | | |

| Phe | Asp | Trp | His | Pro | Glu | Lys | Pro | Pro | Tyr | Asn | Lys | Ala | Phe | His | Ala |
|---|---|---|---|---|---|---|---|---|---|---|---|---|---|---|---|
| 385 | | | | | 390 | | | | | 395 | | | | | 400 |

| Leu | Glu | Leu | Pro | Phe | Val | Phe | Gly | Asn | Leu | Asp | Gly | Leu | Glu | Arg | Met |
|---|---|---|---|---|---|---|---|---|---|---|---|---|---|---|---|
| | | | | 405 | | | | | 410 | | | | | 415 | |

| Ala | Lys | Ala | Glu | Ile | Thr | Asp | Glu | Val | Lys | Gln | Leu | Ser | His | Thr | Ile |
|---|---|---|---|---|---|---|---|---|---|---|---|---|---|---|---|
| | | | 420 | | | | | 425 | | | | | 430 | | |

| Gln | Ser | Ala | Trp | Ile | Thr | Phe | Ala | Lys | Thr | Gly | Asn | Pro | Ser | Thr | Glu |
|---|---|---|---|---|---|---|---|---|---|---|---|---|---|---|---|
| | | 435 | | | | | 440 | | | | | 445 | | | |

| Ala | Val | Asn | Trp | Pro | Ala | Tyr | His | Glu | Glu | Thr | Arg | Glu | Thr | Val | Ile |
|---|---|---|---|---|---|---|---|---|---|---|---|---|---|---|---|

| | | | |
|---|---|---|---|
| | 450 | 455 | 460 |

Leu Asp Ser Glu Ile Thr Ile Glu Asn Asp Pro Glu Ser Glu Lys Arg
465 470 475 480

Gln Lys Leu Phe Pro Ser Lys Gly Glu
485

( 2 ) INFORMATION FOR SEQ ID NO:19:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE: 4-53d5

( i x ) FEATURE:
        ( A ) NAME/KEY: CDS
        ( B ) LOCATION: complement (1..1470)

( x i ) SEQUENCE DESCRIPTION: SEQ ID NO:19:

| | | | | | | |
|---|---|---|---|---|---|---|
| ATGACTCATC | AAATAGTAAC | GACTCAATAC | GGCAAAGTAA | AAGGCACAAC | GGAAAACGGC | 60 |
| GTACATAAGT | GGAAAGGCAT | CCCTTATGCC | AAGCCGCCTG | TCGGACAATG | GCGTTTTAAA | 120 |
| GCACCTGAGC | CGCCTGAAGT | GTGGGAAGAT | GTCCTTGATG | CCACAGCGTA | CGGTCCTATT | 180 |
| TGCCCGCAGC | CGTCTGATTT | GCTCTCACTG | TCGTATACAG | AGCTGCCCCG | CCAGTCCGAG | 240 |
| GATTGCTTGT | ACGTCAATGT | ATTTGCGCCT | GACACTCCAA | GTCAAAACCT | TCCTGTCATG | 300 |
| GTGTGGATTC | ACGGAGGCGC | TTTTTATCTA | GGAGCGGGCA | GTGAGCCATT | GTATGACGGA | 360 |
| TCAAAACTTG | CGGCACAGGG | AGAAGTCATT | GTCGTTACAT | TGAACTATCG | GCTGGGGCCG | 420 |
| TTTGGCTTTA | TGCACTTGTC | TTCGTTTGAT | GAGGCGTATT | CCGATAACCT | TGGGCTTTTA | 480 |
| GACCAAGCCG | CCGCGCTGAA | ATGGGTGCGG | GAGAATATCT | CAGCGTTTGG | CGGTGATCCC | 540 |
| GATAACGTAA | CAGTATTTGG | AGAATCCGCC | GGCGGCATGA | GCATTGCCGC | GCTGCTCGCT | 600 |
| ATGCCTGCGG | CAAAAGGCCT | GTTCCAGAAA | GCGATCATGG | AAAGCGGCGC | TTCCCGAACA | 660 |
| ATGACAAAAG | AACAAGCGGC | AAGCACTGCG | GCTGCCTTTT | TACAGGTCCT | TGGGATCAAT | 720 |
| GAGAGCCAGC | TGGACAGATT | GCATACTGTA | GCAGCGGAAG | ATTTGCTTAA | AGCGGCCGAT | 780 |
| CAGCTTCGGA | TTGCAGAAAA | AGAAAATATC | TTTCAGCTGT | TCTTCCAGCC | CGCCCTTGAT | 840 |
| CCGAAAACGC | TGCCTGAAGA | ACCAGAAAAA | TCGATCGCAG | AAGGGGCTGC | TTCCGGCATT | 900 |
| CCGCTATTGA | TTGGAACAAC | CCGTGATGAA | GGATATTTAT | TTTTCACCCC | GGATTCAGAC | 960 |
| GTTCGTTCTC | AGGAAACGCT | TGATGCAGCA | CTCGAGTATT | TACTAGGGAA | GCCGCTGGCA | 1020 |
| GAGAAAGTTG | CCGATTTGTA | TCCGCGTTCT | CTGGAAAGCC | AAATTCATAT | GGTGACTGAT | 1080 |
| TTATTATTTT | GGCGCCCTGC | CGTCGCCTTT | GCATCCGCAC | AGTCTCATTA | CGCCCCTGTC | 1140 |
| TGGATGTACC | GGTTCGATTG | GCACCCGGAG | AAGCCGCCGT | ACAATAAAGC | GTTTCACGCA | 1200 |
| TTAGAGCTTC | CTTTTGTCTT | TGGAAATCTG | GACGGGTTGG | AACGAATGGC | AAAAGCGGAG | 1260 |
| ATTACGGATG | AGGTGAAACA | GCTTTCTCAC | ACGATACAAT | CCGCGTGGAT | CACGTTCGCT | 1320 |
| AAAACAGGAA | ACCCAAGCAC | CGAAGCTGTG | AATTGGCCGG | CGTATCATGA | AGAAACGAGA | 1380 |
| GAGACGGTGA | TTTTAGACTC | AGAGATTACG | ATCGAAACG | ATCCCGAATC | TGAAAAAAGG | 1440 |

CAGAAGCTAT TCCCTTCAAA AGGAGAATAA                             1470

( 2 ) INFORMATION FOR SEQ ID NO:20:

( i ) SEQUENCE CHARACTERISTICS:
        ( A ) LENGTH: 489 amino acids
        ( B ) TYPE: amino acid
        ( D ) TOPOLOGY: linear ( i i ) MOLECULE TYPE: enzyme ( x i ) SEQUENCE DESCRIPTION: SEQ ID NO:20:

```
Met Thr His Gln Ile Val Thr Thr Gln Tyr Gly Lys Val Lys Gly Thr
 1               5                  10                  15
Thr Glu Asn Gly Val His Leu Trp Lys Gly Ile Pro Tyr Ala Lys Pro
                20                  25                  30
Pro Val Gly Gln Trp Arg Phe Lys Ala Pro Glu Pro Pro Val Trp
        35                  40                  45
Glu Asp Val Leu Asp Ala Thr Ala Tyr Gly Pro Ile Cys Pro Gln Pro
        50                  55                  60
Ser Asp Leu Leu Ser Leu Ser Tyr Thr Glu Leu Pro Arg Gln Ser Glu
65                  70                  75                  80
Asp Cys Leu Tyr Val Asn Val Phe Ala Pro Asp Thr Pro Ser Gln Asn
                85                  90                  95
Leu Pro Val Met Val Trp Ile His Gly Gly Ala Phe Tyr Leu Gly Ala
                100                 105                 110
Gly Ser Glu Pro Leu Tyr Asp Gly Ser Lys Leu Ala Ala Gln Gly Glu
        115                 120                 125
Val Ile Val Val Thr Leu Asn Tyr Arg Leu Gly Pro Phe Gly Phe Met
    130                 135                 140
His Leu Ser Ser Phe Asp Glu Ala Tyr Ser Asp Asn Leu Gly Leu Leu
145                 150                 155                 160
Asp Gln Ala Ala Ala Leu Lys Trp Val Arg Glu Asn Ile Ser Ala Phe
                165                 170                 175
Gly Gly Asp Pro Asp Asn Val Thr Val Phe Gly Glu Ser Ala Gly Gly
        180                 185                 190
Met Ser Ile Ala Ala Leu Leu Ala Met Pro Ala Ala Lys Gly Leu Phe
        195                 200                 205
Gln Lys Ala Ile Met Glu Ser Gly Ala Ser Arg Thr Met Thr Lys Glu
    210                 215                 220
Gln Ala Ala Ser Thr Ala Ala Ala Phe Leu Gln Val Leu Gly Ile Asn
225                 230                 235                 240
Glu Ser Gln Leu Asp Arg Leu His Thr Val Ala Ala Glu Asp Leu Leu
                245                 250                 255
Lys Ala Ala Asp Gln Leu Arg Ile Ala Glu Lys Glu Asn Ile Phe Gln
                260                 265                 270
Leu Phe Phe Gln Pro Ala Leu Asp Pro Lys Thr Leu Pro Glu Glu Pro
        275                 280                 285
Glu Lys Ser Ile Ala Glu Gly Ala Ala Ser Gly Ile Pro Leu Leu Ile
    290                 295                 300
Gly Thr Thr Arg Asp Glu Gly Tyr Leu Phe Phe Thr Pro Asp Ser Asp
305                 310                 315                 320
Val Arg Ser Gln Glu Thr Leu Asp Ala Ala Leu Glu Tyr Leu Leu Gly
                325                 330                 335
Lys Pro Leu Ala Glu Lys Val Ala Asp Leu Tyr Pro Arg Ser Leu Glu
                340                 345                 350
```

|  |  |  |  |  |  |  |  |  |  |  |  |  |  |
|---|---|---|---|---|---|---|---|---|---|---|---|---|---|
| Ser | Gln | Ile<br>355 | His | Met | Val | Thr | Asp<br>360 | Leu | Leu | Phe | Trp<br>365 | Arg | Pro | Ala | Val |
| Ala | Phe<br>370 | Ala | Ser | Ala | Gln | Ser<br>375 | His | Tyr | Ala | Pro | Val<br>380 | Trp | Met | Tyr | Arg |
| Phe<br>385 | Asp | Trp | His | Pro | Glu<br>390 | Lys | Pro | Pro | Tyr | Asn<br>395 | Lys | Ala | Phe | His | Ala<br>400 |
| Leu | Glu | Leu | Pro | Phe<br>405 | Val | Phe | Gly | Asn | Leu<br>410 | Asp | Gly | Leu | Glu | Arg<br>415 | Met |
| Ala | Lys | Ala | Glu<br>420 | Ile | Thr | Asp | Glu | Val<br>425 | Lys | Gln | Leu | Ser | His<br>430 | Thr | Ile |
| Gln | Ser | Ala<br>435 | Trp | Ile | Thr | Phe | Ala<br>440 | Lys | Thr | Gly | Asn | Pro<br>445 | Ser | Thr | Glu |
| Ala | Val<br>450 | Asn | Trp | Pro | Ala | Tyr<br>455 | His | Glu | Glu | Thr | Arg<br>460 | Glu | Thr | Val | Ile |
| Leu<br>465 | Asp | Ser | Glu | Ile | Thr<br>470 | Ile | Glu | Asn | Asp | Pro<br>475 | Glu | Ser | Glu | Lys | Arg<br>480 |
| Gln | Lys | Leu | Phe | Pro<br>485 | Ser | Lys | Gly | Glu |  |  |  |  |  |  |  |

( 2 ) INFORMATION FOR SEQ ID NO:21:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE: 5-1a12

( i x ) FEATURE:
        ( A ) NAME/KEY: CDS
        ( B ) LOCATION: complement (1..1470)

( x i ) SEQUENCE DESCRIPTION: SEQ ID NO:21:

| | | | | | |
|---|---|---|---|---|---|
| ATGACTCATC | AAATAGTAAC | GACTCAATAC | GGCAAAGTAA | AAGGCACAAC | GGAAAACGGC | 60 |
| GTACATAAGT | GGAAAGGCAT | CCCTTATGCC | AAGCCGCCTG | TCGGACAATG | GCGTTTTAAA | 120 |
| GCACCTGAGC | CGCCTGAAGT | GTGGGAAGAT | GTCCTTGATG | CCACAGCGTA | CGGTCCTGTT | 180 |
| TGCCCGCAGC | CGTCTGATTT | GCTCTCACTG | TCGTATACAG | AGCTGCCCCG | CCAGTCCGAG | 240 |
| GATTGCTTGT | ATGTCAATGT | ATTTGCGCCT | GACACTCCAA | GTCAAAACCT | TCCTGTCATG | 300 |
| GTGTGGATTC | ACGGAGGCGC | TTTTTATCTA | GGAGCGGGCA | GTGAGCCATT | GTATGACGGA | 360 |
| TCAAAACTTG | CGGCACAGGG | AGAAGTCATT | GTCGTTACAT | TGAACTATCG | GCTGGGGCCG | 420 |
| TTTGGCTTTA | TGCACTTGTC | TTCGTTTGAT | GAGGCGTATT | CCGATAACCT | TGGGCTTTTA | 480 |
| GACCAAGCCG | CCGCGCTGAA | ATGGGTGCGG | GAGAATATCT | CAGCGTTTGG | CGGTGATCCC | 540 |
| GATAACGTAA | CAGTATTTGG | AGAATCCGCC | GGCGGCATGA | GCATTGCCGC | GCTGCTCGCT | 600 |
| ATGCCTGCGG | CAAAAGGCCT | GTTCCAGAAA | GCGATCATGG | AAAGCGGCGC | TTCCCGAACA | 660 |
| ATGACAAAAG | AACAAGCGGC | AAGCACTGCG | GCTGCCTTTT | TACAGGTCCT | TGGGATTAAT | 720 |
| GAGAGCCAGC | TGGACAGATT | GCATACTGTA | GCAGCGGAAG | ATTTGCTTAA | AGCGGCCGAT | 780 |
| CAGCTTCGGA | TTGCAGAAAA | AGAAAATATC | TTTCAGCTGT | TCTTCCAGCC | CGCCCTTGAT | 840 |

```
CCGAAAACGC TGCCTGAAGA ACCAGAAAAA TCGATCGCAG AAGGGGCTGC TTCCGGCATT       900
CCGCTATTGA TTGGAACAAC CCGTGATGAA GGATATTTAT TTTTCACCCC GGATTCAGAC       960
GTTCGTTCTC AGGAAACGCT TGATGCAGCA CTCGAGTATT TACTAGGGAA GCCGCTGGCA      1020
GAGAAAGCTG CCGATTTGTA TCCGCGTTCT CTGGAAAGCC AAATTCATAT GGTGACTGAT      1080
TTATTATTTT GGCGCCCTGC CGTCGCCTTT GCATCCGCAC AGTCTCATTA CGCCCCTGTC      1140
TGGATGTACC GGTTCGATTG GCACCCGGAG AAGCCGCCGT ACAATAAAGC GTTTCACGCA      1200
TTAGAGCTTC CTTTTGTCTT TGGAAATCTG GACGGGTTGG AACGAATGGC AAAAGCGGAG      1260
ATTACGGATG AGGTGAAACA GCTTTCTCAC ACGATACAAT CCGCGTGGAT CACGTTCGCT      1320
AAAACAGGAA ACCCAAGCAC CGAAGCTGTG AATTGGCCGG CGTATCATGA AGAAACGAGA      1380
GAGACGGTGA TTTTAGACTC AGAGATTACG ATCGAAAACG ATCCCGAATC TGAAAAAGG       1440
CAGAAGCTAT TCCCTTCAAA AGGAGAATAA                                       1470
```

(2) INFORMATION FOR SEQ ID NO:22:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:22:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Pro Glu Val Trp
            35                  40                  45

Glu Asp Val Leu Asp Ala Thr Ala Tyr Gly Pro Val Cys Pro Gln Pro
        50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Met
        130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240
```

| | | | | | | | | | | | | | |
|---|---|---|---|---|---|---|---|---|---|---|---|---|---|
| Glu | Ser | Gln | Leu | Asp<br>245 | Arg | Leu | His | Thr<br>250 | Val | Ala | Ala | Glu | Asp<br>255 | Leu | Leu |
| Lys | Ala | Ala | Asp<br>260 | Gln | Leu | Arg | Ile<br>265 | Ala | Glu | Lys | Glu | Asn<br>270 | Ile | Phe | Gln |
| Leu | Phe | Phe<br>275 | Gln | Pro | Ala | Leu | Asp<br>280 | Pro | Lys | Thr | Leu | Pro<br>285 | Glu | Glu | Pro |
| Glu | Lys<br>290 | Ser | Ile | Ala | Glu | Gly<br>295 | Ala | Ala | Ser | Gly | Ile<br>300 | Pro | Leu | Leu | Ile |
| Gly<br>305 | Thr | Thr | Arg | Asp | Glu<br>310 | Gly | Tyr | Leu | Phe | Phe<br>315 | Thr | Pro | Asp | Ser | Asp<br>320 |
| Val | Arg | Ser | Gln | Glu<br>325 | Thr | Leu | Asp | Ala<br>330 | Ala | Leu | Glu | Tyr | Ser<br>335 | Leu | Gly |
| Lys | Pro | Leu | Ala<br>340 | Glu | Lys | Ala | Ala<br>345 | Asp | Leu | Tyr | Pro | Arg<br>350 | Ser | Leu | Glu |
| Ser | Gln | Ile<br>355 | His | Met | Val | Thr | Asp<br>360 | Leu | Leu | Phe | Trp | Arg<br>365 | Pro | Ala | Val |
| Ala | Phe<br>370 | Ala | Ser | Ala | Gln | Ser<br>375 | His | Tyr | Ala | Pro | Val<br>380 | Trp | Met | Tyr | Arg |
| Phe<br>385 | Asp | Trp | His | Pro | Glu<br>390 | Lys | Pro | Pro | Tyr | Asn<br>395 | Lys | Ala | Phe | His | Ala<br>400 |
| Leu | Glu | Leu | Pro | Phe<br>405 | Val | Phe | Gly | Asn | Leu<br>410 | Asp | Gly | Leu | Glu | Arg<br>415 | Met |
| Ala | Lys | Ala | Glu<br>420 | Ile | Thr | Asp | Glu | Val<br>425 | Lys | Gln | Leu | Ser | His<br>430 | Thr | Ile |
| Gln | Ser | Ala<br>435 | Trp | Ile | Thr | Phe | Ala<br>440 | Lys | Thr | Gly | Asn | Pro<br>445 | Ser | Thr | Glu |
| Ala | Val<br>450 | Asn | Trp | Pro | Ala | Tyr<br>455 | His | Glu | Glu | Thr | Arg<br>460 | Glu | Thr | Val | Ile |
| Leu | Asp<br>465 | Ser | Glu | Ile | Thr<br>470 | Ile | Glu | Asn | Asp | Pro<br>475 | Glu | Ser | Glu | Lys | Arg<br>480 |
| Gln | Lys | Leu | Phe | Pro<br>485 | Ser | Lys | Gly | Glu | | | | | | | |

( 2 ) INFORMATION FOR SEQ ID NO:23:

( i ) SEQUENCE CHARACTERISTICS:
        ( A ) LENGTH: 1470 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE: consensus ( i x ) FEATURE:
        ( A ) NAME/KEY: CDS
        ( B ) LOCATION: complement (1..1470)

( x i ) SEQUENCE DESCRIPTION: SEQ ID NO:23:

| | | | | | | |
|---|---|---|---|---|---|---|
| ATGACTCATC | AAATAGTAAC | GACTCAATAC | GGCAAAGTAA | AAGGCACAAC | GGAAAACGGC | 60 |
| GTACATAAGT | GGAAAGGCAT | CCCNTATGCC | AAGCCGCCNG | TCGGACAATG | GCGTTTTAAA | 120 |
| GCACCTGAGC | CGCCTGAAGT | GTGGGAAGAT | GTCCTTGATG | CCACAGCGTA | CGGTCCTNTT | 180 |
| TGCCCGCAGC | CGTCTGATTT | GCTCTCACTG | TCGTATACAG | AGCTGCCCCG | CCAGTCCGAG | 240 |

| | | | | | |
|---|---|---|---|---|---|
| GATTGCTTGT | ANGTCAATGT | ATTTGCGCCT | GACACTCCAN | GTCAAANNCT | TCCTGTCATG | 300
| GTGTGGATTC | ACGGAGGCGC | TTTTTATCTN | GGAGCGGGCA | GTGAGCCATT | GTATGACGGA | 360
| TCAAAACTTG | CGGCACAGGG | AGAAGTCATT | GTCGTNACAT | TGAACTATCG | GCTGGGGCCG | 420
| TTTGGCTTTN | TGCACTTGTC | TTCGTTTGAT | GAGGCGTATT | CCGATAACCT | TGGGCTTTTA | 480
| GACCAAGCCG | CCGCGCTGAA | ATGGGTGCGG | GAGAATATCT | CAGCGTTTGG | CGGTGATCCC | 540
| GATAACGTAA | CAGTATTTGG | AGAATCCGCC | GGCGGCATGA | GCATTGCCGC | GCTGCTCGCT | 600
| ATGCCTGCGG | CAAAAGGCCT | GTTCCAGAAA | GCGATCATGG | AAAGCGGCGC | TTCCCGAACA | 660
| ATGACAAAAG | AACAAGCGGC | AAGCACTGCG | GCTGCCTTTT | TACAGGTCCT | TGGGATNAAT | 720
| GAGAGCCAGC | TGGACAGATT | GCATACTGTA | GCAGCGGAAG | ATTTGCTTAA | AGCGGCCGAT | 780
| CAGCTTCGGA | TTGCAGAAAA | AGAAAATATC | NTTCAGCTGT | TCTTCCAGCC | CGCCCTTGAT | 840
| CCGAAAACGC | TGCCTGAAGA | ACCAGAAAAA | TCGATCGCAG | AAGGGGCTGC | TTCCGGCATT | 900
| CCGCTATTGA | TTGGAACAAC | CCGTGATGAA | GGATATTTAT | TTTTCACCCC | GGATTCAGAC | 960
| GTTCNTTCTC | AGGAAACGCT | TGATGCAGCA | CTCGAGTATT | TACTAGGGAA | GCCGCTGGCA | 1020
| GAGAAAGNTG | CCGATTTGTA | TCCGCGTTCT | CTGGAAAGCC | AAATTCATAT | GNTGACTGAT | 1080
| TTATTATTTT | GGCGCCCTGC | CGTCGCCTNT | GCATCCGCNC | AGTCTCATTA | CGCCCCTGTC | 1140
| TGGATGTACC | GGTTCGATTG | GCACCCGGAG | AAGCCGCCGT | ACAATAAAGC | GTTCACGCA | 1200
| TTAGAGCTTC | CTTTTGTCTT | TGGNAATCTG | GACGGNTTGG | AACGAATGGC | AAAAGCGGAG | 1260
| ATTACGGATG | AGGTGAAACA | GCTTTCTCAC | ACGATACANT | CCGCGTGGAT | CACGTTCGCT | 1320
| AAAACAGGAA | ACCCAAGCAC | CGAAGCTGTG | AATTGGCCGG | CGTATCATGA | AGAAACGAGA | 1380
| GAGACGGTGA | TTTTAGACTC | AGAGATTACG | ATCGAAAACG | ATCCCGAATC | TGAAAAAGG | 1440
| CAGAAGCTAT | TCCCTTCAAA | AGGAGAATAA | | | | 1470

(2) INFORMATION FOR SEQ ID NO:24:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:24:

```
Met Thr His Gln Ile Val Thr Thr Gln Tyr Gly Lys Val Lys Gly Thr
  1               5                  10                  15

Thr Glu Asn Gly Val His Leu Trp Lys Gly Ile Pro Tyr Ala Lys Pro
                 20                  25                  30

Pro Val Gly Gln Trp Arg Phe Lys Ala Pro Glu Pro Pro Glu Val Trp
             35                  40                  45

Glu Asp Val Leu Asp Ala Thr Ala Tyr Gly Pro Xaa Cys Pro Gln Pro
         50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Xaa Gln Xaa
                 85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Xaa
```

|     |     |     | 130 |     |     |     | 135 |     |     |     | 140 |     |     |     |
| --- | --- | --- | --- | --- | --- | --- | --- | --- | --- | --- | --- | --- | --- | --- |
| His 145 | Leu | Ser | Ser | Phe | Asp 150 | Glu | Ala | Tyr | Ser | Asp 155 | Asn | Leu | Gly | Leu 160 |
| Asp | Gln | Ala | Ala | Ala 165 | Leu | Lys | Trp | Val | Arg 170 | Glu | Asn | Ile | Ser | Ala Phe 175 |
| Gly | Gly | Asp | Pro 180 | Asp | Asn | Val | Thr | Val 185 | Phe | Gly | Glu | Ser | Ala 190 | Gly Gly |
| Met | Ser | Ile 195 | Ala | Ala | Leu | Leu | Ala 200 | Met | Pro | Ala | Ala | Lys 205 | Gly | Leu Phe |
| Gln | Lys 210 | Ala | Ile | Met | Glu | Ser 215 | Gly | Ala | Ser | Arg | Thr 220 | Met | Thr | Lys Glu |
| Gln 225 | Ala | Ala | Ser | Thr | Ala 230 | Ala | Ala | Phe | Leu | Gln 235 | Val | Leu | Gly | Ile Asn 240 |
| Glu | Ser | Gln | Leu | Asp 245 | Arg | Leu | His | Thr | Val 250 | Ala | Ala | Glu | Asp | Leu Leu 255 |
| Lys | Ala | Ala | Asp 260 | Gln | Leu | Arg | Ile | Ala 265 | Glu | Xaa | Glu | Asn | Ile 270 | Xaa Gln |
| Leu | Phe | Phe 275 | Gln | Pro | Ala | Leu | Asp 280 | Pro | Lys | Thr | Leu | Pro 285 | Glu | Glu Pro |
| Glu | Lys 290 | Ser | Ile | Ala | Glu | Gly 295 | Ala | Ala | Ser | Gly | Ile 300 | Pro | Leu | Leu Ile |
| Gly 305 | Thr | Thr | Arg | Asp | Glu 310 | Gly | Tyr | Leu | Phe | Phe 315 | Thr | Pro | Asp | Ser Asp 320 |
| Val | Xaa | Ser | Gln | Glu 325 | Thr | Leu | Asp | Ala | Ala 330 | Leu | Glu | Tyr | Xaa | Leu Gly 335 |
| Lys | Pro | Leu | Ala 340 | Glu | Lys | Xaa | Ala | Asp 345 | Leu | Tyr | Pro | Arg | Ser 350 | Leu Glu |
| Ser | Gln | Ile 355 | His | Met | Xaa | Thr | Asp 360 | Leu | Leu | Phe | Trp | Arg 365 | Pro | Ala Val |
| Ala | Xaa 370 | Ala | Ser | Ala | Gln | Ser 375 | His | Tyr | Ala | Pro | Val 380 | Trp | Met | Tyr Arg |
| Phe 385 | Asp | Trp | His | Pro | Glu 390 | Lys | Pro | Pro | Tyr | Asn 395 | Lys | Ala | Phe | His Ala 400 |
| Leu | Glu | Leu | Pro | Phe 405 | Val | Phe | Gly | Asn | Leu 410 | Asp | Gly | Leu | Glu | Arg Met 415 |
| Ala | Lys | Ala | Glu 420 | Ile | Thr | Asp | Glu | Val 425 | Lys | Gln | Leu | Ser | His 430 | Thr Ile |
| Gln | Ser | Ala 435 | Trp | Ile | Thr | Phe | Ala 440 | Lys | Thr | Gly | Asn | Pro 445 | Ser | Thr Glu |
| Ala | Val 450 | Asn | Trp | Pro | Ala | Tyr 455 | His | Glu | Glu | Thr | Arg 460 | Glu | Thr | Val Ile |
| Leu 465 | Asp | Ser | Glu | Ile | Thr 470 | Ile | Glu | Asn | Asp | Pro 475 | Glu | Ser | Glu | Lys Arg 480 |
| Gln | Lys | Leu | Phe | Pro 485 | Ser | Lys | Gly | Glu |     |     |     |     |     |     |

BIBLIOGRAPHY

1. H. Waldmann and D. Sebastian, Enzymatic Protecting Group Techniques, Chem. Rev. 1994, 94, 911–937.

2. Kametani, T., T. Honda, A. Nakayama, K. Fukumoto. Facile Synthesis of Carbapenem antibiotics. The first and simple stereoselective synthesis of antibiotic PS-5 benzyl ester. Heterocycles 14, 1967–1971 (1980).

3. Brannon, D. R., Mabe, J. A., and Fukuda, D. S. (1976). De-esterification of cephalosporin para-nitrobenzyl esters by microbial enzymes. J. Antibiotics 29:121–124.

4. Zock, J., Cantwell, C., Swartling, J., Hodges, R., Pohl, T., Sutton, K., Rosteck Jr., P., McGilvray, D., and Queener, S. (1994) The *Bacillus subtilis* pnbA gene encoding p-nitrobenzyl esterase—cloning, sequence and high-level expression in *Escherichia coli*. Gene 151:37–43.

5. Cooper, R. D. G. (1992). The carbacephems: a new beta-lactam antibiotic class. Am. J. Med. 92:6A/2S-6A/6S.

6. Chen, Y., Usui, S., Queener, S. W. and Yu, C. (1995). Purification and properties of p-nitrobenzyl esterase from *Bacillus subtilis*. J. Ind. Micro. 15:10–18.

7. Chen, K. and Arnold, F. (1991). Enzyme engineering for nonaqueous solvents—random mutagenesis to enhance activity of subtilisin E in polar organic media. Bio/Technology 9:1073–1077.

8. Chen, K. and Arnold, F. (1993). Tuning the activity of an enzyme for unusual environments: sequential random mutagenesis of subtilisin E for catalysis in dimethylformamide. Proc. Natl. Aced. Sci. USA 90:5618–5622.

9. You, L. and Arnold, F. H. (1995). Directed Evolution of Subtilisin E in Bacillus Subtilis to Enhance Total Activity in Aqueous Dimethylformamide, Protein Engineering, in press.

10. Leung, D. W., Chen, E., and Goeddel, D. V. (1989). A method for random mutagenesis of a defined DNA segment using a modified polymerase chain reaction. Technique 1:11–15.

11. Eckert, K. A. and Kunkel, T. A. (1991). DNA polymerase fidelity and the polymerase chain reaction. PCR Methods Applic. 1:17–24.

12. Cadwell, R. C., and Joyce, G. F. (1992). Randomization of genes by PCR mutagenesis. PCR Methods and Appl.:28–33.

13. Arnold, F. H. (1991). Metal-affinity separations—a new dimension in protein processing. Bio/Technology 9:151–156.

14. Todd, R. J., Johnson, R. D. and Arnold, F. H. (1994). Multiple-site binding interactions in metal-affinity chromatography. 1. Equilibrium binding of engineered histidine-containing cytochrome-c. J. Chromat A 662:13–26.

15. Pohlenz, H. D., Boidol, W., Schuttke, I., and Streber, W. R. (1992). Purification and properties of an arthrobacter-oxydans p52 carbamate hydrolase specific for the herbicide phenmedipham and nucleotide-sequence of the corresponding gene. J. Bact. 174:6600–6607.

16. Tamura, N., Matsushita, Y., Iwama, T., Harada, S., Kishimoto, S. and Itoh, K. (1991), Synthesis and biological activity of (S)-2-amino-3-(2,5-dihydro-5-oxo-4-isoxazolyl) propanoic acid (TAN-950 A) derivatives, Chem. Pharm. Bull. 39:1199–212.

17. Garg, H. G. and Jeanloz, R. W. (1974), Synthesis of protected glycopeptides containing the amino acid sequences 34–37 and 34–38 of bovine ribonuclease B, Carbohyd. Res. 32:37–46.

18. Egan, L. P. (1972), Synthesis and acid-catalyzed hydrolysis of 3-0-glycosyl-L-serine and threonine, Carbohyd. Res. 23:261–73.

19. Hirayama, C., Ihara, H. and Shiraga, R. (1991), Induction of left-handed helical arrangement of 4-nitrobenzyl ester residues in cast film from poly(L-glutamate) by using a cationic bilayer forming compound, Chem. Lett. 8:1369–72.

20. Abiko, T. and Sekino, H. (1990), Synthesis of a thymosin $\beta_4$-like peptide, thymosin $\beta_9^{Met}$, and its effect on low E-rosette-forming lymphocytes of lupus nephritis patients, Chem. Pharm. Bull. 38:2301–4.

21. Suzuki, K. and Endo, N. (1978), The β-p-nitrobenzyl ester to minimize side reaction during treatment of aspartyl peptides with methanesulfonic acid, Chem. Pharm. Bull. 26:2269–74.

22. Barrett, G. C., Hardy, P. M., Harrow, T. A. and Rydon, H. N. (1972), Polypeptides. XXII. Synthesis of peptides of α-benzylphenylalanine by the dicyclohexycarbodiimide method. J. Chem. Soc., Perkin Trans. 1 20:2634–8.

23. Hruby, V. J., Ferger, M. F. and Du Vigneaud, V. (1971), Synthesis and pharmacological properties of deami-notocinamide and a new synthesis of tocinamide, J. Amer. Chem. Soc. 93:5539–42.

24. Brunfeldt, K. and Halstrom, J. (1970), Tritylation of a partially protected pentapeptide synthesized by the Merrifield solid phase method. Acta Chem. Scand. 24:3013–18.

25. Hodges, R. S. and Merrifield, R. B. (1974), Synthesis of O-methyl-L-serine and $N^\alpha$-tertbutyloxycarbonyl-O-methyl-L-serine, J. Org. Chem. 39:1870–2.

26. Stavropoulos, G. and Theodoropoulos, D. (1977), Synthesis of 4-substituted 1,4-benzodiazepine-3,5-diones, J. Heterocycl. Chem. 14 and 1139–43.

27. Schnyder, J. and Rottenberg, M. (1975), Improved synthesis of O-phosphohomoserine, Helv. Chem. Acta 58:518–21.

What is claimed is:

1. A modified para-nitrobenzyl esterase having improved hydrolysis activity in aqueous and aqueous/organic media relative to unmodified para-nitrobenzyl esterase of SEQ. ID. NO: 2 from Bacillus subtilis, wherein said modified para-nitrobenzyl esterase consists of unmodified para-nitrobenzyl esterase which has been modified by an amino acid substitution at one or more amino acid positions selected from the group consisting of amino acid position numbers 60, 94, 96, 144, 267, 271, 322, 334, 343, 358 and 370.

2. A modified para-nitrobenzyl esterase according to claim 1 wherein said one or more amino acid substitions are selected from the group consisting of I60V, S94G, N96S, L144M, K267R, F271L, H322R, L334V, L334S, A343V, M358V and Y370F.

3. A modified para-nitrobenzyl esterase according to claim 1 wherein said para-nitrobenzyl esterase is modified by the amino acid substitutions H322R and Y370F.

4. A modified para-nitrobenzyl esterase according to claim 1 wherein said para-nitrobenzyl esterase is modified by the amino acid substitutions H322R, M358V and Y370F.

5. A modified para-nitrobenzyl esterase according to claim 1 wherein said para-nitrobenzyl esterase is modified by the amino acid substitutions L144M, H322R, M358V and Y370F.

6. A modified para-nitrobenzyl esterase according to claim 1 wherein said para-nitrobenzyl esterase is modified by the amino acid substitutions I60V, L144M, H322R, M358V and Y370F.

7. A modified para-nitrobenzyl esterase according to claim 1 wherein said para-nitrobenzyl esterase is modified by the amino acid substitutions S94G, L144M, H322R, L334V, M358V and Y370F.

8. A modified para-nitrobenzyl esterase according to claim 1 wherein said para-nitrobenzyl esterase is modified by the amino acid substitutions L144M, K267R, H322R, L334S, M358V and Y370F.

9. A modified para-nitrobenzyl esterase according to claim 1 wherein said para-nitrobenzyl esterase is modified by the amino acid substitutions L144M, H322R, A343V, M358V and Y370F.

10. A modified para-nitrobenzyl esterase according to claim 1 wherein said para-nitrobenzyl esterase is modified by the amino acid substitutions I60V, L144M, H322R, L334S, M358V and Y370F.

11. A modified para-nitrobenzyl esterase according to claim 1 wherein said para-nitrobenzyl esterase is modified by the amino acid substitutions N96S, H322R, M358V and Y370F.

12. A modified para-nitrobenzyl esterase according to claim 1 wherein said para-nitrobenzyl esterase is modified by the amino acid substitutions H322R, Y370F, F271L, A343V.

* * * * *